(12) United States Patent
Rixon et al.

(10) Patent No.: US 7,862,814 B2
(45) Date of Patent: Jan. 4, 2011

(54) METHOD OF INHIBITING THE PROLIFERATION OF B CELL CANCERS USING TACI-IMMUNOGLOBULIN FUSION PROTEINS

(75) Inventors: Mark W. Rixon, Issaquah, WA (US); Jane A. Gross, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 12/613,039

(22) Filed: Nov. 5, 2009

(65) Prior Publication Data

US 2010/0129384 A1 May 27, 2010

Related U.S. Application Data

(60) Continuation of application No. 12/359,801, filed on Jan. 26, 2009, now Pat. No. 7,635,767, which is a division of application No. 11/242,294, filed on Oct. 3, 2005, now Pat. No. 7,501,497, which is a continuation of application No. 10/152,363, filed on May 20, 2002, now abandoned.

(60) Provisional application No. 60/293,343, filed on May 24, 2001.

(51) Int. Cl.
| | |
|---|---|
| A61K 39/395 | (2006.01) |
| C07H 21/04 | (2006.01) |
| C07K 15/00 | (2006.01) |
| C12P 21/04 | (2006.01) |
| C12P 21/08 | (2006.01) |
| C12N 15/00 | (2006.01) |

(52) U.S. Cl. ............ 424/133.1; 424/158.1; 435/69.6; 435/69.7; 435/320.1; 435/326; 530/387.3; 530/388.23

(58) Field of Classification Search ............... None
See application file for complete search history.

(56) References Cited

U.S. PATENT DOCUMENTS

| | | | |
|---|---|---|---|
| 5,523,227 | A | 6/1996 | Bram et al. |
| 5,541,291 | A | 7/1996 | Keene |
| 5,650,550 | A | 7/1997 | Korach et al. |
| 5,739,277 | A | 4/1998 | Presta et al. |
| 5,969,102 | A | 10/1999 | Bram et al. |
| 6,316,222 | B1 | 11/2001 | Bram et al. |
| 6,500,428 | B1 | 12/2002 | Bram et al. |
| 6,774,106 | B2 | 8/2004 | Theill et al. |
| 7,501,497 | B2 | 3/2009 | Rixon et al. |
| 2003/0103986 | A1 | 6/2003 | Rixon et al. |
| 2005/0183148 | A1 | 8/2005 | Bram et al. |
| 2006/0067933 | A1 | 3/2006 | Gross et al. |
| 2007/0264689 | A1 | 11/2007 | Gross et al. |
| 2009/0209006 | A1 | 8/2009 | Rixon et al. |

FOREIGN PATENT DOCUMENTS

| | | |
|---|---|---|
| EP | 0869180 A1 | 10/1998 |
| WO | WO 94/09137 | 4/1994 |
| WO | WO 95/35501 | 12/1995 |
| WO | WO 96/18641 | 6/1996 |
| WO | WO 96/27011 | 9/1996 |
| WO | WO 97/09137 | 3/1997 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12965 | 3/1999 |
| WO | WO 00/40716 | 7/2000 |
| WO | WO 00/43032 | 7/2000 |
| WO | WO 00/62790 | 10/2000 |
| WO | WO 00/67034 | 11/2000 |
| WO | WO 01/12812 | 2/2001 |
| WO | WO 01/24811 | 4/2001 |
| WO | WO 01/60397 | 8/2001 |
| WO | WO 01/77342 | 10/2001 |
| WO | WO 01/81417 | 11/2001 |
| WO | WO 01/87977 | 11/2001 |
| WO | WO 02/14504 | 2/2002 |
| WO | WO 02/38766 A2 | 5/2002 |

OTHER PUBLICATIONS

U.S. Appl. No. 60/199,946, filed Apr. 27, 2000, Ambrose et al.
U.S. Appl. No. 09/569,245, filed May 11, 2000, Gross et al.
U.S. Appl. No. 09/627,206, filed Jul. 27, 2000, Gross et al.
Gross et al., *Immunity*, 15(2) :289-302, Aug. 2001.
Gross et al., *Nature*, 404 :995-999, Apr. 27, 2000.
Bairoch, A., *Nucl. Acid Res.* 21(13):3097-3103, 1993.
Bram, R. J. and Crabtree, G. R., *Nature* 371:355-358, 1994.
Bram, R. J. et al., *Mol. Cell. Biol.* 13(8):4760-4769, 1993.
Clipstone, N. A. and Crabtree, G. R., *Nature* 357:695-697, 1992.
Crabtree, G. R. and Clipstone, N. A., *Annu. Rev. Biochem.* 63:1045-1083, 1994.
Cyster, J. G., *Nature Immunology* 1(1):9-10, 2000.
Emmel, E. A., et al., *Science* 246:1617-1620, 1989.
Fiering, S. et al., *Genes Dev.* 4:1823-1834, 1990.

(Continued)

*Primary Examiner*—David J. Blanchard
(74) *Attorney, Agent, or Firm*—Alston & Bird LLP

(57) ABSTRACT

Molecules that interfere with the binding of a tumor necrosis factor receptor with its ligand, such as a soluble receptor, have proven usefulness in both basic research and as therapeutics. The present invention provides improved soluble transmembrane activator and calcium modulator and cyclophilin ligand-interactor (TACI) receptors.

18 Claims, 7 Drawing Sheets

OTHER PUBLICATIONS

Friedman, J. Weissman, I, *Cell* 66:799-806, 1991.
Gao, X. et al., *Neurochemical Research* 24(9):1181-1188, 1999.
Gras, et al., *International Immumol*, 7(7):1093-1106, 1995.
Holloway, M. P., and Bram, R. J.,*J. Biol. Chem.* 273:16346-16350, 1998.
Holloway, M. P., and Bram, R. J.,*J. Biol. Chem.* 271:8549-8552, 1996.
Hoth, M. and Prenner, R. J., *Physiol.*, 465:359-386, 1993.
Yu et al., *Nature Immunology* 1(3):252-256, 2000.
Hatzoglou, A et al., *The Journal of Immunology* 165:1322-1330, 2000.
Imboden, J. B. et al., *Immunol*, 134:663-665, 1985.
Karttunen, J. and Shastri, N., *Proc. Natl. Acad. Sci. USA* 88:3972-3976, 1991.
Khare, S. D., et al., *Proc. Natl. Acad. Sci., USA* 97(7):3370-3375, Mar. 28, 2000.
Laâbi, et al., *EMBO J.* 11:3897-3904, 1992.
Laâbi, et al., *Nucleic Acids Res.* 22:1147-1154, 1994.
Liu, J. et al., *Cell* 66:807-815, 1991.
Mackay, et al., *J. Exp. Med.* 190:1697-1710, 1999.
Madry, et al., *Immunol.* 10:1693-1702, 1998.
Marsters, S. A., et al., *Current Biology* 10:785-788, 2000.
Moore, et al., *Science* 285:260-263, 1999.
Mukhopadhyay, et al., *J. Biol. Chem.* 274(23):15978-15981, 1999.
Novak, Anne J. et al., *Blood* 103(2):689-694, 2004.
O'Keefe, S. J. et al., *Nature* 357:692-694, 1992.
Premack, B. A. et al., *Immunol.* 152:5226-5240, 1994.
Putney, J. W., Jr. and Bird, G. St. J., *Cell* 75:199-201, 1993.
Rudinger, J., *Peptide Hormones*: 1-7, 1976.
Schneider, et al., *J. Exp. Med.*, 189(11):1747-1756, 1999.
Shu, et al., *J. Leukocyte Biol.*, 65:680-683, May 1999.
Stryer, Lubert, "Flow of Genetic Information," *Biochemistry*:111, 1996.
Takebe, Y., et al., *Mol. Cell, Biol.* 8:466-472, 1988.
Tashiro, K., et al., *Science* 261:600-603, 1993.
Thompson, J. S., et al., *Journal of Experimental Medicine* 192(1):129-135, 2000.
Truneth, A., et al., *Nature* 313:318-321, 1985.
Verweij, C. L. et al., *J. Biol. Chem.* 265:15788-15795, 1990.
Von Bülow, Götz-Ulrich and Bram, Richard, *Science* 278:138-141, 1997.
Von Bülow, Götz-Ulrich et al., *Blood* 90(10):246A-247, 1997.
Ware, C. F., *Nature* 404:949-950, 2000.
Weiss, A. and Littman, D. R., *Cell* 76:263-274, 1994.
Xia, X. et al., *Journal of Experimental Medicine* 192(1):137-143, 2000.
Yan, M. et al., *Nature Immunology* 1(1):37-41, 2000.
Zweifach, A. and Lewis, R. S., *Proc. Natl. Acad. Sci. USA* 90:6295-6299, 1993.
Birren et al., *EMBL Accession No. AC003958*, Jan. 6, 1998.
Hillier et al., *GenBank Accession No. H47097*, Aug. 16, 1995.
Hillier et al., *GenBank Accession No. R24371*, 1995.
Mishra, *GenBank Accession No. V64412*, Mar. 1, 1999.
Ramser, et al., *GenBank Accession No. AL353996*, May 20, 2000.
Von Bülow et al., *Mammalian Genome 11*: 628-632, 2000.
Wells et al., *Nature Biotech.* 17:25-26, 1999.
Zhou et al., *Blood* 98(11):808a, Abstract 3361, 2001.
Kolb, et al., *Gene* 227:21-31, 1999.
Sigmund C., *Arterioscler. Thromb. Vasc. Biol.* 1425-1429, 2000.

```
              10          20          30          40          50
     MSGLGRSRRG GRSRVDQEER FPQGLWTGVA MRSCPEEQYW DPLLGTCMSC 60          70          80          90         100
     KTICNHQSQR TCAAFCRSLS CRKEQGKFYD HLLRDCISCA SICGQHPKQC
     --------------------------------------------------------
             110         120         130         140         150
     AYFCENKLRS PVNLPPELRR QRSGEVENNS DNSGRYQGLE HRGSEASPAL

--------------------
             160         170         180         190         200
     PGLKLSADQV ALVYSTLGLC LCAVLCCFLV AVACFLKKRG DPCSCQPRSR 210         220         230         240         250
     PRQSPAKSSQ DHAMEAGSPV STSPEPVETC SFCFPECRAP TQESAVTPGT 260         270         280         290
     PDPTCAGRWG CHTRTTVLQP CPHIPDSGLG IVCVPAQEGG PGA
```

FIGURE 1

|      |     |     | LC  |     |     |     |     |     |     | HC  |     |     | HC  |     |
|------|-----|-----|-----|-----|-----|-----|-----|-----|-----|-----|-----|-----|-----|-----|
|      |     | 218 |     |     | 222 |     |     |     |     |     |     |     |     | 230 |
| wt   | Glu | Pro | Lys | Ser | Cys | Asp | Lys | Thr | His | Thr | Cys | Pro | Pro | Cys | Pro |
| Fc-488 | . | . | Arg | . | Ser | . | . | . | . | . | . | . | . | . | . |
| Fc4  | . | . | Arg | . | Ser | . | . | . | . | . | . | . | . | . | . |
| Fc5  | . | . | . | . | Ser | . | . | . | . | . | . | . | . | . | . |
| Fc6  | . | . | . | . | Ser | . | . | . | . | . | . | . | . | . | . |
| Fc7  | . | . | . | . | . | . | . | . | . | . | . | . | . | . | . |
| Fc8  | . | . | . | . | Ser | . | . | . | . | . | . | . | . | . | . |

<- hinge ->

|      |     |     |     | 234 | 235 |     | 237 |     |     |     |     |     |     |     | 245 |
|------|-----|-----|-----|-----|-----|-----|-----|-----|-----|-----|-----|-----|-----|-----|-----|
| wt   | Ala | Pro | Glu | Leu | Leu | Gly | Gly | Pro | Ser | Val | Phe | Leu | Phe | Pro | Pro |
| Fc-488 | . | . | . | . | . | . | . | . | . | . | . | . | . | . | . |
| Fc4  | . | . | . | Ala | Glu | . | Ala | . | . | . | . | . | . | . | . |
| Fc5  | . | . | . | Ala | Glu | . | Ala | . | . | . | . | . | . | . | . |
| Fc6  | . | . | . | Ala | Glu | . | Ala | . | . | . | . | . | . | . | . |
| Fc7  | . | . | . | . | . | . | . | . | . | . | . | . | . | . | . |
| Fc8  | . | . | . | . | . | . | . | . | . | . | . | . | . | . | . |

CH2 ->

|      |     |     |     |     |     |     |     |     |     |     |     |     |     |     | 260 |
|------|-----|-----|-----|-----|-----|-----|-----|-----|-----|-----|-----|-----|-----|-----|-----|
| wt   | Lys | Pro | Lys | Asp | Thr | Leu | Met | Ile | Ser | Arg | Thr | Pro | Glu | Val | Thr |
| Fc-488 | . | . | . | . | . | . | . | . | . | . | . | . | . | . | . |
| Fc4  | . | . | . | . | . | . | . | . | . | . | . | . | . | . | . |
| Fc5  | . | . | . | . | . | . | . | . | . | . | . | . | . | . | . |
| Fc6  | . | . | . | . | . | . | . | . | . | . | . | . | . | . | . |
| Fc7  | . | . | . | . | . | . | . | . | . | . | . | . | . | . | . |
| Fc8  | . | . | . | . | . | . | . | . | . | . | . | . | . | . | . |

|      |     |     |     |     |     |     |     |     |     |     |     |     |     |     | 275 |
|------|-----|-----|-----|-----|-----|-----|-----|-----|-----|-----|-----|-----|-----|-----|-----|
| wt   | Cys | Val | Val | Val | Asp | Val | Ser | His | Glu | Asp | Pro | Glu | Val | Lys | Phe |
| Fc-488 | . | . | . | . | . | . | . | . | . | . | . | . | . | . | . |
| Fc4  | . | . | . | . | . | . | . | . | . | . | . | . | . | . | . |
| Fc5  | . | . | . | . | . | . | . | . | . | . | . | . | . | . | . |
| Fc6  | . | . | . | . | . | . | . | . | . | . | . | . | . | . | . |
| Fc7  | . | . | . | . | . | . | . | . | . | . | . | . | . | . | . |
| Fc8  | . | . | . | . | . | . | . | . | . | . | . | . | . | . | . |

Figure 3A

|        |     |     |     |     |     |     |     |     |     |     |     |     |     | 290 |
|--------|-----|-----|-----|-----|-----|-----|-----|-----|-----|-----|-----|-----|-----|-----|
| wt     | Asn | Trp | Tyr | Val | Asp | Gly | Val | Glu | Val | His | Asn | Ala | Lys | Thr | Lys |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |
| Fc8    | .   | .   | .   | .   | .   | .   | .   | .   | .   | .   | .   | .   | .   | .   | .   |

|        |     |     |     |     | 297 |     |     |     |     |     |     |     | 305 |
|--------|-----|-----|-----|-----|-----|-----|-----|-----|-----|-----|-----|-----|-----|
| wt     | Pro | Arg | Glu | Glu | Gln | Tyr | Asn | Ser | Thr | Tyr | Arg | Val | Val | Ser | Val |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | Gln | .   | .   | .   | .   | .   | .   | .   | .   |
| Fc8    | .   | .   | .   | .   | .   | .   | .   | .   | .   | .   | .   | .   | .   | .   | .   |

|        |     |     |     |     |     |     |     |     |     |     |     |     |     | 320 |
|--------|-----|-----|-----|-----|-----|-----|-----|-----|-----|-----|-----|-----|-----|-----|
| wt     | Leu | Thr | Val | Leu | His | Gln | Asp | Trp | Leu | Asn | Gly | Lys | Glu | Tyr | Lys |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |
| Fc8    | .   | .   | .   | .   | .   | .   | .   | .   | .   | .   | .   | .   | .   | .   | .   |

|        |     |     |     |     |     |     |     |     | 330 | 331 |     |     |     | 335 |
|--------|-----|-----|-----|-----|-----|-----|-----|-----|-----|-----|-----|-----|-----|-----|
| wt     | Cys | Lys | Val | Ser | Asn | Lys | Ala | Leu | Pro | Ala | Pro | Ile | Glu | Lys | Thr |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | Ser | Ser | .   | .   | .   | .   |
| Fc5    | .   | .   | .   | .   | .   | .   | .   | .   | .   | Ser | Ser | .   | .   | .   | .   |
| Fc6    | .   | .   | .   | .   | .   | .   | .   | .   | .   | Ser | Ser | .   | .   | .   | .   |
| Fc7    | .   | .   | .   | .   | .   | .   | .   | .   | .   | .   | .   | .   | .   | .   | .   |
| Fc8    | .   | .   | .   | .   | .   | .   | .   | .   | .   | .   | .   | .   | .   | .   | .   |

Figure 3B

|     |     |     |     |     |     |     |     |     |     |     |     |     |     | 350 |
| --- | --- | --- | --- | --- | --- | --- | --- | --- | --- | --- | --- | --- | --- | --- |
| wt  | Ile | Ser | Lys | Ala | Lys | Gly | Gln | Pro | Arg | Glu | Pro | Gln | Val | Tyr | Thr |
| Fc-488 | .   | .   | .   | .   | .   | .   | .   | .   | .   | .   | .   | .   | .   | .   | .   |
| Fc4 | .   | .   | .   | .   | .   | .   | .   | .   | .   | .   | .   | .   | .   | .   | .   |
| Fc5 | .   | .   | .   | .   | .   | .   | .   | .   | .   | .   | .   | .   | .   | .   | .   |
| Fc6 | .   | .   | .   | .   | .   | .   | .   | .   | .   | .   | .   | .   | .   | .   | .   |
| Fc7 | .   | .   | .   | .   | .   | .   | .   | .   | .   | .   | .   | .   | .   | .   | .   |
| Fc8 | .   | .   | .   | .   | .   | .   | .   | .   | .   | .   | .   | .   | .   | .   | .   |

<- CH2 | CH3 ->

|     |     |     |     |     | 356 |     | 358 |     |     |     |     |     | 365 |
| --- | --- | --- | --- | --- | --- | --- | --- | --- | --- | --- | --- | --- | --- |
| wt  | Leu | Pro | Pro | Ser | Arg | Asp | Glu | Leu | Thr | Lys | Asn | Gln | Val | Ser | Leu |
| Fc-488 | .   | .   | .   | .   | .   | .   | .   | .   | .   | .   | .   | .   | .   | .   | .   |
| Fc4 | .   | .   | .   | .   | .   | .   | .   | .   | .   | .   | .   | .   | .   | .   | .   |
| Fc5 | .   | .   | .   | .   | .   | .   | .   | .   | .   | .   | .   | .   | .   | .   | .   |
| Fc6 | .   | .   | .   | .   | .   | .   | .   | .   | .   | .   | .   | .   | .   | .   | .   |
| Fc7 | .   | .   | .   | .   | .   | .   | .   | .   | .   | .   | .   | .   | .   | .   | .   |
| Fc8 | .   | .   | .   | .   | .   | .   | .   | .   | .   | .   | .   | .   | .   | .   | .   |

|     |     |     |     |     |     |     |     |     |     |     |     |     | 380 |
| --- | --- | --- | --- | --- | --- | --- | --- | --- | --- | --- | --- | --- | --- |
| wt  | Thr | Cys | Leu | Val | Lys | Gly | Phe | Tyr | Pro | Ser | Asp | Ile | Ala | Val | Glu |
| Fc-488 | .   | .   | .   | .   | .   | .   | .   | .   | .   | .   | .   | .   | .   | .   | .   |
| Fc4 | .   | .   | .   | .   | .   | .   | .   | .   | .   | .   | .   | .   | .   | .   | .   |
| Fc5 | .   | .   | .   | .   | .   | .   | .   | .   | .   | .   | .   | .   | .   | .   | .   |
| Fc6 | .   | .   | .   | .   | .   | .   | .   | .   | .   | .   | .   | .   | .   | .   | .   |
| Fc7 | .   | .   | .   | .   | .   | .   | .   | .   | .   | .   | .   | .   | .   | .   | .   |
| Fc8 | .   | .   | .   | .   | .   | .   | .   | .   | .   | .   | .   | .   | .   | .   | .   |

|     |     |     |     |     |     |     |     |     |     |     |     |     |     | 395 |
| --- | --- | --- | --- | --- | --- | --- | --- | --- | --- | --- | --- | --- | --- | --- |
| wt  | Trp | Glu | Ser | Asn | Gly | Gln | Pro | Glu | Asn | Asn | Tyr | Lys | Thr | Thr | Pro |
| Fc-488 | .   | .   | .   | .   | .   | .   | .   | .   | .   | .   | .   | .   | .   | .   | .   |
| Fc4 | .   | .   | .   | .   | .   | .   | .   | .   | .   | .   | .   | .   | .   | .   | .   |
| Fc5 | .   | .   | .   | .   | .   | .   | .   | .   | .   | .   | .   | .   | .   | .   | .   |
| Fc6 | .   | .   | .   | .   | .   | .   | .   | .   | .   | .   | .   | .   | .   | .   | .   |
| Fc7 | .   | .   | .   | .   | .   | .   | .   | .   | .   | .   | .   | .   | .   | .   | .   |
| Fc8 | .   | .   | .   | .   | .   | .   | .   | .   | .   | .   | .   | .   | .   | .   | .   |

Figure 3C

|     |     |     |     |     |     |     |     |     |     |     |     |     |     |     | 410 |
| --- | --- | --- | --- | --- | --- | --- | --- | --- | --- | --- | --- | --- | --- | --- | --- |
| wt  | Pro | Val | Leu | Asp | Ser | Asp | Gly | Ser | Phe | Phe | Leu | Tyr | Ser | Lys | Leu |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |
| Fc8 | . | . | . | . | . | . | . | . | . | . | . | . | . | . | . |

|     |     |     |     |     |     |     |     |     |     |     |     |     |     | 425 |
| --- | --- | --- | --- | --- | --- | --- | --- | --- | --- | --- | --- | --- | --- | --- |
| wt  | Thr | Val | Asp | Lys | Ser | Arg | Trp | Gln | Gln | Gly | Asn | Val | Phe | Ser | Cys |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |
| Fc8 | . | . | . | . | . | . | . | . | . | . | . | . | . | . | . |

|     |     |     |     | 431 |     |     |     |     |     |     |     |     |     | 440 |
| --- | --- | --- | --- | --- | --- | --- | --- | --- | --- | --- | --- | --- | --- | --- |
| wt  | Ser | Val | Met | His | Glu | Ala | Leu | His | Asn | His | Tyr | Thr | Gln | Lys | Ser |
| Fc-488 | . | . | . | . | . | . | . | . | . | . | . | . | . | . | . |
| Fc4 | . | . | . | . | . | . | . | . | . | . | . | . | . | . | . |
| Fc5 | . | . | . | . | . | . | . | . | . | . | . | . | . | . | . |
| Fc6 | . | . | . | . | . | . | . | . | . | . | . | . | . | . | . |
| Fc7 | . | . | . | . | . | . | . | . | . | . | . | . | . | . | . |
| Fc8 | . | . | . | . | . | . | . | . | . | . | . | . | . | . | . |

|     |     |     |     |     | 446 |     |     |     |
| --- | --- | --- | --- | --- | --- | --- | --- | --- |
| wt  | Leu | Ser | Leu | Ser | Pro | Gly | Lys | *** |
| Fc-488 | . | . | . | . | . | . | . | . |
| Fc4 | . | . | . | . | . | . | . | . |
| Fc5 | . | . | . | . | . | . | . | . |
| Fc6 | . | . | . | . | . | . | *** | . |
| Fc7 | . | . | . | . | . | . | . | . |
| Fc8 | . | . | . | . | . | . | . | . |

SEQUENCE LISTING

<160> NUMBER OF SEQ ID NOS: 70

<210> SEQ ID NO 1
<211> LENGTH: 1377
<212> TYPE: DNA
<213> ORGANISM: Homo sapiens
<220> FEATURE:
<221> NAME/KEY: CDS
<222> LOCATION: (14)...(892)

<400> SEQUENCE: 1
agcatcctga gta atg agt ggc ctg ggc cgg agc agg cga ggt ggc cgg    49
            Met Ser Gly Leu Gly Arg Ser Arg Arg Gly Gly Arg
            1               5                   10

| | |
|---|---|
| agc cgt gtg gac cag gag gag cgc ttt cca cag ggc ctg tgg acg ggg<br>Ser Arg Val Asp Gln Glu Glu Arg Phe Pro Gln Gly Leu Trp Thr Gly<br>     15                      20                    25 | 97 |
| gtg gct atg aga tcc tgc ccc gaa gag cag tac tgg gat cct ctg ctg<br>Val Ala Met Arg Ser Cys Pro Glu Glu Gln Tyr Trp Asp Pro Leu Leu<br>30                    35                      40 | 145 |
| ggt acc tgc atg tcc tgc aaa acc att tgc aac cat cag agc cag cgc<br>Gly Thr Cys Met Ser Cys Lys Thr Ile Cys Asn His Gln Ser Gln Arg<br>45                  50                    55                    60 | 193 |
| acc tgt gca gcc ttc tgc agg tca ctc agc tgc cgc aag gag caa ggc<br>Thr Cys Ala Ala Phe Cys Arg Ser Leu Ser Cys Arg Lys Glu Gln Gly<br>                65                    70                    75 | 241 |
| aag ttc tat gac cat ctc ctg agg gac tgc atc agc tgt gcc tcc atc<br>Lys Phe Tyr Asp His Leu Leu Arg Asp Cys Ile Ser Cys Ala Ser Ile<br>     80                      85                      90 | 289 |
| tgt gga cag cac cct aag caa tgt gca tac ttc tgt gag aac aag ctc<br>Cys Gly Gln His Pro Lys Gln Cys Ala Tyr Phe Cys Glu Asn Lys Leu<br>                95                    100                    105 | 337 |
| agg agc cca gtg aac ctt cca cca gag ctc agg aga cag cgg agt gga<br>Arg Ser Pro Val Asn Leu Pro Pro Glu Leu Arg Arg Gln Arg Ser Gly<br>110                    115                    120 | 385 |
| gaa gtt gaa aac aat tca gac aac tcg gga agg tac caa gga ttg gag<br>Glu Val Glu Asn Asn Ser Asp Asn Ser Gly Arg Tyr Gln Gly Leu Glu<br>125                    130                    135                    140 | 433 |
| cac aga ggc tca gaa gca agt cca gct ctc ccg ggg ctg aag ctg agt<br>His Arg Gly Ser Glu Ala Ser Pro Ala Leu Pro Gly Leu Lys Leu Ser<br>                    145                    150                    155 | 481 |
| gca gat cag gtg gcc ctg gtc tac agc acg ctg ggg ctc tgc ctg tgt<br>Ala Asp Gln Val Ala Leu Val Tyr Ser Thr Leu Gly Leu Cys Leu Cys<br>                        160                    165                    170 | 529 |
| gcc gtc ctc tgc tgc ttc ctg gtg gcg gtg gcc tgc ttc ctc aag aag<br>Ala Val Leu Cys Cys Phe Leu Val Ala Val Ala Cys Phe Leu Lys Lys<br>                175                    180                    185 | 577 |
| agg ggg gat ccc tgc tcc tgc cag ccc cgc tca agg ccc cgt caa agt<br>Arg Gly Asp Pro Cys Ser Cys Gln Pro Arg Ser Arg Pro Arg Gln Ser<br>          190                    195                    200 | 625 |
| ccg gcc aag tct tcc cag gat cac gcg atg gaa gcc ggc agc cct gtg<br>Pro Ala Lys Ser Ser Gln Asp His Ala Met Glu Ala Gly Ser Pro Val<br>205                    210                    215                    220 | 673 |
| agc aca tcc ccc gag cca gtg gag acc tgc agc ttc tgc ttc cct gag<br>Ser Thr Ser Pro Glu Pro Val Glu Thr Cys Ser Phe Cys Phe Pro Glu<br>                        225                    230                    235 | 721 |
| tgc agg gcg ccc acg cag gag agc gca gtc acg cct ggg acc ccc gac<br>Cys Arg Ala Pro Thr Gln Glu Ser Ala Val Thr Pro Gly Thr Pro Asp<br>                240                    245                    250 | 769 |
| ccc act tgt gct gga agg tgg ggg tgc cac acc agg acc aca gtc ctg<br>Pro Thr Cys Ala Gly Arg Trp Gly Cys His Thr Arg Thr Thr Val Leu<br>          255                    260                    265 | 817 |
| cag cct tgc cca cac atc cca gac agt ggc ctt ggc att gtg tgt gtg<br>Gln Pro Cys Pro His Ile Pro Asp Ser Gly Leu Gly Ile Val Cys Val<br>270                    275                    280 | 865 |
| cct gcc cag gag ggg ggc cca ggt gca taaatggggg tcagggaggg<br>Pro Ala Gln Glu Gly Gly Pro Gly Ala<br>285                    290 | 912 |
| aaaggaggag ggagagagat ggagaggagg ggagagagaa agagaggtgg ggagagggga | 972 |
| gagagatatg aggagagaga gacagaggag gcagaaaggg agagaaacag aggagacaga | 1032 |
| gagggagaga gagacagagg gagagagaga cagaggggaa gagaggcaga gagggaaaga | 1092 |
| ggcagagaag gaaagagaca ggcagagaag gagagaggca gagaggggaga gaggcagaga | 1152 |

-continued

```
gggagagagg cagagagaca gagagggaga gagggacaga gagagataga gcaggaggtc      1212
ggggcactct gagtcccagt tcccagtgca gctgtaggtc gtcatcacct aaccacacgt      1272
gcaataaagt cctcgtgcct gctgctcaca gcccccgaga gcccctcctc ctggagaata      1332
aaacctttgg cagctgccct tcctcaaaaa aaaaaaaaaa aaaaa                      1377
```

<210> SEQ ID NO 2
<211> LENGTH: 293
<212> TYPE: PRT
<213> ORGANISM: Homo sapiens

<400> SEQUENCE: 2

```
Met Ser Gly Leu Gly Arg Ser Arg Arg Gly Gly Arg Ser Arg Val Asp
 1               5                  10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
           100                 105                 110

Asn Leu Pro Pro Glu Leu Arg Arg Gln Arg Ser Gly Glu Val Glu Asn
       115                 120                 125

Asn Ser Asp Asn Ser Gly Arg Tyr Gln Gly Leu Glu His Arg Gly Ser
   130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
           180                 185                 190

Cys Ser Cys Gln Pro Arg Ser Arg Pro Arg Gln Ser Pro Ala Lys Ser
       195                 200                 205

Ser Gln Asp His Ala Met Glu Ala Gly Ser Pro Val Ser Thr Ser Pro
   210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
           260                 265                 270

His Ile Pro Asp Ser Gly Leu Gly Ile Val Cys Val Pro Ala Gln Glu
       275                 280                 285

Gly Gly Pro Gly Ala
   290
```

<210> SEQ ID NO 3
<211> LENGTH: 285
<212> TYPE: PRT
<213> ORGANISM: Homo sapiens

<400> SEQUENCE: 3

```
Met Asp Asp Ser Thr Glu Arg Glu Gln Ser Arg Leu Thr Ser Cys Leu
1               5                   10                  15
Lys Lys Arg Glu Glu Met Lys Leu Lys Glu Cys Val Ser Ile Leu Pro
            20                  25                  30
Arg Lys Glu Ser Pro Ser Val Arg Ser Ser Lys Asp Gly Lys Leu Leu
        35                  40                  45
Ala Ala Thr Leu Leu Leu Ala Leu Leu Ser Cys Cys Leu Thr Val Val
    50                  55                  60
Ser Phe Tyr Gln Val Ala Leu Gln Gly Asp Leu Ala Ser Leu Arg
65                  70                  75                  80
Ala Glu Leu Gln Gly His His Ala Glu Lys Leu Pro Ala Gly Ala Gly
                85                  90                  95
Ala Pro Lys Ala Gly Leu Glu Glu Ala Pro Ala Val Thr Ala Gly Leu
            100                 105                 110
Lys Ile Phe Glu Pro Pro Ala Pro Gly Glu Gly Asn Ser Ser Gln Asn
        115                 120                 125
Ser Arg Asn Lys Arg Ala Val Gln Gly Pro Glu Glu Thr Val Thr Gln
    130                 135                 140
Asp Cys Leu Gln Leu Ile Ala Asp Ser Glu Thr Pro Thr Ile Gln Lys
145                 150                 155                 160
Gly Ser Tyr Thr Phe Val Pro Trp Leu Leu Ser Phe Lys Arg Gly Ser
                165                 170                 175
Ala Leu Glu Glu Lys Glu Asn Lys Ile Leu Val Lys Glu Thr Gly Tyr
            180                 185                 190
Phe Phe Ile Tyr Gly Gln Val Leu Tyr Thr Asp Lys Thr Tyr Ala Met
        195                 200                 205
Gly His Leu Ile Gln Arg Lys Lys Val His Val Phe Gly Asp Glu Leu
    210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
                245                 250                 255
Asp Glu Leu Gln Leu Ala Ile Pro Arg Glu Asn Ala Gln Ile Ser Leu
            260                 265                 270
Asp Gly Asp Val Thr Phe Phe Gly Ala Leu Lys Leu Leu
        275                 280                 285
```

<210> SEQ ID NO 4
<211> LENGTH: 250
<212> TYPE: PRT
<213> ORGANISM: Homo sapiens

<400> SEQUENCE: 4

```
Met Pro Ala Ser Ser Pro Phe Leu Leu Ala Pro Lys Gly Pro Pro Gly
1               5                   10                  15
Asn Met Gly Gly Pro Val Arg Glu Pro Ala Leu Ser Val Ala Leu Trp
            20                  25                  30
Leu Ser Trp Gly Ala Ala Leu Gly Ala Val Ala Cys Ala Met Ala Leu
        35                  40                  45
Leu Thr Gln Gln Thr Glu Leu Gln Ser Leu Arg Arg Glu Val Ser Arg
    50                  55                  60
Leu Gln Gly Thr Gly Gly Pro Ser Gln Asn Gly Glu Gly Tyr Pro Trp
65                  70                  75                  80
```

```
Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 762
<212> TYPE: DNA
<213> ORGANISM: Homo sapiens
<220> FEATURE:
<221> NAME/KEY: CDS
<222> LOCATION: (7)...(759)

<400> SEQUENCE: 5 ggatcc atg aag cac ctg tgg ttc ttc ctc ctg ctg gtg gcg gct ccc         48
       Met Lys His Leu Trp Phe Phe Leu Leu Leu Val Ala Ala Pro
         1               5                  10 aga tgg gtc ctg tcc gag ccc aaa tct tgt gac aaa act cac aca tgc        96
Arg Trp Val Leu Ser Glu Pro Lys Ser Cys Asp Lys Thr His Thr Cys
 15              20                  25                  30 cca ccg tgc cca gca cct gaa ctc ctg ggg gga ccg tca gtc ttc ctc       144
Pro Pro Cys Pro Ala Pro Glu Leu Leu Gly Gly Pro Ser Val Phe Leu
                 35                  40                  45 ttc ccc cca aaa ccc aag gac acc ctc atg atc tcc cgg acc cct gag       192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag       240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag       288
Phe Asn Trp Tyr Val Asp Gly Val Glu Val His Asn Ala Lys Thr Lys
     80                  85                  90 ccg cgg gag gag cag tac aac agc acg tac cgt gtg gtc agc gtc ctc       336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag       384
Thr Val Leu His Gln Asp Trp Leu Asn Gly Lys Glu Tyr Lys Cys Lys
                 115                 120                 125 gtc tcc aac aaa gcc ctc cca gcc ccc atc gag aaa acc atc tcc aaa       432
Val Ser Asn Lys Ala Leu Pro Ala Pro Ile Glu Lys Thr Ile Ser Lys
```

```
                       130                 135                 140
gcc aaa ggg cag ccc cga gaa cca cag gtg tac acc ctg ccc cca tcc      480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa      528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag      576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc      624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag      672
Ser Phe Phe Leu Tyr Ser Lys Leu Thr Val Asp Lys Ser Arg Trp Gln
            210                 215                 220 cag ggg aac gtc ttc tca tgc tcc gtg atg cat gag gct ctg cac aac      720
Gln Gly Asn Val Phe Ser Cys Ser Val Met His Glu Ala Leu His Asn
        225                 230                 235 cac tac acg cag aag agc ctc tcc ctg tct ccg ggt aaa tga              762
His Tyr Thr Gln Lys Ser Leu Ser Leu Ser Pro Gly Lys
    240                 245                 250

<210> SEQ ID NO 6
<211> LENGTH: 251
<212> TYPE: PRT
<213> ORGANISM: Homo sapiens

<400> SEQUENCE: 6

Met Lys His Leu Trp Phe Phe Leu Leu Leu Val Ala Ala Pro Arg Trp
1               5                   10                  15

Val Leu Ser Glu Pro Lys Ser Cys Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
        50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220
```

```
Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 7
<211> LENGTH: 44
<212> TYPE: DNA
<213> ORGANISM: Homo sapiens
<220> FEATURE:
<223> OTHER INFORMATION: PCR primer.

<400> SEQUENCE: 7
atcagcggaa ttcagatctt cagacaaaac tcacacatgc ccac                44

<210> SEQ ID NO 8
<211> LENGTH: 35
<212> TYPE: DNA
<213> ORGANISM: Homo sapiens
<220> FEATURE:
<223> OTHER INFORMATION: PCR primer.

<400> SEQUENCE: 8
ggcagtctct agatcattta cccggagaca gggag                          35

<210> SEQ ID NO 9
<211> LENGTH: 51
<212> TYPE: DNA
<213> ORGANISM: Homo sapiens
<220> FEATURE:
<223> OTHER INFORMATION: PCR primer.

<400> SEQUENCE: 9
ccgtgcccag cacctgaagc cgaggggggca ccgtcagtct tcctcttccc c        51

<210> SEQ ID NO 10
<211> LENGTH: 31
<212> TYPE: DNA
<213> ORGANISM: Homo sapiens
<220> FEATURE:
<223> OTHER INFORMATION: PCR primer.

<400> SEQUENCE: 10
ggattctaga ttatttaccc ggagacaggg a                              31

<210> SEQ ID NO 11
<211> LENGTH: 55
<212> TYPE: DNA
<213> ORGANISM: Homo sapiens
<220> FEATURE:
<223> OTHER INFORMATION: PCR primer.

<400> SEQUENCE: 11
ggtggcggct cccagatggg tcctgtccga gcccagatct tcagacaaaa ctcac    55

<210> SEQ ID NO 12
<211> LENGTH: 18
<212> TYPE: DNA
<213> ORGANISM: Homo sapiens
<220> FEATURE:
<223> OTHER INFORMATION: PCR primer.

<400> SEQUENCE: 12
tgggagggct ttgttgga                                             18
```

<210> SEQ ID NO 13
<211> LENGTH: 42
<212> TYPE: DNA
<213> ORGANISM: Homo sapiens
<220> FEATURE:
<223> OTHER INFORMATION: PCR primer.

<400> SEQUENCE: 13
tccaacaaag ccctcccatc ctccatcgag aaaaccatct cc        42

<210> SEQ ID NO 14
<211> LENGTH: 57
<212> TYPE: DNA
<213> ORGANISM: Homo sapiens
<220> FEATURE:
<223> OTHER INFORMATION: PCR primer.

<400> SEQUENCE: 14
ggatggatcc atgaagcacc tgtggttctt cctcctgctg gtggcggctc ccagatg     57

<210> SEQ ID NO 15
<211> LENGTH: 59
<212> TYPE: DNA
<213> ORGANISM: Homo sapiens
<220> FEATURE:
<223> OTHER INFORMATION: PCR primer.

<400> SEQUENCE: 15
ctcagccagg aaatccatgc cgagttgaga cgcttccgta gaatgagtgg cctgggccg     59

<210> SEQ ID NO 16
<211> LENGTH: 48
<212> TYPE: DNA
<213> ORGANISM: Homo sapiens
<220> FEATURE:
<223> OTHER INFORMATION: PCR primer.

<400> SEQUENCE: 16
gcatgtgtga gttttgtctg aagatctggg ctccttcagc cccgggag        48

<210> SEQ ID NO 17
<211> LENGTH: 60
<212> TYPE: DNA
<213> ORGANISM: Homo sapiens
<220> FEATURE:
<223> OTHER INFORMATION: PCR primer.

<400> SEQUENCE: 17
gcacagaggc tcagaagcaa gtccagctct cccggggctg aaggagccca gatcttcaga     60

<210> SEQ ID NO 18
<211> LENGTH: 56
<212> TYPE: DNA
<213> ORGANISM: Homo sapiens
<220> FEATURE:
<223> OTHER INFORMATION: PCR primer.

<400> SEQUENCE: 18
ggggtgggta caaccccaga gctgttttaa tctagattat ttacccggag acaggg     56

<210> SEQ ID NO 19
<211> LENGTH: 36
<212> TYPE: DNA
<213> ORGANISM: Homo sapiens
<220> FEATURE:
<223> OTHER INFORMATION: PCR primer.

<400> SEQUENCE: 19
gagcccaaat cttcagacaa aactcacaca tgccca                               36

<210> SEQ ID NO 20
<211> LENGTH: 36
<212> TYPE: DNA
<213> ORGANISM: Homo sapiens
<220> FEATURE:
<223> OTHER INFORMATION: PCR primer.

<400> SEQUENCE: 20
taattggcgc gcctctagat tatttacccg gagaca                               36

<210> SEQ ID NO 21
<211> LENGTH: 37
<212> TYPE: DNA
<213> ORGANISM: Homo sapiens
<220> FEATURE:
<223> OTHER INFORMATION: PCR primer.

<400> SEQUENCE: 21
ggcgcgcctc tagattaacc cggagacagg gagaggc                              37

<210> SEQ ID NO 22
<211> LENGTH: 28
<212> TYPE: DNA
<213> ORGANISM: Homo sapiens
<220> FEATURE:
<223> OTHER INFORMATION: PCR primer.

<400> SEQUENCE: 22
gagcccaaat cttgcgacaa aactcaca                                        28

<210> SEQ ID NO 23
<211> LENGTH: 33
<212> TYPE: DNA
<213> ORGANISM: Homo sapiens
<220> FEATURE:
<223> OTHER INFORMATION: PCR primer.

<400> SEQUENCE: 23
gtacgtgctt tggtactgct cctcccgcgg ctt                                  33

<210> SEQ ID NO 24
<211> LENGTH: 28
<212> TYPE: DNA
<213> ORGANISM: Homo sapiens
<220> FEATURE:
<223> OTHER INFORMATION: PCR primer.

<400> SEQUENCE: 24
cagtaccaaa gcacgtaccg tgtggtca                                        28

<210> SEQ ID NO 25
<211> LENGTH: 35
<212> TYPE: PRT
<213> ORGANISM: Homo sapiens
<220> FEATURE:
<223> OTHER INFORMATION: Optimized tPA leader.

<400> SEQUENCE: 25

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg

```
                20                  25                  30
Phe Arg Arg
        35

<210> SEQ ID NO 26
<211> LENGTH: 995
<212> TYPE: DNA
<213> ORGANISM: Homo sapiens
<220> FEATURE:
<221> NAME/KEY: CDS
<222> LOCATION: (219)...(770)

<400> SEQUENCE: 26
aagactcaaa cttagaaact tgaattagat gtggtattca aatccttacg tgccgcgaag      60
acacagacag cccccgtaag aacccacgaa gcaggcgaag ttcattgttc tcaacattct     120
agctgctctt gctgcatttg ctctggaatt cttgtagaga tattacttgt ccttccaggc     180
tgttctttct gtagctccct gttttctttt tgtgatc atg ttg cag atg gct ggg     236
                                        Met Leu Gln Met Ala Gly
                                          1               5 cag tgc tcc caa aat gaa tat ttt gac agt ttg ttg cat gct tgc ata       284
Gln Cys Ser Gln Asn Glu Tyr Phe Asp Ser Leu Leu His Ala Cys Ile
             10                  15                  20 cct tgt caa ctt cga tgt tct tct aat act cct cct cta aca tgt cag       332
Pro Cys Gln Leu Arg Cys Ser Ser Asn Thr Pro Pro Leu Thr Cys Gln
         25                  30                  35 cgt tat tgt aat gca agt gtg acc aat tca gtg aaa gga acg aat gcg       380
Arg Tyr Cys Asn Ala Ser Val Thr Asn Ser Val Lys Gly Thr Asn Ala
     40                  45                  50 att ctc tgg acc tgt ttg gga ctg agc tta ata att tct ttg gca gtt       428
Ile Leu Trp Thr Cys Leu Gly Leu Ser Leu Ile Ile Ser Leu Ala Val
 55                  60                  65                  70 ttc gtg cta atg ttt ttg cta agg aag ata agc tct gaa cca tta aag       476
Phe Val Leu Met Phe Leu Leu Arg Lys Ile Ser Ser Glu Pro Leu Lys
                 75                  80                  85 gac gag ttt aaa aac aca gga tca ggt ctc ctg ggc atg gct aac att       524
Asp Glu Phe Lys Asn Thr Gly Ser Gly Leu Leu Gly Met Ala Asn Ile
             90                  95                 100 gac ctg gaa aag agc agg act ggt gat gaa att att ctt ccg aga ggc       572
Asp Leu Glu Lys Ser Arg Thr Gly Asp Glu Ile Ile Leu Pro Arg Gly
        105                 110                 115 ctc gag tac acg gtg gaa gaa tgc acc tgt gaa gac tgc atc aag agc       620
Leu Glu Tyr Thr Val Glu Glu Cys Thr Cys Glu Asp Cys Ile Lys Ser
    120                 125                 130 aaa ccg aag gtc gac tct gac cat tgc ttt cca ctc cca gct atg gag       668
Lys Pro Lys Val Asp Ser Asp His Cys Phe Pro Leu Pro Ala Met Glu
135                 140                 145                 150 gaa ggc gca acc att ctt gtc acc acg aaa acg aat gac tat tgc aag       716
Glu Gly Ala Thr Ile Leu Val Thr Thr Lys Thr Asn Asp Tyr Cys Lys
                155                 160                 165 agc ctg cca gct gct ttg agt gct acg gag ata gag aaa tca att tct       764
Ser Leu Pro Ala Ala Leu Ser Ala Thr Glu Ile Glu Lys Ser Ile Ser
            170                 175                 180 gct agg taattaacca tttcgactcg agcagtgcca ctttaaaaat cttttgtcag        820
Ala Arg aatagatgat gtgtcagatc tctttaggat gactgtattt ttcagttgcc gatacagctt     880
tttgtcctct aactgtggaa actctttatg ttagatatat ttctctaggt tactgttggg     940
agcttaatgg tagaaacttc cttggtttca tgattaaagt ctttttttttt cctga         995
```

<210> SEQ ID NO 27
<211> LENGTH: 184
<212> TYPE: PRT
<213> ORGANISM: Homo sapiens

<400> SEQUENCE: 27

```
Met Leu Gln Met Ala Gly Gln Cys Ser Gln Asn Glu Tyr Phe Asp Ser
 1               5                  10                  15

Leu Leu His Ala Cys Ile Pro Cys Gln Leu Arg Cys Ser Ser Asn Thr
             20                  25                  30

Pro Pro Leu Thr Cys Gln Arg Tyr Cys Asn Ala Ser Val Thr Asn Ser
         35                  40                  45

Val Lys Gly Thr Asn Ala Ile Leu Trp Thr Cys Leu Gly Leu Ser Leu
     50                  55                  60

Ile Ile Ser Leu Ala Val Phe Val Leu Met Phe Leu Leu Arg Lys Ile
 65                  70                  75                  80

Ser Ser Glu Pro Leu Lys Asp Glu Phe Lys Asn Thr Gly Ser Gly Leu
                 85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 28
<211> LENGTH: 762
<212> TYPE: DNA
<213> ORGANISM: Homo sapiens
<220> FEATURE:
<221> NAME/KEY: CDS
<222> LOCATION: (7)...(759)

<400> SEQUENCE: 28

```
ggatcc atg aag cac ctg tgg ttc ttc ctc ctg ctg gtg gcg gct ccc        48
       Met Lys His Leu Trp Phe Phe Leu Leu Leu Val Ala Ala Pro
        1               5                  10 aga tgg gtc ctg tcc gag ccc aga tct tca gac aaa act cac aca tgc       96
Arg Trp Val Leu Ser Glu Pro Arg Ser Ser Asp Lys Thr His Thr Cys
 15                  20                  25                  30 cca ccg tgc cca gca cct gaa ctc ctg ggg gga ccg tca gtc ttc ctc      144
Pro Pro Cys Pro Ala Pro Glu Leu Leu Gly Gly Pro Ser Val Phe Leu
             35                  40                  45 ttc ccc cca aaa ccc aag gac acc ctc atg atc tcc cgg acc cct gag      192
Phe Pro Pro Lys Pro Lys Asp Thr Leu Met Ile Ser Arg Thr Pro Glu
         50                  55                  60 gtc aca tgc gtg gtg gtg gac gtg agc cac gaa gac cct gag gtc aag      240
Val Thr Cys Val Val Val Asp Val Ser His Glu Asp Pro Glu Val Lys
     65                  70                  75 ttc aac tgg tac gtg gac ggc gtg gag gtg cat aat gcc aag aca aag      288
Phe Asn Trp Tyr Val Asp Gly Val Glu Val His Asn Ala Lys Thr Lys
 80                  85                  90
```

```
ccg cgg gag gag cag tac aac agc acg tac cgt gtg gtc agc gtc ctc        336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag        384
Thr Val Leu His Gln Asp Trp Leu Asn Gly Lys Glu Tyr Lys Cys Lys
                115                 120                 125 gtc tcc aac aaa gcc ctc cca gcc ccc atc gag aaa acc atc tcc aaa        432
Val Ser Asn Lys Ala Leu Pro Ala Pro Ile Glu Lys Thr Ile Ser Lys
            130                 135                 140 gcc aaa ggg cag ccc cga gaa cca cag gtg tac acc ctg ccc cca tcc        480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa        528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag        576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc        624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag        672
Ser Phe Phe Leu Tyr Ser Lys Leu Thr Val Asp Lys Ser Arg Trp Gln
            210                 215                 220 cag ggg aac gtc ttc tca tgc tcc gtg atg cat gag gct ctg cac aac        720
Gln Gly Asn Val Phe Ser Cys Ser Val Met His Glu Ala Leu His Asn
        225                 230                 235 cac tac acg cag aag agc ctc tcc ctg tct ccg ggt aaa tga                762
His Tyr Thr Gln Lys Ser Leu Ser Leu Ser Pro Gly Lys
    240                 245                 250

<210> SEQ ID NO 29
<211> LENGTH: 251
<212> TYPE: PRT
<213> ORGANISM: Homo sapiens

<400> SEQUENCE: 29

Met Lys His Leu Trp Phe Phe Leu Leu Leu Val Ala Ala Pro Arg Trp
 1               5                  10                  15

Val Leu Ser Glu Pro Arg Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
```

```
                     165                 170                 175
Tyr Pro Ser Asp Ile Ala Val Glu Trp Glu Ser Asn Gly Gln Pro Glu
                 180                 185                 190

Asn Asn Tyr Lys Thr Thr Pro Pro Val Leu Asp Ser Asp Gly Ser Phe
             195                 200                 205

Phe Leu Tyr Ser Lys Leu Thr Val Asp Lys Ser Arg Trp Gln Gln Gly
         210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                 245                 250

<210> SEQ ID NO 30
<211> LENGTH: 762
<212> TYPE: DNA
<213> ORGANISM: Homo sapiens
<220> FEATURE:
<221> NAME/KEY: CDS
<222> LOCATION: (7)...(759)
<223> OTHER INFORMATION: Modified immunoglobulin moiety.

<400> SEQUENCE: 30 ggatcc atg aag cac ctg tgg ttc ttc ctc ctg ctg gtg gcg gct ccc         48
       Met Lys His Leu Trp Phe Phe Leu Leu Leu Val Ala Ala Pro
       1               5                  10 aga tgg gtc ctg tcc gag ccc aga tct tca gac aaa act cac aca tgc       96
Arg Trp Val Leu Ser Glu Pro Arg Ser Ser Asp Lys Thr His Thr Cys
 15                  20                  25                  30 cca ccg tgc cca gca cct gaa gcc gag ggg gca ccg tca gtc ttc ctc      144
Pro Pro Cys Pro Ala Pro Glu Ala Glu Gly Ala Pro Ser Val Phe Leu
                 35                  40                  45 ttc ccc cca aaa ccc aag gac acc ctc atg atc tcc cgg acc cct gag      192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag      240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag      288
Phe Asn Trp Tyr Val Asp Gly Val Glu Val His Asn Ala Lys Thr Lys
     80                  85                  90 ccg cgg gag gag cag tac aac agc acg tac cgt gtg gtc agc gtc ctc      336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag      384
Thr Val Leu His Gln Asp Trp Leu Asn Gly Lys Glu Tyr Lys Cys Lys
                115                 120                 125 gtc tcc aac aaa gcc ctc cca tcc tcc atc gag aaa acc atc tcc aaa      432
Val Ser Asn Lys Ala Leu Pro Ser Ser Ile Glu Lys Thr Ile Ser Lys
            130                 135                 140 gcc aaa ggg cag ccc cga gaa cca cag gtg tac acc ctg ccc cca tcc      480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa      528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag      576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc      624
Pro Glu Asn Asn Tyr Lys Thr Thr Pro Pro Val Leu Asp Ser Asp Gly
```

-continued

```
                          195                 200                 205
tcc ttc ttc ctc tac agc aag ctc acc gtg gac aag agc agg tgg cag        672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac        720
Gln Gly Asn Val Phe Ser Cys Ser Val Met His Glu Ala Leu His Asn
                225                 230                 235 cac tac acg cag aag agc ctc tcc ctg tct ccg ggt aaa tga                762
His Tyr Thr Gln Lys Ser Leu Ser Leu Ser Pro Gly Lys
        240                 245                 250
```

<210> SEQ ID NO 31
<211> LENGTH: 251
<212> TYPE: PRT
<213> ORGANISM: Homo sapiens

<400> SEQUENCE: 31

```
Met Lys His Leu Trp Phe Phe Leu Leu Leu Val Ala Ala Pro Arg Trp
 1               5                  10                  15

Val Leu Ser Glu Pro Arg Ser Ser Asp Lys Thr His Thr Cys Pro Pro
            20                  25                  30

Cys Pro Ala Pro Glu Ala Glu Gly Ala Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ser Ser Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250
```

<210> SEQ ID NO 32
<211> LENGTH: 762
<212> TYPE: DNA
<213> ORGANISM: Homo sapiens
<220> FEATURE:
<221> NAME/KEY: CDS
<222> LOCATION: (7)...(759)
<223> OTHER INFORMATION: Modified immunoglobulin moiety.

<400> SEQUENCE: 32

```
ggatcc atg aag cac ctg tgg ttc ttc ctc ctg ctg gtg gcg gct ccc         48
       Met Lys His Leu Trp Phe Phe Leu Leu Leu Val Ala Ala Pro
         1               5                  10 aga tgg gtc ctg tcc gag ccc aaa tct tca gac aaa act cac aca tgc         96
Arg Trp Val Leu Ser Glu Pro Lys Ser Ser Asp Lys Thr His Thr Cys
 15                  20                  25                  30 cca ccg tgc cca gca cct gaa gcc gag ggg gca ccg tca gtc ttc ctc        144
Pro Pro Cys Pro Ala Pro Glu Ala Glu Gly Ala Pro Ser Val Phe Leu
                 35                  40                  45 ttc ccc cca aaa ccc aag gac acc ctc atg atc tcc cgg acc cct gag        192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag        240
Val Thr Cys Val Val Val Asp Val Ser His Glu Asp Pro Glu Val Lys
 65                  70                  75 ttc aac tgg tac gtg gac ggc gtg gag gtg cat aat gcc aag aca aag        288
Phe Asn Trp Tyr Val Asp Gly Val Glu Val His Asn Ala Lys Thr Lys
         80                  85                  90 ccg cgg gag gag cag tac aac agc acg tac cgt gtg gtc agc gtc ctc        336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag        384
Thr Val Leu His Gln Asp Trp Leu Asn Gly Lys Glu Tyr Lys Cys Lys
                115                 120                 125 gtc tcc aac aaa gcc ctc cca tcc tcc atc gag aaa acc atc tcc aaa        432
Val Ser Asn Lys Ala Leu Pro Ser Ser Ile Glu Lys Thr Ile Ser Lys
            130                 135                 140 gcc aaa ggg cag ccc cga gaa cca cag gtg tac acc ctg ccc cca tcc        480
Ala Lys Gly Gln Pro Arg Glu Pro Gln Val Tyr Thr Leu Pro Pro Ser
145                 150                 155 cgg gat gag ctg acc aag aac cag gtc agc ctg acc tgc ctg gtc aaa        528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag        576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc        624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag        672
Ser Phe Phe Leu Tyr Ser Lys Leu Thr Val Asp Lys Ser Arg Trp Gln
            210                 215                 220 cag ggg aac gtc ttc tca tgc tcc gtg atg cat gag gct ctg cac aac        720
Gln Gly Asn Val Phe Ser Cys Ser Val Met His Glu Ala Leu His Asn
        225                 230                 235 cac tac acg cag aag agc ctc tcc ctg tct ccg ggt aaa tga               762
His Tyr Thr Gln Lys Ser Leu Ser Leu Ser Pro Gly Lys
    240                 245                 250

<210> SEQ ID NO 33
<211> LENGTH: 251
<212> TYPE: PRT
<213> ORGANISM: Homo sapiens

<400> SEQUENCE: 33

Met Lys His Leu Trp Phe Phe Leu Leu Leu Val Ala Ala Pro Arg Trp
  1               5                  10                  15

Val Leu Ser Glu Pro Lys Ser Ser Asp Lys Thr His Thr Cys Pro Pro
```

```
                 20                  25                  30
Cys Pro Ala Pro Glu Ala Glu Gly Ala Pro Ser Val Phe Leu Phe Pro
     35                  40                  45

Pro Lys Pro Lys Asp Thr Leu Met Ile Ser Arg Thr Pro Glu Val Thr
 50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ser Ser Ile Glu Lys Thr Ile Ser Lys Ala Lys
        130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 34
<211> LENGTH: 759
<212> TYPE: DNA
<213> ORGANISM: Homo sapiens
<220> FEATURE:
<221> NAME/KEY: CDS
<222> LOCATION: (7)...(756)
<223> OTHER INFORMATION: Modified immunoglobulin moiety.

<400> SEQUENCE: 34 ggatcc atg aag cac ctg tgg ttc ttc ctc ctg ctg gtg gcg gct ccc        48
       Met Lys His Leu Trp Phe Phe Leu Leu Leu Val Ala Ala Pro
         1               5                  10 aga tgg gtc ctg tcc gag ccc aaa tct tca gac aaa act cac aca tgc       96
Arg Trp Val Leu Ser Glu Pro Lys Ser Ser Asp Lys Thr His Thr Cys
 15                  20                  25                  30 cca ccg tgc cca gca cct gaa gcc gag ggg gca ccg tca gtc ttc ctc      144
Pro Pro Cys Pro Ala Pro Glu Ala Glu Gly Ala Pro Ser Val Phe Leu
                 35                  40                  45 ttc ccc cca aaa ccc aag gac acc ctc atg atc tcc cgg acc cct gag      192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag      240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag      288
Phe Asn Trp Tyr Val Asp Gly Val Glu Val His Asn Ala Lys Thr Lys
     80                  85                  90
```

```
ccg cgg gag gag cag tac aac agc acg tac cgt gtg tcc agc gtc ctc         336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag         384
Thr Val Leu His Gln Asp Trp Leu Asn Gly Lys Glu Tyr Lys Cys Lys
                115                 120                 125 gtc tcc aac aaa gcc ctc cca tcc tcc atc gag aaa acc atc tcc aaa         432
Val Ser Asn Lys Ala Leu Pro Ser Ser Ile Glu Lys Thr Ile Ser Lys
        130                 135                 140 gcc aaa ggg cag ccc cga gaa cca cag gtg tac acc ctg ccc cca tcc         480
Ala Lys Gly Gln Pro Arg Glu Pro Gln Val Tyr Thr Leu Pro Pro Ser
    145                 150                 155 cgg gat gag ctg acc aag aac cag gtc agc ctg acc tgc ctg gtc aaa         528
Arg Asp Glu Leu Thr Lys Asn Gln Val Ser Leu Thr Cys Leu Val Lys
160                 165                 170 ggc ttc tat ccc agc gac atc gcc gtg gag tgg gag agc aat ggg cag         576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc         624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag         672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac         720
Gln Gly Asn Val Phe Ser Cys Ser Val Met His Glu Ala Leu His Asn
    225                 230                 235 cac tac acg cag aag agc ctc tcc ctg tct ccg ggt tga                     759
His Tyr Thr Gln Lys Ser Leu Ser Leu Ser Pro Gly
240                 245                 250

<210> SEQ ID NO 35
<211> LENGTH: 250
<212> TYPE: PRT
<213> ORGANISM: Homo sapiens

<400> SEQUENCE: 35

Met Lys His Leu Trp Phe Phe Leu Leu Leu Val Ala Ala Pro Arg Trp
 1               5                   10                  15

Val Leu Ser Glu Pro Lys Ser Ser Asp Lys Thr His Thr Cys Pro Pro
                20                  25                  30

Cys Pro Ala Pro Glu Ala Glu Gly Ala Pro Ser Val Phe Leu Phe Pro
            35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
    115                 120                 125

Asn Lys Ala Leu Pro Ser Ser Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160
```

```
Glu Leu Thr Lys Asn Gln Val Ser Leu Thr Cys Leu Val Lys Gly Phe
            165                 170                 175

Tyr Pro Ser Asp Ile Ala Val Glu Trp Glu Ser Asn Gly Gln Pro Glu
        180                 185                 190

Asn Asn Tyr Lys Thr Thr Pro Val Leu Asp Ser Asp Gly Ser Phe
            195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly
            245                 250

<210> SEQ ID NO 36
<211> LENGTH: 762
<212> TYPE: DNA
<213> ORGANISM: Homo sapiens
<220> FEATURE:
<221> NAME/KEY: CDS
<222> LOCATION: (7)...(759)
<223> OTHER INFORMATION: Modified immunoglobulin moiety.

<400> SEQUENCE: 36 ggatcc atg aag cac ctg tgg ttc ttc ctc ctg ctg gtg gcg gct ccc       48
       Met Lys His Leu Trp Phe Phe Leu Leu Leu Val Ala Ala Pro
        1               5                  10 aga tgg gtc ctg tcc gag ccc aaa tct tgc gac aaa act cac aca tgc      96
Arg Trp Val Leu Ser Glu Pro Lys Ser Cys Asp Lys Thr His Thr Cys
 15                 20                  25                  30 cca ccg tgc cca gca cct gaa ctc ctg ggg gga ccg tca gtc ttc ctc     144
Pro Pro Cys Pro Ala Pro Glu Leu Leu Gly Gly Pro Ser Val Phe Leu
                35                  40                  45 ttc ccc cca aaa ccc aag gac acc ctc atg atc tcc cgg acc cct gag     192
Phe Pro Pro Lys Pro Lys Asp Thr Leu Met Ile Ser Arg Thr Pro Glu
         50                  55                  60 gtc aca tgc gtg gtg gtg gac gtg agc cac gaa gac cct gag gtc aag     240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag     288
Phe Asn Trp Tyr Val Asp Gly Val Glu Val His Asn Ala Lys Thr Lys
 80                  85                  90 ccg cgg gag gag cag tac caa agc acg tac cgt gtg gtc agc gtc ctc     336
Pro Arg Glu Glu Gln Tyr Gln Ser Thr Tyr Arg Val Val Ser Val Leu
 95                 100                 105                 110 acc gtc ctg cac cag gac tgg ctg aat ggc aag gag tac aag tgc aag     384
Thr Val Leu His Gln Asp Trp Leu Asn Gly Lys Glu Tyr Lys Cys Lys
                115                 120                 125 gtc tcc aac aaa gcc ctc cca gcc ccc atc gag aaa acc atc tcc aaa     432
Val Ser Asn Lys Ala Leu Pro Ala Pro Ile Glu Lys Thr Ile Ser Lys
            130                 135                 140 gcc aaa ggg cag ccc cga gaa cca cag gtg tac acc ctg ccc cca tcc     480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa     528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag     576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc     624
```

```
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag       672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac       720
Gln Gly Asn Val Phe Ser Cys Ser Val Met His Glu Ala Leu His Asn
                225                 230                 235 cac tac acg cag aag agc ctc tcc ctg tct ccg ggt aaa tga               762
His Tyr Thr Gln Lys Ser Leu Ser Leu Ser Pro Gly Lys
        240                 245                 250

<210> SEQ ID NO 37
<211> LENGTH: 251
<212> TYPE: PRT
<213> ORGANISM: Homo sapiens

<400> SEQUENCE: 37

Met Lys His Leu Trp Phe Phe Leu Leu Leu Val Ala Ala Pro Arg Trp
 1               5                  10                  15

Val Leu Ser Glu Pro Lys Ser Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Gln Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 38
<211> LENGTH: 762
<212> TYPE: DNA
<213> ORGANISM: Homo sapiens
<220> FEATURE:
<221> NAME/KEY: CDS
<222> LOCATION: (7)...(759)
```

<223> OTHER INFORMATION: Modified immunoglobulin moiety.

<400> SEQUENCE: 38

```
ggatcc atg aag cac ctg tgg ttc ttc ctc ctg ctg gtg gcg gct ccc          48
       Met Lys His Leu Trp Phe Phe Leu Leu Leu Val Ala Ala Pro
       1               5                   10 aga tgg gtc ctg tcc gag ccc aaa tct tca gac aaa act cac aca tgc          96
Arg Trp Val Leu Ser Glu Pro Lys Ser Ser Asp Lys Thr His Thr Cys
15                  20                  25                  30 cca ccg tgc cca gca cct gaa ctc ctg ggg gga ccg tca gtc ttc ctc         144
Pro Pro Cys Pro Ala Pro Glu Leu Leu Gly Gly Pro Ser Val Phe Leu
                35                  40                  45 ttc ccc cca aaa ccc aag gac acc ctc atg atc tcc cgg acc cct gag         192
Phe Pro Pro Lys Pro Lys Asp Thr Leu Met Ile Ser Arg Thr Pro Glu
        50                  55                  60 gtc aca tgc gtg gtg gtg gac gtg agc cac gaa gac cct gag gtc aag         240
Val Thr Cys Val Val Val Asp Val Ser His Glu Asp Pro Glu Val Lys
    65                  70                  75 ttc aac tgg tac gtg gac ggc gtg gag gtg cat aat gcc aag aca aag         288
Phe Asn Trp Tyr Val Asp Gly Val Glu Val His Asn Ala Lys Thr Lys
80                  85                  90 ccg cgg gag gag cag tac aac agc acg tac cgt gtg gtc agc gtc ctc         336
Pro Arg Glu Glu Gln Tyr Asn Ser Thr Tyr Arg Val Val Ser Val Leu
95                  100                 105                 110 acc gtc ctg cac cag gac tgg ctg aat ggc aag gag tac aag tgc aag         384
Thr Val Leu His Gln Asp Trp Leu Asn Gly Lys Glu Tyr Lys Cys Lys
                115                 120                 125 gtc tcc aac aaa gcc ctc cca gcc ccc atc gag aaa acc atc tcc aaa         432
Val Ser Asn Lys Ala Leu Pro Ala Pro Ile Glu Lys Thr Ile Ser Lys
        130                 135                 140 gcc aaa ggg cag ccc cga gaa cca cag gtg tac acc ctg ccc cca tcc         480
Ala Lys Gly Gln Pro Arg Glu Pro Gln Val Tyr Thr Leu Pro Pro Ser
    145                 150                 155 cgg gat gag ctg acc aag aac cag gtc agc ctg acc tgc ctg gtc aaa         528
Arg Asp Glu Leu Thr Lys Asn Gln Val Ser Leu Thr Cys Leu Val Lys
160                 165                 170 ggc ttc tat ccc agc gac atc gcc gtg gag tgg gag agc aat ggg cag         576
Gly Phe Tyr Pro Ser Asp Ile Ala Val Glu Trp Glu Ser Asn Gly Gln
175                 180                 185                 190 ccg gag aac aac tac aag acc acg cct ccc gtg ctg gac tcc gac ggc         624
Pro Glu Asn Asn Tyr Lys Thr Thr Pro Pro Val Leu Asp Ser Asp Gly
                195                 200                 205 tcc ttc ttc ctc tac agc aag ctc acc gtg gac aag agc agg tgg cag         672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac         720
Gln Gly Asn Val Phe Ser Cys Ser Val Met His Glu Ala Leu His Asn
    225                 230                 235 cac tac acg cag aag agc ctc tcc ctg tct ccg ggt aaa tga               762
His Tyr Thr Gln Lys Ser Leu Ser Leu Ser Pro Gly Lys
240                 245                 250
```

<210> SEQ ID NO 39
<211> LENGTH: 251
<212> TYPE: PRT
<213> ORGANISM: Homo sapiens

<400> SEQUENCE: 39

```
Met Lys His Leu Trp Phe Phe Leu Leu Leu Val Ala Ala Pro Arg Trp
1               5                   10                  15
```

```
Val Leu Ser Glu Pro Lys Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 40
<211> LENGTH: 29
<212> TYPE: DNA
<213> ORGANISM: Homo sapiens
<220> FEATURE:
<223> OTHER INFORMATION: PCR primer.

<400> SEQUENCE: 40
tattaggccg gccaccatgg atgcaatga                                         29

<210> SEQ ID NO 41
<211> LENGTH: 29
<212> TYPE: DNA
<213> ORGANISM: Homo sapiens
<220> FEATURE:
<223> OTHER INFORMATION: PCR primer.

<400> SEQUENCE: 41
tgaagatttg ggctccttga gacctggga                                         29

<210> SEQ ID NO 42
<211> LENGTH: 29
<212> TYPE: DNA
<213> ORGANISM: Homo sapiens
<220> FEATURE:
<223> OTHER INFORMATION: PCR primer.

<400> SEQUENCE: 42
```
tcccaggtct caaggagccc aaatcttca                                29

<210> SEQ ID NO 43
<211> LENGTH: 30
<212> TYPE: DNA
<213> ORGANISM: Homo sapiens
<220> FEATURE:
<223> OTHER INFORMATION: PCR primer.

<400> SEQUENCE: 43
tgaagatttg ggctcgttct cacagaagta                               30

<210> SEQ ID NO 44
<211> LENGTH: 31
<212> TYPE: DNA
<213> ORGANISM: Homo sapiens
<220> FEATURE:
<223> OTHER INFORMATION: PCR primer.

<400> SEQUENCE: 44
atacttctgt gagaacgagc ccaaatcttc a                             31

<210> SEQ ID NO 45
<211> LENGTH: 30
<212> TYPE: DNA
<213> ORGANISM: Homo sapiens
<220> FEATURE:
<223> OTHER INFORMATION: PCR primer.

<400> SEQUENCE: 45
tttgggctcg ctcctgagct tgttctcaca                               30

<210> SEQ ID NO 46
<211> LENGTH: 28
<212> TYPE: DNA
<213> ORGANISM: Homo sapiens
<220> FEATURE:
<223> OTHER INFORMATION: PCR primer.

<400> SEQUENCE: 46
ctcaggagcg agcccaaatc ttcagaca                                 28

<210> SEQ ID NO 47
<211> LENGTH: 26
<212> TYPE: DNA
<213> ORGANISM: Homo sapiens
<220> FEATURE:
<223> OTHER INFORMATION: PCR primer.

<400> SEQUENCE: 47
tttgggctcc ctgagctctg gtggaa                                   26

<210> SEQ ID NO 48
<211> LENGTH: 28
<212> TYPE: DNA
<213> ORGANISM: Homo sapiens
<220> FEATURE:
<223> OTHER INFORMATION: PCR primer.

<400> SEQUENCE: 48
gagctcaggg agcccaaatc ttcagaca                                 28

<210> SEQ ID NO 49
<211> LENGTH: 1214
<212> TYPE: DNA
<213> ORGANISM: Homo sapiens

```
<220> FEATURE:
<221> NAME/KEY: CDS
<222> LOCATION: (17)...(1192)
<223> OTHER INFORMATION: coding sequence for fusion protein

<400> SEQUENCE: 49
tattaggccg gccacc atg gat gca atg aag aga ggg ctc tgc tgt gtg ctg         52
               Met Asp Ala Met Lys Arg Gly Leu Cys Cys Val Leu
                 1               5                  10 ctg ctg tgt ggc gcc gtc ttc gtt tcg ctc agc cag gaa atc cat gcc          100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag          148
Glu Leu Arg Arg Phe Arg Arg Ala Met Arg Ser Cys Pro Glu Glu Gln
 30                  35                  40 tac tgg gat cct ctg ctg ggt acc tgc atg tcc tgc aaa acc att tgc          196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc          244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc          292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac          340
Ile Ser Cys Ala Ser Ile Cys Gly Gln His Pro Lys Gln Cys Ala Tyr
             95                 100                 105 ttc tgt gag aac aag ctc agg agc cca gtg aac ctt cca cca gag ctc          388
Phe Cys Glu Asn Lys Leu Arg Ser Pro Val Asn Leu Pro Pro Glu Leu
110                 115                 120 agg aga cag cgg agt gga gaa gtt gaa aac aat tca gac aac tcg gga          436
Arg Arg Gln Arg Ser Gly Glu Val Glu Asn Asn Ser Asp Asn Ser Gly
125                 130                 135                 140 agg tac caa gga ttg gag cac aga ggc tca gaa gca agt cca gct ctc          484
Arg Tyr Gln Gly Leu Glu His Arg Gly Ser Glu Ala Ser Pro Ala Leu
                145                 150                 155 cca ggt ctc aag gag ccc aaa tct tca gac aaa act cac aca tgc cca          532
Pro Gly Leu Lys Glu Pro Lys Ser Ser Asp Lys Thr His Thr Cys Pro
        160                 165                 170 ccg tgc cca gca cct gaa gcc gag ggg gca ccg tca gtc ttc ctc ttc          580
Pro Cys Pro Ala Pro Glu Ala Glu Gly Ala Pro Ser Val Phe Leu Phe
    175                 180                 185 ccc cca aaa ccc aag gac acc ctc atg atc tcc cgg acc cct gag gtc          628
Pro Pro Lys Pro Lys Asp Thr Leu Met Ile Ser Arg Thr Pro Glu Val
190                 195                 200 aca tgc gtg gtg gtg gac gtg agc cac gaa gac cct gag gtc aag ttc          676
Thr Cys Val Val Val Asp Val Ser His Glu Asp Pro Glu Val Lys Phe
205                 210                 215                 220 aac tgg tac gtg gac ggc gtg gag gtg cat aat gcc aag aca aag ccg          724
Asn Trp Tyr Val Asp Gly Val Glu Val His Asn Ala Lys Thr Lys Pro
                225                 230                 235 cgg gag gag cag tac aac agc acg tac cgt gtg gtc agc gtc ctc acc          772
Arg Glu Glu Gln Tyr Asn Ser Thr Tyr Arg Val Val Ser Val Leu Thr
        240                 245                 250 gtc ctg cac cag gac tgg ctg aat ggc aag gag tac aag tgc aag gtc          820
Val Leu His Gln Asp Trp Leu Asn Gly Lys Glu Tyr Lys Cys Lys Val
    255                 260                 265 tcc aac aaa gcc ctc cca tcc tcc atc gag aaa acc atc tcc aaa gcc          868
Ser Asn Lys Ala Leu Pro Ser Ser Ile Glu Lys Thr Ile Ser Lys Ala
270                 275                 280
```

```
aaa ggg cag ccc cga gaa cca cag gtg tac acc ctg ccc cca tcc cgg      916
Lys Gly Gln Pro Arg Glu Pro Gln Val Tyr Thr Leu Pro Pro Ser Arg
285                 290                 295                 300 gat gag ctg acc aag aac cag gtc agc ctg acc tgc ctg gtc aaa ggc      964
Asp Glu Leu Thr Lys Asn Gln Val Ser Leu Thr Cys Leu Val Lys Gly
                305                 310                 315 ttc tat ccc agc gac atc gcc gtg gag tgg gag agc aat ggg cag ccg     1012
Phe Tyr Pro Ser Asp Ile Ala Val Glu Trp Glu Ser Asn Gly Gln Pro
                320                 325                 330 gag aac aac tac aag acc acg cct ccc gtg ctg gac tcc gac ggc tcc     1060
Glu Asn Asn Tyr Lys Thr Thr Pro Pro Val Leu Asp Ser Asp Gly Ser
                335                 340                 345 ttc ttc ctc tac agc aag ctc acc gtg gac aag agc agg tgg cag cag     1108
Phe Phe Leu Tyr Ser Lys Leu Thr Val Asp Lys Ser Arg Trp Gln Gln
350                 355                 360 ggg aac gtc ttc tca tgc tcc gtg atg cat gag gct ctg cac aac cac     1156
Gly Asn Val Phe Ser Cys Ser Val Met His Glu Ala Leu His Asn His
365                 370                 375                 380 tac acg cag aag agc ctc tcc ctg tct ccg ggt aaa taatctagag          1202
Tyr Thr Gln Lys Ser Leu Ser Leu Ser Pro Gly Lys
                385                 390 gcgcgccaat ta                                                       1214

<210> SEQ ID NO 50
<211> LENGTH: 392
<212> TYPE: PRT
<213> ORGANISM: Homo sapiens

<400> SEQUENCE: 50

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Arg Gln Arg
        115                 120                 125

Ser Gly Glu Val Glu Asn Asn Ser Asp Asn Ser Gly Arg Tyr Gln Gly
130                 135                 140

Leu Glu His Arg Gly Ser Glu Ala Ser Pro Ala Leu Pro Gly Leu Lys
145                 150                 155                 160

Glu Pro Lys Ser Ser Asp Lys Thr His Thr Cys Pro Pro Cys Pro Ala
                165                 170                 175

Pro Glu Ala Glu Gly Ala Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
210                 215                 220
```

```
Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
            245                 250                 255

Asp Trp Leu Asn Gly Lys Glu Tyr Lys Cys Lys Val Ser Asn Lys Ala
            260                 265                 270

Leu Pro Ser Ser Ile Glu Lys Thr Ile Ser Lys Ala Lys Gly Gln Pro
            275                 280                 285

Arg Glu Pro Gln Val Tyr Thr Leu Pro Pro Ser Arg Asp Glu Leu Thr
290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
            325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
            355                 360                 365

Ser Cys Ser Val Met His Glu Ala Leu His Asn His Tyr Thr Gln Lys
370                 375                 380

Ser Leu Ser Leu Ser Pro Gly Lys
385                 390

<210> SEQ ID NO 51
<211> LENGTH: 1070
<212> TYPE: DNA
<213> ORGANISM: Homo sapiens
<220> FEATURE:
<221> NAME/KEY: CDS
<222> LOCATION: (17)...(1048)
<223> OTHER INFORMATION: coding sequence for fusion protein

<400> SEQUENCE: 51
tattaggccg gccacc atg gat gca atg aag aga ggg ctc tgc tgt gtg ctg        52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc         100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag         148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc         196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc         244
Asn His Gln Ser Gln Arg Thr Cys Ala Ala Phe Cys Arg Ser Leu Ser
                65                  70                  75 tgc cgc aag gag caa ggc aag ttc tat gac cat ctc ctg agg gac tgc         292
Cys Arg Lys Glu Gln Gly Lys Phe Tyr Asp His Leu Leu Arg Asp Cys
            80                  85                  90 atc agc tgt gcc tcc atc tgt gga cag cac cct aag caa tgt gca tac         340
Ile Ser Cys Ala Ser Ile Cys Gly Gln His Pro Lys Gln Cys Ala Tyr
        95                  100                 105 ttc tgt gag aac gag ccc aaa tct tca gac aaa act cac aca tgc cca         388
Phe Cys Glu Asn Glu Pro Lys Ser Ser Asp Lys Thr His Thr Cys Pro
    110                 115                 120 ccg tgc cca gca cct gaa gcc gag ggg gca ccg tca gtc ttc ctc ttc         436
```

```
Pro Cys Pro Ala Pro Glu Ala Glu Gly Ala Pro Ser Val Phe Leu Phe
125                 130                 135                 140 ccc cca aaa ccc aag gac acc ctc atg atc tcc cgg acc cct gag gtc        484
Pro Pro Lys Pro Lys Asp Thr Leu Met Ile Ser Arg Thr Pro Glu Val
                145                 150                 155 aca tgc gtg gtg gtg gac gtg agc cac gaa gac cct gag gtc aag ttc        532
Thr Cys Val Val Val Asp Val Ser His Glu Asp Pro Glu Val Lys Phe
            160                 165                 170 aac tgg tac gtg gac ggc gtg gag gtg cat aat gcc aag aca aag ccg        580
Asn Trp Tyr Val Asp Gly Val Glu Val His Asn Ala Lys Thr Lys Pro
        175                 180                 185 cgg gag gag cag tac aac agc acg tac cgt gtg gtc agc gtc ctc acc        628
Arg Glu Glu Gln Tyr Asn Ser Thr Tyr Arg Val Val Ser Val Leu Thr
    190                 195                 200 gtc ctg cac cag gac tgg ctg aat ggc aag gag tac aag tgc aag gtc        676
Val Leu His Gln Asp Trp Leu Asn Gly Lys Glu Tyr Lys Cys Lys Val
205                 210                 215                 220 tcc aac aaa gcc ctc cca tcc tcc atc gag aaa acc atc tcc aaa gcc        724
Ser Asn Lys Ala Leu Pro Ser Ser Ile Glu Lys Thr Ile Ser Lys Ala
                225                 230                 235 aaa ggg cag ccc cga gaa cca cag gtg tac acc ctg ccc cca tcc cgg        772
Lys Gly Gln Pro Arg Glu Pro Gln Val Tyr Thr Leu Pro Pro Ser Arg
            240                 245                 250 gat gag ctg acc aag aac cag gtc agc ctg acc tgc ctg gtc aaa ggc        820
Asp Glu Leu Thr Lys Asn Gln Val Ser Leu Thr Cys Leu Val Lys Gly
        255                 260                 265 ttc tat ccc agc gac atc gcc gtg gag tgg gag agc aat ggg cag ccg        868
Phe Tyr Pro Ser Asp Ile Ala Val Glu Trp Glu Ser Asn Gly Gln Pro
    270                 275                 280 gag aac aac tac aag acc acg cct ccc gtg ctg gac tcc gac ggc tcc        916
Glu Asn Asn Tyr Lys Thr Thr Pro Pro Val Leu Asp Ser Asp Gly Ser
285                 290                 295                 300 ttc ttc ctc tac agc aag ctc acc gtg gac aag agc agg tgg cag cag        964
Phe Phe Leu Tyr Ser Lys Leu Thr Val Asp Lys Ser Arg Trp Gln Gln
                305                 310                 315 ggg aac gtc ttc tca tgc tcc gtg atg cat gag gct ctg cac aac cac        1012
Gly Asn Val Phe Ser Cys Ser Val Met His Glu Ala Leu His Asn His
            320                 325                 330 tac acg cag aag agc ctc tcc ctg tct ccg ggt aaa taatctagag             1058
Tyr Thr Gln Lys Ser Leu Ser Leu Ser Pro Gly Lys
        335                 340 gcgcgccaat ta                                                          1070

<210> SEQ ID NO 52
<211> LENGTH: 344
<212> TYPE: PRT
<213> ORGANISM: Homo sapiens

<400> SEQUENCE: 52

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80
```

```
Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Glu Pro Lys Ser Ser Asp Lys Thr His Thr Cys Pro Pro Cys Pro Ala
        115                 120                 125

Pro Glu Ala Glu Gly Ala Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 53
<211> LENGTH: 1082
<212> TYPE: DNA
<213> ORGANISM: Homo sapiens
<220> FEATURE:
<221> NAME/KEY: CDS
<222> LOCATION: (17)...(1060)
<223> OTHER INFORMATION: coding sequence for fusion protein

<400> SEQUENCE: 53
tattaggccg gccacc atg gat gca atg aag aga ggg ctc tgc tgt gtg ctg        52
                Met Asp Ala Met Lys Arg Gly Leu Cys Cys Val Leu
                1               5                   10 ctg ctg tgt ggc gcc gtc ttc gtt tcg ctc agc cag gaa atc cat gcc        100
Leu Leu Cys Gly Ala Val Phe Val Ser Leu Ser Gln Glu Ile His Ala
            15                  20                  25 gag ttg aga cgc ttc cgt aga gct atg aga tcc tgc ccc gaa gag cag        148
Glu Leu Arg Arg Phe Arg Arg Ala Met Arg Ser Cys Pro Glu Glu Gln
        30                  35                  40 tac tgg gat cct ctg ctg ggt acc tgc atg tcc tgc aaa acc att tgc        196
Tyr Trp Asp Pro Leu Leu Gly Thr Cys Met Ser Cys Lys Thr Ile Cys
45                  50                  55                  60
```

```
aac cat cag agc cag cgc acc tgt gca gcc ttc tgc agg tca ctc agc    244
Asn His Gln Ser Gln Arg Thr Cys Ala Ala Phe Cys Arg Ser Leu Ser
             65                  70                  75 tgc cgc aag gag caa ggc aag ttc tat gac cat ctc ctg agg gac tgc    292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac    340
Ile Ser Cys Ala Ser Ile Cys Gly Gln His Pro Lys Gln Cys Ala Tyr
             95                 100                 105 ttc tgt gag aac aag ctc agg agc gag ccc aaa tct tca gac aaa act    388
Phe Cys Glu Asn Lys Leu Arg Ser Glu Pro Lys Ser Ser Asp Lys Thr
110                 115                 120 cac aca tgc cca ccg tgc cca gca cct gaa gcc gag ggg gca ccg tca    436
His Thr Cys Pro Pro Cys Pro Ala Pro Glu Ala Glu Gly Ala Pro Ser
125                 130                 135                 140 gtc ttc ctc ttc ccc cca aaa ccc aag gac acc ctc atg atc tcc cgg    484
Val Phe Leu Phe Pro Pro Lys Pro Lys Asp Thr Leu Met Ile Ser Arg
                145                 150                 155 acc cct gag gtc aca tgc gtg gtg gtg gac gtg agc cac gaa gac cct    532
Thr Pro Glu Val Thr Cys Val Val Val Asp Val Ser His Glu Asp Pro
            160                 165                 170 gag gtc aag ttc aac tgg tac gtg gac ggc gtg gag gtg cat aat gcc    580
Glu Val Lys Phe Asn Trp Tyr Val Asp Gly Val Glu Val His Asn Ala
        175                 180                 185 aag aca aag ccg cgg gag gag cag tac aac agc acg tac cgt gtg gtc    628
Lys Thr Lys Pro Arg Glu Glu Gln Tyr Asn Ser Thr Tyr Arg Val Val
    190                 195                 200 agc gtc ctc acc gtc ctg cac cag gac tgg ctg aat ggc aag gag tac    676
Ser Val Leu Thr Val Leu His Gln Asp Trp Leu Asn Gly Lys Glu Tyr
205                 210                 215                 220 aag tgc aag gtc tcc aac aaa gcc ctc cca tcc tcc atc gag aaa acc    724
Lys Cys Lys Val Ser Asn Lys Ala Leu Pro Ser Ser Ile Glu Lys Thr
                225                 230                 235 atc tcc aaa gcc aaa ggg cag ccc cga gaa cca cag gtg tac acc ctg    772
Ile Ser Lys Ala Lys Gly Gln Pro Arg Glu Pro Gln Val Tyr Thr Leu
            240                 245                 250 ccc cca tcc cgg gat gag ctg acc aag aac cag gtc agc ctg acc tgc    820
Pro Pro Ser Arg Asp Glu Leu Thr Lys Asn Gln Val Ser Leu Thr Cys
        255                 260                 265 ctg gtc aaa ggc ttc tat ccc agc gac atc gcc gtg gag tgg gag agc    868
Leu Val Lys Gly Phe Tyr Pro Ser Asp Ile Ala Val Glu Trp Glu Ser
    270                 275                 280 aat ggg cag ccg gag aac aac tac aag acc acg cct ccc gtg ctg gac    916
Asn Gly Gln Pro Glu Asn Asn Tyr Lys Thr Thr Pro Pro Val Leu Asp
285                 290                 295                 300 tcc gac ggc tcc ttc ttc ctc tac agc aag ctc acc gtg gac aag agc    964
Ser Asp Gly Ser Phe Phe Leu Tyr Ser Lys Leu Thr Val Asp Lys Ser
                305                 310                 315 agg tgg cag cag ggg aac gtc ttc tca tgc tcc gtg atg cat gag gct   1012
Arg Trp Gln Gln Gly Asn Val Phe Ser Cys Ser Val Met His Glu Ala
            320                 325                 330 ctg cac aac cac tac acg cag aag agc ctc tcc ctg tct ccg ggt aaa   1060
Leu His Asn His Tyr Thr Gln Lys Ser Leu Ser Leu Ser Pro Gly Lys
        335                 340                 345 taatctagag gcgcgccaat ta                                          1082

<210> SEQ ID NO 54
<211> LENGTH: 348
<212> TYPE: PRT
```

<213> ORGANISM: Homo sapiens
<220> FEATURE:
<223> OTHER INFORMATION: Fusion protein.

<400> SEQUENCE: 54

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
             20                  25                  30

Phe Arg Arg Ala Met Arg Ser Cys Pro Glu Glu Gln Tyr Trp Asp Pro
         35                  40                  45

Leu Leu Gly Thr Cys Met Ser Cys Lys Thr Ile Cys Asn His Gln Ser
     50                  55                  60

Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
             85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 55
<211> LENGTH: 1109
<212> TYPE: DNA
<213> ORGANISM: Homo sapiens
<220> FEATURE:
<221> NAME/KEY: CDS
<222> LOCATION: (17)...(1090)
<223> OTHER INFORMATION: coding sequence for fusion protein

<400> SEQUENCE: 55

```
tattaggccg gccacc atg gat gca atg aag aga ggg ctc tgc tgt gtg ctg        52
               Met Asp Ala Met Lys Arg Gly Leu Cys Cys Val Leu
                1               5                  10 ctg ctg tgt ggc gcc gtc ttc gtt tcg ctc agc cag gaa atc cat gcc         100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag         148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc         196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc         244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc         292
Cys Arg Lys Glu Gln Gly Lys Phe Tyr Asp His Leu Leu Arg Asp Cys
         80                  85                  90 atc agc tgt gcc tcc atc tgt gga cag cac cct aag caa tgt gca tac         340
Ile Ser Cys Ala Ser Ile Cys Gly Gln His Pro Lys Gln Cys Ala Tyr
     95                 100                 105 ttc tgt gag aac aag ctc agg agc cca gtg aac ctt cca cca gag ctc         388
Phe Cys Glu Asn Lys Leu Arg Ser Pro Val Asn Leu Pro Pro Glu Leu
110                 115                 120 agg gag ccc aaa tct tca gac aaa act cac aca tgc cca ccg tgc cca         436
Arg Glu Pro Lys Ser Ser Asp Lys Thr His Thr Cys Pro Pro Cys Pro
125                 130                 135                 140 gca cct gaa gcc gag ggg gca ccg tca gtc ttc ctc ttc ccc cca aaa         484
Ala Pro Glu Ala Glu Gly Ala Pro Ser Val Phe Leu Phe Pro Pro Lys
                145                 150                 155 ccc aag gac acc ctc atg atc tcc cgg acc cct gag gtc aca tgc gtg         532
Pro Lys Asp Thr Leu Met Ile Ser Arg Thr Pro Glu Val Thr Cys Val
        160                 165                 170 gtg gtg gac gtg agc cac gaa gac cct gag gtc aag ttc aac tgg tac         580
Val Val Asp Val Ser His Glu Asp Pro Glu Val Lys Phe Asn Trp Tyr
    175                 180                 185 gtg gac ggc gtg gag gtg cat aat gcc aag aca aag ccg cgg gag gag         628
Val Asp Gly Val Glu Val His Asn Ala Lys Thr Lys Pro Arg Glu Glu
190                 195                 200 cag tac aac agc acg tac cgt gtg gtc agc gtc ctc acc gtc ctg cac         676
Gln Tyr Asn Ser Thr Tyr Arg Val Val Ser Val Leu Thr Val Leu His
205                 210                 215                 220 cag gac tgg ctg aat ggc aag gag tac aag tgc aag gtc tcc aac aaa         724
Gln Asp Trp Leu Asn Gly Lys Glu Tyr Lys Cys Lys Val Ser Asn Lys
                225                 230                 235 gcc ctc cca tcc tcc atc gag aaa acc atc tcc aaa gcc aaa ggg cag         772
Ala Leu Pro Ser Ser Ile Glu Lys Thr Ile Ser Lys Ala Lys Gly Gln
        240                 245                 250 ccc cga gaa cca cag gtg tac acc ctg ccc cca tcc cgg gat gag ctg         820
Pro Arg Glu Pro Gln Val Tyr Thr Leu Pro Pro Ser Arg Asp Glu Leu
    255                 260                 265 acc aag aac cag gtc agc ctg acc tgc ctg gtc aaa ggc ttc tat ccc         868
Thr Lys Asn Gln Val Ser Leu Thr Cys Leu Val Lys Gly Phe Tyr Pro
270                 275                 280 agc gac atc gcc gtg gag tgg gag agc aat ggg cag ccg gag aac aac         916
Ser Asp Ile Ala Val Glu Trp Glu Ser Asn Gly Gln Pro Glu Asn Asn
```

```
                     285                 290                 295                 300
tac aag acc acg cct ccc gtg ctg gac tcc gac ggc tcc ttc ttc ctc      964
Tyr Lys Thr Thr Pro Pro Val Leu Asp Ser Asp Gly Ser Phe Phe Leu
                305                 310                 315 tac agc aag ctc acc gtg gac aag agc agg tgg cag cag ggg aac gtc     1012
Tyr Ser Lys Leu Thr Val Asp Lys Ser Arg Trp Gln Gln Gly Asn Val
            320                 325                 330 ttc tca tgc tcc gtg atg cat gag gct ctg cac aac cac tac acg cag    1060
Phe Ser Cys Ser Val Met His Glu Ala Leu His Asn His Tyr Thr Gln
        335                 340                 345 aag agc ctc tcc ctg tct ccg ggt aaa taa tctagaggcg cgccaatta        1109
Lys Ser Leu Ser Leu Ser Pro Gly Lys *
    350                 355

<210> SEQ ID NO 56
<211> LENGTH: 357
<212> TYPE: PRT
<213> ORGANISM: Homo sapiens

<400> SEQUENCE: 56

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Glu Pro Lys
        115                 120                 125

Ser Ser Asp Lys Thr His Thr Cys Pro Pro Cys Pro Ala Pro Glu Ala
    130                 135                 140

Glu Gly Ala Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ser
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285
```

Val Glu Trp Glu Ser Asn Gly Gln Pro Glu Asn Asn Tyr Lys Thr Thr
     290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 57
<211> LENGTH: 9
<212> TYPE: DNA
<213> ORGANISM: Homo sapiens
<220> FEATURE:
<223> OTHER INFORMATION: Illustrative nucleotide sequence.

<400> SEQUENCE: 57 atgcacggg                                                                 9

<210> SEQ ID NO 58
<211> LENGTH: 9
<212> TYPE: DNA
<213> ORGANISM: Homo sapiens
<220> FEATURE:
<223> OTHER INFORMATION: Illustrative nucleotide sequence.

<400> SEQUENCE: 58 cccgtgcat                                                                 9

<210> SEQ ID NO 59
<211> LENGTH: 586
<212> TYPE: DNA
<213> ORGANISM: Homo sapiens
<220> FEATURE:
<221> NAME/KEY: CDS
<222> LOCATION: (27)...(578)

<400> SEQUENCE: 59
gcagcttgtg cggcggcgtc ggcacc atg agg cga ggg ccc cgg agc ctg cgg      53
                              Met Arg Arg Gly Pro Arg Ser Leu Arg
                               1               5 ggc agg gac gcg cca gcc ccc acg ccc tgc gtc ccg gcc gag tgc ttc      101
Gly Arg Asp Ala Pro Ala Pro Thr Pro Cys Val Pro Ala Glu Cys Phe
 10                  15                  20                  25 gac ctg ctg gtc cgc cac tgc gtg gcc tgc ggg ctc ctg cgc acg ccg      149
Asp Leu Leu Val Arg His Cys Val Ala Cys Gly Leu Leu Arg Thr Pro
                 30                  35                  40 cgg ccg aaa ccg gcc ggg gcc agc agc cct gcg ccc agg acg gcg ctg      197
Arg Pro Lys Pro Ala Gly Ala Ser Ser Pro Ala Pro Arg Thr Ala Leu
             45                  50                  55 cag ccg cag gag tcg gtg ggc gcg ggg gcc ggc gag gcg gcg ctg ccc      245
Gln Pro Gln Glu Ser Val Gly Ala Gly Ala Gly Glu Ala Ala Leu Pro
         60                  65                  70 ctg ccc ggg ctg ctc ttt ggc gcc ccc gcg ctg ctg ggc ctg gca ctg      293
Leu Pro Gly Leu Leu Phe Gly Ala Pro Ala Leu Leu Gly Leu Ala Leu
     75                  80                  85 gtc ctg gcg ctg gtc ctg gtg ggt ctg gtg agc tgg agg cgg cga cag      341
Val Leu Ala Leu Val Leu Val Gly Leu Val Ser Trp Arg Arg Arg Gln
 90                  95                 100                 105

```
cgg cgg ctt cgc ggc gcg tcc tcc gca gag gcc ccc gac gga gac aag    389
Arg Arg Leu Arg Gly Ala Ser Ser Ala Glu Ala Pro Asp Gly Asp Lys
            110                 115                 120 gac gcc cca gag ccc ctg gac aag gtc atc att ctg tct ccg gga atc    437
Asp Ala Pro Glu Pro Leu Asp Lys Val Ile Ile Leu Ser Pro Gly Ile
        125                 130                 135 tct gat gcc aca gct cct gcc tgg cct cct cct ggg gaa gac cca gga    485
Ser Asp Ala Thr Ala Pro Ala Trp Pro Pro Pro Gly Glu Asp Pro Gly
            140                 145                 150 acc acc cca cct ggc cac agt gtc cct gtg cca gcc aca gag ctg ggc    533
Thr Thr Pro Pro Gly His Ser Val Pro Val Pro Ala Thr Glu Leu Gly
        155                 160                 165 tcc act gaa ctg gtg acc acc aag acg gcc ggc cct gag caa caa        578
Ser Thr Glu Leu Val Thr Thr Lys Thr Ala Gly Pro Glu Gln Gln
170                 175                 180 tagcaggg                                                            586

<210> SEQ ID NO 60
<211> LENGTH: 184
<212> TYPE: PRT
<213> ORGANISM: Homo sapiens

<400> SEQUENCE: 60

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 61
<211> LENGTH: 19
<212> TYPE: PRT
<213> ORGANISM: Homo sapiens
<220> FEATURE:
<223> OTHER INFORMATION: 26-10 VH signal sequence.

<400> SEQUENCE: 61

Met Gly Trp Ser Trp Ile Phe Leu Phe Leu Leu Ser Gly Thr Ala Gly
1               5                   10                  15
```

-continued

```
Val Leu Ser

<210> SEQ ID NO 62
<211> LENGTH: 332
<212> TYPE: PRT
<213> ORGANISM: Homo sapiens
<220> FEATURE:
<223> OTHER INFORMATION: Fusion protein.

<400> SEQUENCE: 62

Met Gly Trp Ser Trp Ile Phe Leu Phe Leu Leu Ser Gly Thr Ala Gly
 1               5                  10                  15

Val Leu Ser Ala Met Arg Ser Cys Pro Glu Glu Gln Tyr Trp Asp Pro
            20                  25                  30

Leu Leu Gly Thr Cys Met Ser Cys Lys Thr Ile Cys Asn His Gln Ser
        35                  40                  45

Gln Arg Thr Cys Ala Ala Phe Cys Arg Ser Leu Ser Cys Arg Lys Glu
    50                  55                  60

Gln Gly Lys Phe Tyr Asp His Leu Leu Arg Asp Cys Ile Ser Cys Ala
65                  70                  75                  80

Ser Ile Cys Gly Gln His Pro Lys Gln Cys Ala Tyr Phe Cys Glu Asn
                85                  90                  95

Lys Leu Arg Ser Glu Pro Lys Ser Ser Asp Lys Thr His Thr Cys Pro
            100                 105                 110

Pro Cys Pro Ala Pro Glu Ala Glu Gly Ala Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ser Ser Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 63
<211> LENGTH: 51
<212> TYPE: DNA
```

<213> ORGANISM: Homo sapiens
<220> FEATURE:
<223> OTHER INFORMATION: 26-10 VH 5' UTR.

<400> SEQUENCE: 63
aacatatgtc caatgtcctc tccacagaca ctgaacacac tgactccaac g    51

<210> SEQ ID NO 64
<211> LENGTH: 51
<212> TYPE: DNA
<213> ORGANISM: Homo sapiens
<220> FEATURE:
<223> OTHER INFORMATION: Modified 26-10 VH 5' UTR.

<400> SEQUENCE: 64
aacatatgtc caatgtcctc tccacagaca ctgaacacac tgactgccac c    51

<210> SEQ ID NO 65
<211> LENGTH: 57
<212> TYPE: DNA
<213> ORGANISM: Homo sapiens
<220> FEATURE:
<221> NAME/KEY: CDS
<222> LOCATION: (1)...(57)
<223> OTHER INFORMATION: 26-10 VH signal sequence.

<400> SEQUENCE: 65 atg gga tgg agc tgg atc ttt ctc ttt ctt ctg tca gga act gca ggt    48
Met Gly Trp Ser Trp Ile Phe Leu Phe Leu Leu Ser Gly Thr Ala Gly
 1               5                  10                  15 gtc ctc tct                                                        57
Val Leu Ser <210> SEQ ID NO 66
<211> LENGTH: 84
<212> TYPE: DNA
<213> ORGANISM: Homo sapiens
<220> FEATURE:
<223> OTHER INFORMATION: 26-10 VH intron.

<400> SEQUENCE: 66 gtaagggct ccccagttcc aaaatctgaa gaaagaaat ggcttgggat gtcacagata    60
tccactctgt ctttctcttc acag                                        84

<210> SEQ ID NO 67
<211> LENGTH: 1135
<212> TYPE: DNA
<213> ORGANISM: Homo sapiens
<220> FEATURE:
<223> OTHER INFORMATION: Fusion protein.

<400> SEQUENCE: 67
aacatatgtc caatgtcctc tccacagaca ctgaacacac tgactccaac gatgggatgg    60
agctggatct ttctctttct tctgtcagga actgcaggta aggggctccc cagttccaaa   120
atctgaagaa agaaatggc ttgggatgtc acagatatcc actctgtctt tctcttcaca   180
ggtgtcctct ctgctatgag atcctgcccc gaagagcagt actgggatcc tctgctgggt   240
acctgcatgt cctgcaaaac catttgcaac catcagagcc agcgcacctg tgcagccttc   300
tgcaggtcac tcagctgccg caaggagcaa ggcaagttct atgaccatct cctgagggac   360
tgcatcagct gtgcctccat ctgtggacag cacctaagc aatgtgcata cttctgtgag   420
aacaagctca ggagcgagcc caaatcttca gacaaaactc acacatgccc accgtgccca   480

-continued

| | |
|---|---|
| gcacctgaag ccgagggggc accgtcagtc ttcctcttcc ccccaaaacc caaggacacc | 540 |
| ctcatgatct cccggacccc tgaggtcaca tgcgtggtgg tggacgtgag ccacgaagac | 600 |
| cctgaggtca agttcaactg gtacgtggac ggcgtggagg tgcataatgc caagacaaag | 660 |
| ccgcgggagg agcagtacaa cagcacgtac cgtgtggtca gcgtcctcac cgtcctgcac | 720 |
| caggactggc tgaatggcaa ggagtacaag tgcaaggtct ccaacaaagc cctcccatcc | 780 |
| tccatcgaga aaaccatctc caaagccaaa gggcagcccc gagaaccaca ggtgtacacc | 840 |
| ctgcccccat cccgggatga gctgaccaag aaccaggtca gcctgacctg cctggtcaaa | 900 |
| ggcttctatc ccagcgacat cgccgtggag tgggagagca atgggcagcc ggagaacaac | 960 |
| tacaagacca cgcctcccgt gctggactcc gacggctcct tcttcctcta cagcaagctc | 1020 |
| accgtggaca agagcaggtg gcagcagggg aacgtcttct catgctccgt gatgcatgag | 1080 |
| gctctgcaca accactacac gcagaagagc ctctccctgt ctccgggtaa ataaa | 1135 |

<210> SEQ ID NO 68
<211> LENGTH: 1135
<212> TYPE: DNA
<213> ORGANISM: Homo sapiens
<220> FEATURE:
<223> OTHER INFORMATION: Fusion protein.

<400> SEQUENCE: 68

| | |
|---|---|
| aacatatgtc caatgtcctc tccacagaca ctgaacacac tgactgccac catgggatgg | 60 |
| agctggatct ttctctttct tctgtcagga actgcaggta aggggctccc cagttccaaa | 120 |
| atctgaagaa aagaaatggc ttgggatgtc acagatatcc actctgtctt tctcttcaca | 180 |
| ggtgtcctct ctgctatgag atcctgcccc gaagagcagt actgggatcc tctgctgggt | 240 |
| acctgcatgt cctgcaaaac catttgcaac catcagagcc agcgcacctg tgcagccttc | 300 |
| tgcaggtcac tcagctgccg caaggagcaa ggcaagttct atgaccatct cctgagggac | 360 |
| tgcatcagct gtgcctccat ctgtggacag caccctaagc aatgtgcata cttctgtgag | 420 |
| aacaagctca ggagcgagcc caaatcttca gacaaaactc acacatgccc accgtgccca | 480 |
| gcacctgaag ccgagggggc accgtcagtc ttcctcttcc ccccaaaacc caaggacacc | 540 |
| ctcatgatct cccggacccc tgaggtcaca tgcgtggtgg tggacgtgag ccacgaagac | 600 |
| cctgaggtca agttcaactg gtacgtggac ggcgtggagg tgcataatgc caagacaaag | 660 |
| ccgcgggagg agcagtacaa cagcacgtac cgtgtggtca gcgtcctcac cgtcctgcac | 720 |
| caggactggc tgaatggcaa ggagtacaag tgcaaggtct ccaacaaagc cctcccatcc | 780 |
| tccatcgaga aaaccatctc caaagccaaa gggcagcccc gagaaccaca ggtgtacacc | 840 |
| ctgcccccat cccgggatga gctgaccaag aaccaggtca gcctgacctg cctggtcaaa | 900 |
| ggcttctatc ccagcgacat cgccgtggag tgggagagca atgggcagcc ggagaacaac | 960 |
| tacaagacca cgcctcccgt gctggactcc gacggctcct tcttcctcta cagcaagctc | 1020 |
| accgtggaca agagcaggtg gcagcagggg aacgtcttct catgctccgt gatgcatgag | 1080 |
| gctctgcaca accactacac gcagaagagc ctctccctgt ctccgggtaa ataaa | 1135 |

<210> SEQ ID NO 69
<211> LENGTH: 884
<212> TYPE: DNA
<213> ORGANISM: Homo sapiens
<220> FEATURE:
<223> OTHER INFORMATION: CMV enhancer/MPSV LTR promoter construct.

<400> SEQUENCE: 69

-continued

```
cgcgttacat aacttacggt aaatggcccg cctggctgac cgcccaacga cccccgccca      60
ttgacgtcaa taatgacgta tgttcccata gtaacgccaa tagggacttt ccattgacgt     120
caatgggtgg agtatttacg gtaaactgcc cacttggcag tacatcaagt gtatcatatg     180
ccaagtacgc ccccctattga cgtcaatgac ggtaaatggc ccgcctggca ttatgcccag    240
tacatgacct tatgggactt tcctacttgg cagtacatct acgtattagt catcgctatt     300
accatggtga tgcggttttg gcagtacatc aatgggcgtg gatagcggtt tgactcacgg    360
ggatttccaa gtctccaccc cattgacgtc aatgggagtt tgttttgaat gaaagacccc    420
acctgtaggt ttggcaagct agcttaagta acgccatttg caaggcatgg aaaaatacat    480
aactgagaat agagaagttc agatcaaggt caggaacaga gaaacaggag aatatgggcc    540
aaacaggata tctgtggtaa gcagttcctg ccccgctcag ggccaagaac agttggaaca    600
ggagaatatg gcccaaacag gatatctgtg gtaagcagtt cctgccccgc tcagggccaa    660
gaacagatgg tccccagatc ggtcccgccc tcagcagttt ctagagaacc atcagatgtt    720
tccagggtgc cccaaggacc tgaaatgacc ctgtgcctta tttgaactaa ccaatcagtt    780
cgcttctcgc ttctgttcgc gcgcttctgc tccccgagct caataaaaga gcccacaacc    840
cctcactcgg cgcgccagtc ctccgataga ctgcgtcgcc cggg                     884
```

<210> SEQ ID NO 70
<211> LENGTH: 455
<212> TYPE: DNA
<213> ORGANISM: Homo sapiens
<220> FEATURE:
<223> OTHER INFORMATION: MPSV LTR promoter without the negative control
      region.

<400> SEQUENCE: 70

```
aatgaaagac cccacctgta ggtttggcaa gctagaaggt taggaacaga gagacagcag      60
aatatgggcc aaacaggata tctgtggtaa gcagttcctg ccccggctca gggccaagaa    120
cagatggtcc ccagatgcgg tcccgccctc agcagtttct agagaaccat cagatgtttc    180
cagggtgccc caaggacctg aaaatgaccc tgtgccttat ttgaactaac caatcagttc    240
gcttctcgct tctgttcgcg cgcttctgct ccccgagctc aataaaagag cccacaaccc    300
ctcactcggc gcgccagtcc tccgatagac tgcgtcgccc gggtacccgt gttctcaata    360
aaccctcttg cagttgcatc cgactcgtgg tctcgctgtt ccttgggagg gtctcctctg    420
agtgattgac tacccgtcag cggggtctt tcagt                               455
```

METHOD OF INHIBITING THE PROLIFERATION OF B CELL CANCERS USING TACI-IMMUNOGLOBULIN FUSION PROTEINS

CROSS-REFERENCE TO RELATED APPLICATIONS

This application is a continuation of U.S. application Ser. No. 12/359,801, filed Jan. 26, 2009, now U.S. Pat. No. 7,635,767, which is a divisional of U.S. application Ser. No. 11/242,294, filed Oct. 3, 2005, now U.S. Pat. No. 7,501,497, which is a continuation of U.S. application Ser. No. 10/152,363, now abandoned, filed May 20, 2002, which claims the benefit of U.S. Provisional Application Ser. No. 60/293,343, filed May 24, 2001, each of which are herein incorporated by reference.

TECHNICAL FIELD

The present invention relates generally to improved fusion proteins comprising a tumor necrosis factor receptor moiety and an immunoglobulin moiety. In particular, the present invention relates to improved TACI-immunoglobulin fusion proteins.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 381096seqlist-.txt, a creation date of Oct. 23, 2009, and a size of 104 Kb. The sequence listing filed via EFS-Web is part of the specification and is hereby incorporated in its entirety by reference herein.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783 (1990); Mosmann, *Curr. Opin. Immunol.* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the type II cytokine receptor family, based upon a characteristic 200 residue extracellular domain.

Cellular interactions, which occur during an immune response, are regulated by members of several families of cell surface receptors, including the tumor necrosis factor receptor (TNFR) family. The TNFR family consists of a number of integral membrane glycoprotein receptors many of which, in conjunction with their respective ligands, regulate interactions between different hematopoietic cell lineages (see, for example, Cosman, *Stem Cells* 12:440 (1994); Wajant et al., *Cytokine Growth Factor Rev.* 10:15 (1999); Yeh et al., *Immunol. Rev.* 169:283 (1999); Idriss and Naismith, *Microsc. Res. Tech.* 50:184 (2000)).

One such receptor is TACI, transmembrane activator and CAML-interactor (von Büllow and Bram, *Science* 228:138 (1997); Bram and von Büllow, U.S. Pat. No. 5,969,102 (1999)). TACI is a membrane bound receptor, which has an extracellular domain containing two cysteine-rich pseudo-repeats, a transmembrane domain and a cytoplasmic domain that interacts with CAML (calcium-modulator and cyclophilin ligand), an integral membrane protein located at intracellular vesicles which is a co-inducer of NF-AT activation when overexpressed in Jurkat cells. TACI is associated with B cells and a subset of T cells. Nucleotide sequences that encode TACI and its corresponding amino acid sequence are provided herein as SEQ ID NOs: 1 and 2, respectively The TACI receptor binds two members of the tumor necrosis factor (TNF) ligand family. One ligand is variously designated as ZTNF4, "BAFF," "neutrokine-α," "BLyS," "TALL-1," and "THANK" (Yu et al., international publication No. WO98/18921 (1998), Moore et al., *Science* 285:269 (1999); Mukhopadhyay et al., *J. Biol. Chem.* 274:15978 (1999); Schneider et al., *J. Exp. Med.* 189:1747 (1999); Shu et al., *J. Leukoc. Biol.* 65:680 (1999)). The amino acid sequence of ZTNF4 is provided as SEQ ID NO:3. The other ligand has been designated as "ZTNF2," "APRIL" and "TNRF death ligand-1" (Hahne et al., *J. Exp. Med.* 188:1185 (1998); Kelly et al., *Cancer Res.* 60:1021 (2000)). The amino acid sequence of ZTNF2 is provided as SEQ ID NO:4. Both ligands are also bound by the B-cell maturation receptor (BCMA) (Gross et al., *Nature* 404:995 (2000)). The nucleotide and amino acid sequence of BCMA are provided as SEQ ID NO:26 and SEQ ID NO:27, respectively.

The demonstrated in vivo activities of tumor necrosis factor receptors illustrate the clinical potential of soluble forms of the receptor. Soluble forms of the TACI receptor have been generated as immunoglobulin fusion proteins. Initial versions resulted in low-expressing, heterogeneous protein. The heterogeneity was observed at the TACI amino terminus, at the Fc carboxyl terminus, and in the TACI stalk region. A need therefore exists for pharmaceutically useful TACI receptor compositions.

BRIEF SUMMARY OF THE INVENTION

The present invention provides improved TACI-immunoglobulin fusion proteins suitable as therapeutic compounds.

BRIEF DESCRIPTION OF THE DRAWINGS

FIG. 1 shows the amino acid sequence of human TACI (SEQ ID NO:2). The locations of the cysteine-rich pseudo-repeats are indicated by shading, the transmembrane domain is boxed, and the stalk region is indicated by hash marks.

FIGS. 3A, 3B, 3C, and 3D show a comparison of the wild-type human γ1 constant region Fc amino acid sequence (SEQ ID NO:6) with variants Fc-488, Fc4, Fc5, Fc6, Fc7, and Fc8. The CH1 domain of the human γ1 constant region is not part of the Fc and is therefore not shown. The location of the hinge region, the $C_{H2}$, and the $C_{H3}$ domains are indicated. The Cys residues normally involved in disulfide bonding to the light chain constant region (LC) and heavy chain constant region (HC) are indicated. A "." symbol indicates identity to wild-type at that position, while "***" indicates the location of the carboxyl terminus, and illustrates the difference in the carboxyl terminus of Fc6 relative to the other Fc versions. Amino acid locations are indicated by EU index positions.

DETAILED DESCRIPTION OF THE INVENTION

1. Overview

Figure 2:
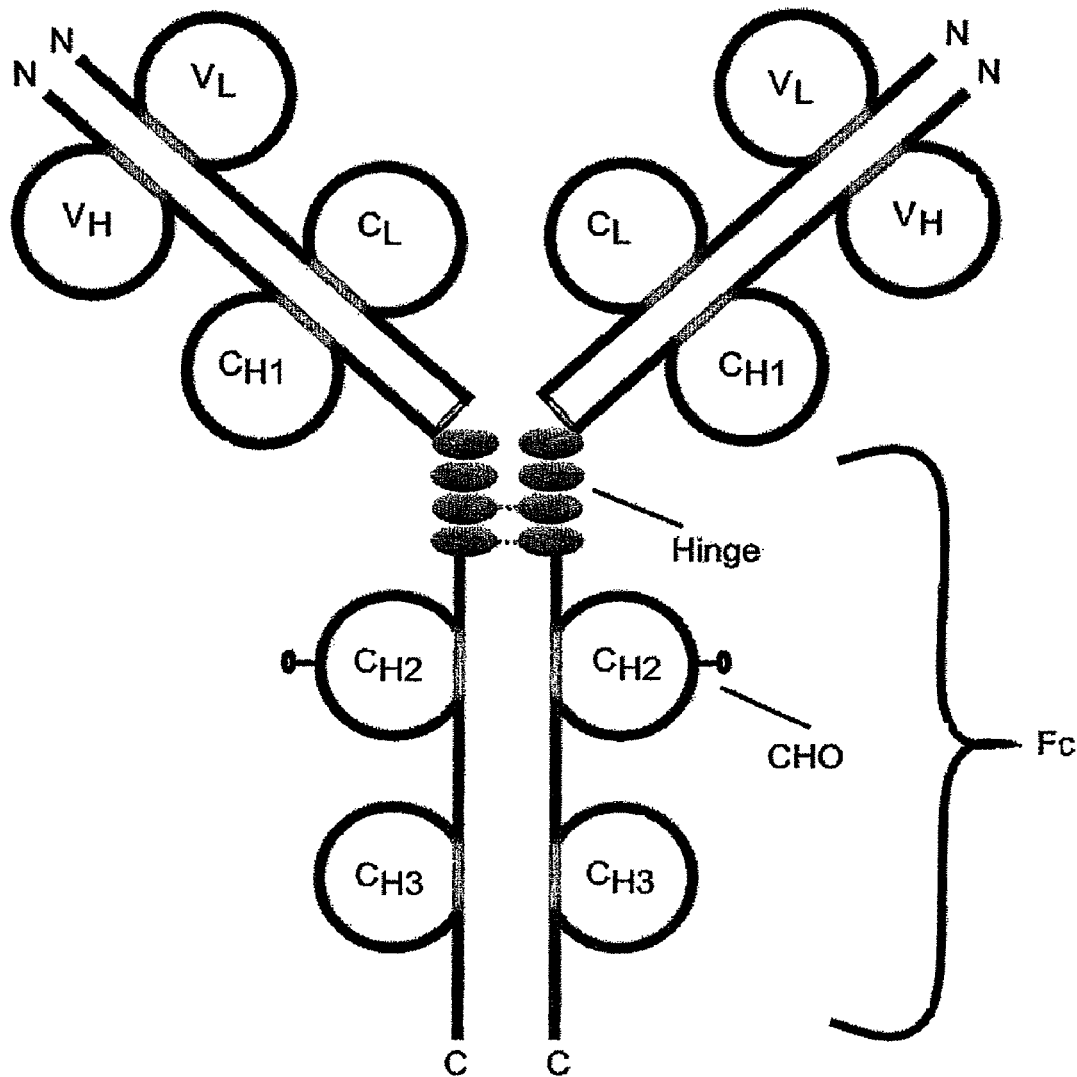
FIG. 2 is a schematic diagram of an immunoglobulin of the IgG1 subclass. $C_L$: light chain constant region; $C_{H1}$, $C_{H2}$, $C_{H3}$: heavy chain constant regions; $V_L$: light chain variable region; $V_H$: heavy chain variable region; CHO: carbohydrate; N: amino terminus; C: carboxyl terminus.

As described below, the present invention provides transmembrane activator and calcium modulator and cyclophilin ligand-interactor (TACI)-immunoglobulin fusion proteins, and methods for using TACI-immunoglobulin fusion proteins. For example, the present invention provides methods for inhibiting the proliferation of tumor cells, comprising administering to the tumor cells a composition that comprises a TACI-immunoglobulin fusion protein. Such a composition can be administered to cells cultured in vitro. Alternatively, the composition can be a pharmaceutical composition that comprises a pharmaceutically acceptable carrier and a TACI-immunoglobulin fusion protein, and the pharmaceutical composition can be administered to a subject, which has a tumor. The subject may be a mammalian subject. Administration of the pharmaceutical composition can inhibit, for example, the proliferation of B lymphocytes in a mammalian subject.

The present invention also provides methods for inhibiting ZTNF4 activity in a mammal, comprising administering to the mammal a composition that comprises a TACI-immunoglobulin. The ZTNF4 activity can be associated with various diseases and disorders. For example, a pharmaceutical composition that comprises a TACI-immunoglobulin fusion protein can be used to treat an autoimmune disease, such as systemic lupus erythematosus, myasthenia gravis, multiple sclerosis, insulin dependent diabetes mellitus, Crohn's disease, rheumatoid arthritis, polyarticular-course juvenile rheumatoid arthritis, and psoriatic arthritis. Alternatively, a pharmaceutical composition that comprises a TACI-immunoglobulin can be used to treat a disorder such as asthma, bronchitis, emphysema, and end stage renal failure. A pharmaceutical composition comprising a TACI-immunoglobulin can also be used to treat renal disease, such as glomerulonephritis, vasculitis, nephritis, amyloidosis, and pyelonephritis, or a disorder, such as neoplasm, chronic lymphocytic leukemia, multiple myeloma, non-Hodgkin's lymphoma, post-transplantation lymphoproliferative disease, and light chain gammopathy. In certain cases, the ZTNF4 activity can be associated with T cells. A pharmaceutical composition that comprises a TACI-immunoglobulin can also be used to treat a disease or disorder associated with immunosuppression, graft rejection, graft versus host disease, and inflammation. For example, a pharmaceutical composition that comprises a TACT-immunoglobulin can be used to decrease inflammation, and to treat disorders such as joint pain, swelling, anemia, and septic shock.

The present invention also provides methods for reducing circulating blood levels of ZTNF4 in a mammalian subject, comprising administering to the mammalian subject a pharmaceutical composition that comprises a pharmaceutically acceptable carrier and a TACI-immunoglobulin fusion protein, wherein administration of the pharmaceutical composition reduces the circulating level of ZTNF4 in the blood of the mammalian subject. As an illustration, the administration of such a pharmaceutical composition can reduce circulating blood levels of ZTNF4 by at least 10%, by at least 20%, by at least 10 to 60%, by at least 20 to 50%, or by at least 30 to 40%, compared with the blood level of ZTNF4 prior to the administration of the pharmaceutical composition. Those of skill in the art can measure circulating levels of ZTNF4. Illustrative methods are described in Example 4 and Example 5.

As described below, illustrative TACI-immunoglobulin fusion proteins comprise:

(a) a TACI receptor moiety that consists of a fragment of a polypeptide that has the amino acid sequence of amino acid residues 30 to 154 of SEQ ID NO:2, wherein the TACI receptor moiety comprises at least one of (i) amino acid residues 34 to 66 of SEQ ID NO:2, and (ii) amino acid residues 71 to 104 of SEQ ID NO:2, and wherein the TACI receptor moiety binds at least one of ZTNF2 or ZTNF4, and (b) an immunoglobulin moiety comprising a constant region of an immunoglobulin.

Suitable TACI receptor moieties include: polypeptides that comprise amino acid residues 34 to 66 of SEQ ID NO:2, and amino acid residues 71 to 104 of SEQ ID NO:2; polypeptides that comprise amino acid residues 34 to 104 of SEQ ID NO:2; polypeptides that comprise the amino acid sequence of amino acid residues 30 to 110 of SEQ ID NO:2; and polypeptides that have an amino acid sequence consisting of amino acid residues 30 to 110 of SEQ ID NO:2.

The immunoglobulin moiety of a TACI-immunoglobulin fusion protein can comprise a heavy chain constant region, such as a human heavy chain constant region. An IgG1 heavy chain constant region is one example of a suitable heavy chain constant region. An illustrative IgG1 heavy chain constant region is an IgG1 Fc fragment that comprises $C_{H2}$, and $C_{H3}$ domains. The IgG1 Fc fragment can be a wild-type IgG1 Fc fragment or a mutated IgG1 Fc fragment, such as the Fc fragment comprising the amino acid sequence of SEQ ID NO:33. One exemplary TACI-immunoglobulin fusion protein is a protein that has an amino acid sequence comprising the amino acid sequence of SEQ ID NO:54.

The TACI-immunoglobulin fusion proteins described herein can be multimers, such as dimers.

The present invention also provides nucleic acid molecules that encode a TACI-immunoglobulin fusion protein. An illustrative nucleotide sequence that encodes a TACI-immunoglobulin fusion protein is provided by SEQ ID NO:53.

The present invention also includes TACI soluble receptors that consist of a fragment of a polypeptide that has the amino acid sequence of amino acid residues 30 to 154 of SEQ ID NO:2, wherein the TACI soluble receptor comprises at least one of (i) amino acid residues 34 to 66 of SEQ ID NO:2, and (ii) amino acid residues 71 to 104 of SEQ ID NO:2, and wherein the TACI soluble receptor binds at least one of ZTNF2 or ZTNF4. Additional TACI soluble receptors are described herein as suitable TACI receptor moieties for TACI-immunoglobulin fusion proteins. Moreover, TACI soluble receptors can be used in methods described for TACI-immunoglobulin fusion proteins.

These and other aspects of the invention will become evident upon reference to the following detailed description and drawings. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' (SEQ ID NO:57) is complementary to 5' CCCGTGCAT 3' (SEQ ID NO:58).

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces a TACI-Fc fusion protein from an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a TACT-immunoglobulin fusion protein comprises a TACI receptor moiety and an immunoglobulin moiety. As used herein, a "TACI receptor moiety" is a portion of the extracellular domain of the TACI receptor that binds at least one of ZTNF2 or ZTNF4. The phrase an "immunoglobulin moiety" refers to a polypeptide that comprises a constant region of an immunoglobulin. For example, the immunoglobulin moiety can comprise a heavy chain constant region. The term "TACI-Fc" fusion protein refers to a TACI-immunoglobulin fusion protein in which the immunoglobulin moiety comprises immunoglobulin heavy chain constant regions, $C_{H2}$ and $C_{H3}$.

The term "receptor" denotes a cell-associated protein that binds to a bioactive molecule termed a "ligand." This interaction mediates the effect of the ligand on the cell. In the context of TACI receptor binding, the phrase "specifically binds" or "specific binding" refers to the ability of the ligand to competitively bind with the receptor. For example, ZTNF4 specifically binds with the TACI receptor, and this can be shown by observing competition for the TACI receptor between detectably labeled ZTNF4 and unlabeled ZTNF4.

Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity less than $10^9$ $M^{-1}$.

An "antibody fragment" is a portion of an antibody such as $F(ab')_2$, $F(ab)_2$, Fab', Fab, and the like. Regardless of structure, an antibody fragment binds with the same antigen that is recognized by the intact antibody.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom, which is conjugated to an antibody moiety to produce a conjugate, which is useful for therapy. Examples of therapeutic agents include drugs, toxins, immunomodulators, chelators, boron compounds, photoactive agents or dyes, and radioisotopes.

A "detectable label" is a molecule or atom, which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell, which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "antisense gene." Anti-sense RNA molecules are capable of binding to mRNA molecules, resulting in an inhibition of mRNA translation.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Nucleic Acid Molecules Encoding TACI-Immunoglobulin Proteins FIG. 1 provides the predicted amino acid sequence of human TACI (von Billow and Bram, Science 278:138 (1997)). The TACI polypeptide contains the following predicted elements: (a) two cysteine-rich pseudo-repeat structures characteristic of tumor necrosis factor ligand binding domains, (b) a 62 amino acid "stalk region," which resides between the ligand binding domains and the transmembrane domain, (c) a 20 amino acid transmembrane domain, and (d) a 127 amino acid intracellular domain. The amino acid sequence does not contain a predicted hydrophobic amino terminal signal sequence.

In order to create a soluble form of human TACI for use as an inhibitor of the native ligand:native receptor interaction, a TACI extracellular domain—human immunoglobulin Fc fusion protein was generated. The available human TACI sequence was used as the starting point for designing the fusion protein molecule (von Billow and Bram, Science 278: 138 (1997)). This initial construct, designated as "TACI-Fc4," included amino acid residues 1 through 154 of the TACI polypeptide, and a modified human Fc region, described below. The fusion point of residue 154 was chosen in order to include as much of the stalk region of TACI as possible while not including any potential portion of the predicted transmembrane domain.

Since native TACI polypeptide does not contain an amino terminal signal sequence, an amino terminal signal sequence was added to TACI in order to generate a secreted form of the TACI-Fc fusion protein. The signal sequence was a modified pre-pro sequence from human tissue plasminogen activator. The modifications were included to enhance signal peptidase cleavage and furin protease-specific processing and for that reason this sequence has been referred to as the "optimized tPA (otPA) leader." The otPA sequence (SEQ ID NO:25) is illustrated below; modified amino acid residues are shaded. The recombinant TACI-Fc fusion protein coding sequence was inserted into an expression vector, which was transfected into Chinese hamster ovary cells.

human IgG Fc antisera revealed two bands, one band was smaller than the expected size of approximately 48 kDa. Amino acid sequence analysis of purified proteins revealed that the smaller band reflected cleavage of TACI fusion proteins at various sites within the TACI stalk region. With reference to SEQ ID NO:2, the major termini were found at amino acid residues 118 and 123, although, proteins were also cleaved at amino acid positions 110, 139, and 141.

In addition to heterogeneity caused by cleavage in the stalk region, heterogeneity was also observed at the amino and carboxyl termini. With reference to SEQ ID NO:2, the major amino termini were found at amino acid residues 1, 10, and 13. Differences in the carboxyl terminus reflect the natural heterogeneity of recombinant immunoglobulins and immunoglobulin fusion proteins, which includes the incomplete removal of the carboxyl-terminally-encoded lysine residue. Another source of heterogeneity was found in the variable nature of the carbohydrate structure attached to the Fc encoded immunoglobulin $C_{H2}$ domain.

New versions of TACI-Fc were generated to address the observed heterogeneity. Constructs were designed that included at least one of the following variations in the TACI moiety: (1) portions of the TACI stalk region were deleted, (2) a portion of the TACI stalk region was replaced with a portion of the BCMA stalk region, (3) the arginine residue at position 119 was mutated to eliminate a potential furin cleavage site, (4) the glutamine residue at position 121 was mutated to eliminate a potential furin cleavage site, (5) the arginine residue at position 122 was mutated to eliminate a potential furin cleavage site, (6) amino acid residue at positions 123 and 142 were mutated to amino acid residues found in corresponding positions of murine TACI, (7) the human otPA signal sequence was replaced with a human heavy chain variable region signal sequence, (8) the valine residue at position 29 was mutated to methionine, and the otPA signal sequence was joined in an amino terminal position to this residue, and (9) the otPA signal sequence was joined in an amino terminal location to the alanine residue at position 30.

Modifications were also introduced in the immunoglobulin moiety. Five classes of immunoglobulin, IgG, IgA, IgM, IgD, and IgE, have been identified in higher vertebrates. IgG, IgD, and IgE proteins are characteristically disulfide linked heterotetramers consisting of two identical heavy chains and two identical light chains. Typically, IgM is found as a pentamer of a tetramer, whereas IgA occurs as a dimer of a tetramer.

IgG comprises the major class as it normally exists as the second most abundant protein found in plasma. In humans, IgG consists of four subclasses, designated IgG1, IgG2,

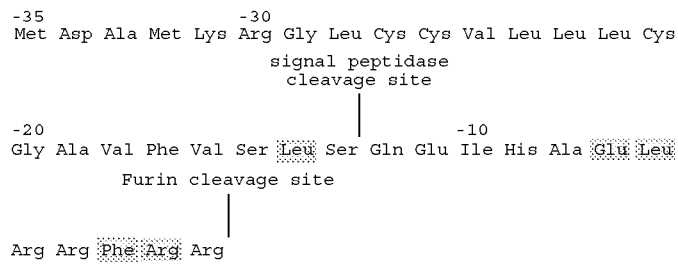

Transfected Chinese hamster ovary cells produced the TACI-Fc4 protein at a low level of about 0.3 pg/cell/day. Western blot analysis of TACI-Fc protein with goat anti- IgG3, and IgG4. As shown in FIG. 2, each immunoglobulin heavy chain possesses a constant region that consists of constant region protein domains ($C_{H1}$, hinge, $C_{H2}$, and $C_{H3}$) that are invariant for a given subclass. The heavy chain constant regions of the IgG class are identified with the Greek symbol γ. For example, immunoglobulins of the IgG1 subclass contain a γ1 heavy chain constant region.

The Fc fragment, or Fc domain, consists of the disulfide linked heavy chain hinge regions, $C_{H2}$, and $C_{H3}$ domains. In immunoglobulin fusion proteins, Fc domains of the IgG1 subclass are often used as the immunoglobulin moiety, because IgG1 has the longest serum half-life of any of the serum proteins. Lengthy serum half-life can be a desirable protein characteristic for animal studies and potential human therapeutic use. In addition, the IgG1 subclass possesses the strongest ability to carry out antibody mediated effector functions. The primary effector function that may be most useful in an immunoglobulin fusion protein is the ability for an IgG1 antibody to mediate antibody dependent cellular cytotoxicity. On the other hand, this could be an undesirable function for a fusion protein that functions primarily as an antagonist. Several of the specific amino acid residues that are important for antibody constant region-mediated activity in the IgG1 subclass have been identified. Inclusion or exclusion of these specific amino acids therefore allows for inclusion or exclusion of specific immunoglobulin constant region-mediated activity.

Six versions of a modified human IgG1 Fc were generated for creating Fc fusion proteins. Fc-488 was designed for convenient cloning of a fusion protein containing the human γ1 Fc region, and it was constructed using the wild-type human immunoglobulin γ1 constant region as a template. Concern about potential deleterious effects due to an unpaired cysteine residue led to the decision to replace the cysteine (amino acid residue 24 of SEQ ID NO:6) that normally disulfide bonds with the immunoglobulin light chain constant region with a serine residue. An additional change was introduced at the codon encoding EU index position 218 (amino acid residue 22 of SEQ ID NO:6) to introduce a BglII restriction enzyme recognition site for ease of future DNA manipulations. These changes were introduced into the PCR product encoded on the PCR primers. Due to the location of the BglII site and in order to complete the Fc hinge region, codons for EU index positions 216 and 217 (amino acid residues 20 and 21 of SEQ ID NO:6) were incorporated in the fusion protein partner sequences.

Fc4, Fc5, and Fc6 contain mutations to reduce effector functions mediated by the Fc by reducing FcγRI binding and complement C1q binding. Fc4 contains the same amino acid substitutions that were introduced into Fc-488. Additional amino acid substitutions were introduced to reduce potential Fc mediated effector functions. Specifically, three amino acid substitutions were introduced to reduce FcγRI binding. These are the substitutions at EU index positions 234, 235, and 237 (amino acid residues 38, 39, and 41 of SEQ ID NO:6). Substitutions at these positions have been shown to reduce binding to FcγRI (Duncan et al., Nature 332:563 (1988)). These amino acid substitutions may also reduce FcγRIIa binding, as well as FcγRIII binding (Sondermann et al., Nature 406:267 (2000); Wines et al., J. Immunol. 164:5313 (2000)).

Several groups have described the relevance of EU index positions 330 and 331 (amino acid residues 134 and 135 of SEQ ID NO:6) in complement C1q binding and subsequent complement fixation (Canfield and Morrison, J. Exp. Med. 173:1483 (1991); Tao et al., J. Exp. Med. 178:661 (1993)). Amino acid substitutions at these positions were introduced in Fc4 to reduce complement fixation. The $C_{H3}$ domain of Fc4 is identical to that found in the corresponding wild-type polypeptide, except for the stop codon, which was changed from TGA to TAA to eliminate a potential dam methylation site when the cloned DNA is grown in dam plus strains of E. coli.

In Fc5, the arginine residue at EU index position 218 was mutated back to a lysine, because the BglII cloning scheme was not used in fusion proteins containing this particular Fc. The remainder of the Fc5 sequence matches the above description for Fc4.

Fc6 is identical to Fc5 except that the carboxyl terminal lysine codon has been eliminated. The C-terminal lysine of mature immunoglobulins is often removed from mature immunoglobulins post-translationally prior to secretion from B-cells, or removed during serum circulation. Consequently, the C-terminal lysine residue is typically not found on circulating antibodies. As in Fc4 and Fc5 above, the stop codon in the Fc6 sequence was changed to TAA.

Fc7 is identical to the wild-type γ1 Fc except for an amino acid substitution at EU index position 297 located in the $C_{H2}$ domain. EU index position Asn-297 (amino acid residue 101 of SEQ ID NO:6) is a site of N-linked carbohydrate attachment. N-linked carbohydrate introduces a potential source of variability in a recombinantly expressed protein due to potential batch-to-batch variations in the carbohydrate structure. In an attempt to eliminate this potential variability, Asn-297 was mutated to a glutamine residue to prevent the attachment of N-linked carbohydrate at that residue position. The carbohydrate at residue 297 is also involved in Fc binding to the FcγRIII (Sondermann et al., Nature 406:267 (2000)). Therefore, removal of the carbohydrate should decrease binding of recombinant Fc7 containing fusion proteins to the FcγRs in general. As above, the stop codon in the Fc7 sequence was mutated to TAA.

Fc8 is identical to the wild-type immunoglobulin γ1 region shown in SEQ ID NO:6, except that the cysteine residue at EU index position 220 (amino acid residue 24 of SEQ ID NO:6) was replaced with a serine residue. This mutation eliminated the cysteine residue that normally disulfide bonds with the immunoglobulin light chain constant region.

Illustrative TACI-Fc constructs are described in Table 1.

TABLE 1

Illustrative TACI-Fc Fusion Protein Constructs

| TACI Sequence[a] | Fc Version |
| --- | --- |
| TACI[b] | Fc4 |
| TACI[b] | Fc5 |
| TACI[b] | Fcγ1 |
| TACI (d107-154) | Fc5 |
| TACI (R119Q) | Fc4 |
| TACI (1-104)-BCMA (42-54)[c] | Fc5 |
| TACI (d143-150) | Fc5 |
| TACI (R142G, d143-150) | Fc5 |
| TACI (R119G, Q121P, R122Q, S123A) | Fc5 |
| TACI(R119G, R122Q) | Fc5 |
| TACI (d1-28, V29M) | Fc6 |
| TACI (d1-29) | Fc6 |
| TACI (d1-29) | Fc5 |
| TACI (d1-29, d107-154) | Fc5 |
| TACI (d1-29, d111-154) | Fc5 |
| TACI (d1-29, d120-154) | Fc5 |

[a]Information about locations, mutations, and deletions of amino acid sequences is provided within parentheses in reference to the amino acid sequence of SEQ ID NO: 2.
[b]Includes amino acid residues 1 to 154 of SEQ ID NO: 2.
[c]This construct includes amino acid residues 1 to 104 of SEQ ID NO: 2 (TACI) and amino acids 42 to 54 of SEQ ID NO: 27 (BCMA).

The TACI-Fc proteins were produced by recombinant Chinese hamster ovary cells, isolated, and analyzed using Western blot analysis and amino acid sequence analysis. Surprisingly, deletion of the first 29 amino acids from the N-terminus of the TACI polypeptide resulted in a ten-fold increase in the production of TACI-Fc fusion proteins by Chinese hamster ovary cells. This deletion also reduced the cleavage of the full-length stalk region. In addition, cleavage within the TACI stalk region was suppressed either by truncating the TACI stalk region, or by replacing the TACI stalk region within another amino acid sequence (e.g., the amino acid sequence of the BCMA stalk region).

As described in Example 4, functional analyses of TACI-Fc constructs indicate that fusion proteins TACI (d1-29)-Fc5, TACI (d1-29, d107-154)-Fc5, TACI (d1-29, d111-154)-Fc5, and TACI (d1-29, d120-154)-Fc5 have similar binding affinities for ZTNF4. However, constructs, TACI (d1-29)-Fc5, TACI (d1-29, d111-154)-Fc5, and TACI (d1-29, d120-154)-Fc5 appear to bind more ZTNF4 per mole of TACI-Fc than construct, TACI (d1-29, d107-154)-Fc5. Depending upon the intended use (i.e., therapeutic, diagnostic, or research), either high capacity or low capacity TACI-Fc fusion proteins can be employed. In addition, a combination of high capacity and low capacity TACI-Fc fusion proteins enables the titration of ZTNF2 or ZTNF4.

The present invention contemplates TACI-immunoglobulin fusion proteins that comprise a TACI receptor moiety consisting of amino acid residues 30 to 106 of SEQ ID NO:2, 30 to 110 of SEQ ID NO:2, 30 to 119 of SEQ ID NO:2, or 30 to 154 of SEQ ID NO:2. The present invention also includes TACI-immunoglobulin fusion proteins that comprise a TACI receptor moiety consisting of amino acid residues 31 to 106 of SEQ ID NO:2, 31 to 110 of SEQ ID NO:2, 31 to 119 of SEQ ID NO:2, or 31 to 154 of SEQ ID NO:2.

More generally, the present invention includes TACI-immunoglobulin fusion proteins, wherein the TACI receptor moiety consists of a fragment of amino acid residues 30 to 154 of SEQ ID NO:2, and wherein the TACI receptor moiety binds at least one of ZTNF2 or ZTNF4. Such fragments comprise a cysteine-rich pseudo-repeat region, and optionally, can include at least one of an N-terminal segment, which resides in an amino-terminal position to the cysteine-rich pseudo-repeat region, and a stalk segment, which resides in a carboxyl-terminal position to the cysteine-rich pseudo-repeat region. Suitable cysteine-rich pseudo-repeat regions include polypeptides that: (a) comprise at least one of amino acid residues 34 to 66 of SEQ ID NO:2, and amino acid residues 71 to 104 of SEQ ID NO:2, (b) comprise both amino acid residues 34 to 66 of SEQ ID NO:2, and amino acid residues 71 to 104 of SEQ ID NO:2, or (c) comprise amino acid residues 34 to 104 of SEQ ID NO:2.

Suitable N-terminal segments include the following with reference to SEQ ID NO:2: amino acid residue 33, amino acid residues 32 to 33, amino acid residues 31 to 33, and amino acid residues 30 to 33. Suitable stalk segments include one or more amino acids of amino acid residues 105 to 154 of SEQ ID NO:2. For example, the stalk segment can consist of the following with reference to SEQ ID NO:2: amino acid residue 105, amino acid residues 105 to 106, amino acid residues 105 to 107, amino acid residues 105 to 108, amino acid residues 105 to 109, amino acid residues 105 to 110, amino acid residues 105 to 111, amino acid residues 105 to 112, amino acid residues 105 to 113, amino acid residues 105 to 114, amino acid residues 105 to 115, amino acid residues 105 to 116, amino acid residues 105 to 117, amino acid residues 105 to 118, amino acid residues 105 to 119, amino acid residues 105 to 120, amino acid residues 105 to 121, amino acid residues 105 to 122, amino acid residues 105 to 123, amino acid residues 105 to 124, amino acid residues 105 to 125, amino acid residues 105 to 126, amino acid residues 105 to 127, amino acid residues 105 to 128, amino acid residues 105 to 129, amino acid residues 105 to 130, amino acid residues 105 to 131, amino acid residues 105 to 132, amino acid residues 105 to 133, amino acid residues 105 to 134, amino acid residues 105 to 135, amino acid residues 105 to 136, amino acid residues 105 to 137, amino acid residues 105 to 138, amino acid residues 105 to 139, amino acid residues 105 to 140, amino acid residues 105 to 141, amino acid residues 105 to 142, amino acid residues 105 to 143, amino acid residues 105 to 144, amino acid residues 105 to 145, amino acid residues 105 to 146, amino acid residues 105 to 147, amino acid residues 105 to 148, amino acid residues 105 to 149, amino acid residues 105 to 150, amino acid residues 105 to 151, amino acid residues 105 to 152, amino acid residues 105 to 153, and amino acid residues 105 to 154.

Additional suitable stalk segments include one or more amino acids of the BCMA stalk region (i.e., amino acid residues 42 to 54 of SEQ ID NO:27. For example, a stalk segment can consist of the following with reference to SEQ ID NO:27: amino acid residue 42, amino acid residues 42 to 43, amino acid residues 42 to 44, amino acid residues 42 to 45, amino acid residues 42 to 46, amino acid residues 42 to 47, amino acid residues 42 to 48, amino acid residues 42 to 49, amino acid residues 42 to 50, amino acid residues 42 to 51, amino acid residues 42 to 52, amino acid residues 42 to 53, and amino acid residues 42 to 54. More generally, a stalk segment can consist of two to 50 amino acid residues.

The immunoglobulin moiety of a fusion protein described herein comprises at least one constant region of an immunoglobulin. Preferably, the immunoglobulin moiety represents a segment of a human immunoglobulin. The human immunoglobulin sequence can be a wild-type amino acid sequence, or a modified wild-type amino acid sequence, which has at least one of the amino acid mutations discussed above.

The human immunoglobulin amino acid sequence can also vary from wild-type by having one or more mutations characteristic of a known allotypic determinant. Table 2 shows the allotypic determinants of the human IgGγ1 constant region (Putman, *The Plasma Proteins, Vol. V*, pages 49 to 140 (Academic Press, Inc. 1987)). EU index positions 214, 356, 358, and 431 define the known IgGγ1 allotypes. Position 214 is in the $C_{H1}$ domain of the IgGγ1 constant region, and, therefore, does not reside within the Fc sequence. The wild-type Fc sequence of SEQ ID NO:6 includes the G1m(1) and G1m(2-) allotypes. However, the Fc moiety of a TACI-Fc protein can be modified to reflect any combination of these allotypes.

TABLE 2

Allotypic Determinants of the Human Immunoglobulin γ1 Constant Region

| Allotype | Amino Acid Residue | Amino Acid Position | |
|---|---|---|---|
| | | EU Index | SEQ ID NO: 6 |
| G1m(1) | Asp, Leu | 356, 358 | 160, 162 |
| G1m(1-) | Glu, Met | 356, 358 | 160, 162 |
| G1m(2) | Gly | 431 | 235 |
| G1m(2-) | Ala | 431 | 235 |
| G1m(3) | Arg | 214 | — |
| G1m(3-) | Lys | 214 | — |

The examples of TACI-Fc proteins disclosed herein comprise human IgG1 constant regions. However, suitable immunoglobulin moieties also include polypeptides comprising at least one constant region, such as a heavy chain constant region from any of the following immunoglobulins: IgG2, IgG3, IgG4, IgA1, IgA2, IgD, IgE, and IgM. Advantageously, immunoglobulin moieties derived from wild-type IgG2 or wild-type IgG4 offer reduced effector function, compared with wild-type IgG1 or wild-type IgG3. The present invention also contemplates fusion proteins that comprise a TACI receptor moiety, as described above, and either albumin or β2-macroglobulin.

Another type of receptor fusion protein that binds ZTNF2 or ZTNF4 is a BCMA-immunoglobulin fusion protein. Studies have been performed with a BCMA-Fc4 fusion protein in which the BCMA moiety consists of amino acid residues 1 to 48 of SEQ ID NO:27. Surprisingly, pharmacokinetic studies in mice revealed that BCMA-Fc4 fusion protein had a half-life of about 101 hours, whereas a TACI-Fc protein had a half-life of 25 hours. Thus, administration of a BCMA-immunoglobulin fusion protein may be preferred in certain clinical settings. Moreover, a combination of TACI-immunoglobulin and BCMA-immunoglobulin fusion proteins may be advantageous to treat certain conditions. This combination therapy can be achieved by administering TACI-immunoglobulin and BCMA-immunoglobulin fusion proteins, or by administering heterodimers of TACI-immunoglobulin and BCMA-immunoglobulin fusion proteins.

Another type of receptor fusion protein that binds ZTNF4 is an immunoglobulin fusion protein comprising an extracellular domain of a receptor designated as "Ztnfr12." Ztnfr12 amino acid and nucleotide sequences are provided as SEQ ID NO:59 and SEQ ID NO:60, respectively. Suitable Ztnfr12 receptor moieties include polypeptides comprising amino acid residues 1 to 69 of SEQ ID NO:60, or amino acid residues 19 to 35 of SEQ ID NO:60.

The fusion proteins of the present invention can have the form of single chain polypeptides, dimers, trimers, or multiples of dimers or trimers. Dimers can be homodimers or heterodimers, and trimers can be homotrimers or heterotrimers. Examples of heterodimers include a TACI-immunoglobulin polypeptide with a BCMA-immunoglobulin polypeptide, a TACI-immunoglobulin polypeptide with a Ztnfr12-immunoglobulin polypeptide, and a BCMA-immunoglobulin polypeptide with a Ztnfr12-immunoglobulin polypeptide. Examples of heterotrimers include a TACI-immunoglobulin polypeptide with two BCMA-immunoglobulin polypeptides, a TACI-immunoglobulin polypeptide with two Ztnfr12-immunoglobulin polypeptides, a BCMA-immunoglobulin polypeptide with two Ztnfr12-immunoglobulin polypeptides, two TACI-immunoglobulin polypeptides with a BCMA-immunoglobulin polypeptide, two TACI-immunoglobulin polypeptides with a Ztnfr12-immunoglobulin polypeptide, two BCMA-immunoglobulin polypeptides with a Ztnfr12-immunoglobulin polypeptide, and a trimer of a TACI-immunoglobulin polypeptide, a BCMA-immunoglobulin polypeptide, and a Ztnfr12-immunoglobulin polypeptide.

In such fusion proteins, the TACI receptor moiety can comprise at least one of the following amino acid sequences of SEQ ID NO:2: amino acid residues 30 to 154, amino acid residues 34 to 66, amino acid residues 71 to 104, amino acid residues 47 to 62, and amino acid residues 86 to 100. The BCMA receptor moiety can comprise at least one of the following amino acid sequences of SEQ ID NO:27: amino acid residues 1 to 48, amino acid residues 8 to 41, and amino acid residues 21 to 37. The Ztnfr12 receptor moiety can comprise at least one of the following amino acid sequences of SEQ ID NO:60: amino acid residues 1 to 69, and amino acid residues 19 to 35.

Fusion proteins can be produced using the PCR methods used to construct the illustrative TACI-Fc molecules, which are described in the Examples. However, those of skill in the art can use other standard approaches. For example, nucleic acid molecules encoding TACI, BCMA, Ztnfr12, or immunoglobulin polypeptides can be obtained by screening human cDNA or genomic libraries using polynucleotide probes based upon sequences disclosed herein. These techniques are standard and well-established (see, for example, Ausubel et al. (eds.), *Short Protocols in Molecular Biology*, 3$^{rd}$ Edition, pages 4-1 to 4-6 (John Wiley & Sons 1995) ("Ausubel (1995)"); Wu et al., *Methods in Gene Biotechnology*, pages 33-41 (CRC Press, Inc. 1997) ("Wu (1997)"); Ausubel (1995) at pages 5-1 to 5-6; Wu (1997) at pages 307-327)).

Alternatively, molecules for constructing immunoglobulin fusion proteins can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol.* 15: *PCR Protocols: Current Methods and Applications*, White (ed.), pages 263-268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

4. Production of TACI-Immunoglobulin Polypeptides

The polypeptides of the present invention can be produced in recombinant host cells following conventional techniques. To express a TACI-immunoglobulin-encoding sequence, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

Expression vectors can also include nucleotide sequences encoding a secretory sequence that directs the heterologous polypeptide into the secretory pathway of a host cell. For example, an expression vector may comprise a nucleotide sequence that encodes TACI-immunoglobulin and a secretory sequence derived from any secreted gene. As discussed above, one suitable signal sequence is a tPA signal sequence. An exemplary tPA signal sequence is provided by SEQ ID NO:25. Another suitable signal sequence is a murine 26-10 $V_H$ signal sequence. The murine 26-10 antibody is described, for example, by Near et al., *Mol. Immunol.* 27:901 (1990). Illustrative amino acid and nucleotide sequences of a murine 26-10 $V_H$ signal sequence are provided by SEQ ID NO:61 and SEQ ID NO:65, respectively. SEQ ID NO:62 discloses the amino acid sequence of a TACI-Fc5 fusion protein that comprises a murine 26-10 $V_H$ signal sequence.

TACI-immunoglobulin proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)). One useful combination of a promoter and enhancer is provided by a myeloproliferative sarcoma virus promoter and a human cytomegalovirus enhancer.

Alternatively, a prokaryotic promoter, such as the bacteriophage T3 RNA polymerase promoter, can be used to control production of TACI-immunoglobulin proteins in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

TACI-immunoglobulin polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Those of skill in the art can devise suitable expression vectors for producing the fusion proteins described herein with mammalian cells. Example 4 describes features of one expression vector. As another example, an expression vector can comprise a bicistronic expression cassette that includes a portion of the human cytomegalovirus enhancer, the myeloproliferative sarcoma virus promoter, a nucleotide sequence encoding a fusion protein, the poliovirus internal ribosomal entry sites, a nucleotide sequence encoding murine dihydrofolate reductase, followed by the SV40 poly A addition sequence. The nucleotide sequence of SEQ ID NO:69 shows a cytomegalovirus enhancer/myeloproliferative sarcoma virus LTR promoter construct, in which the cytomegalovirus enhancer extends from nucleotide 1 to 407. The myeloproliferative sarcoma virus LTR promoter, absent the negative control region extends from nucleotide 408 to nucleotide 884 of SEQ ID NO:69. A nucleotide sequence for the myeloproliferative sarcoma virus LTR promoter without the negative control region is provided in SEQ ID NO:70.

Example 1 describes an expression vector that comprises a cytomegalovirus promoter to direct the expression of the recombinant protein transgene, an immunoglobulin intron, and a tissue plasminogen activator signal sequence. One suitable immunoglobulin intron is a murine 26-10 $V_H$ intron. SEQ ID NO:66 provides an illustrative nucleotide sequence of a murine 26-10 $V_H$ intron. An expression vector may also include a 5' untranslated region (UTR) located upstream of the nucleotide sequence that encodes a TACI-immunoglobulin protein. A suitable 5'-UTR can be derived from the murine 26-10 $V_H$ gene. SEQ ID NO:63 discloses the nucleotide sequence of a useful native murine 26-10 $V_H$ 5'-UTR, while SEQ ID NO:64 shows the nucleotide sequence of a murine 26-10 $V_H$ 5'-UTR, which has been optimized at the 3' end.

As an illustration, SEQ ID NO:67 provides a nucleotide sequence that includes the following elements: a native murine 26-10 $V_H$ 5'-UTR (nucleotides 1 to 51), a murine 26-10 $V_H$ signal sequence (nucleotides 52 to 97, and 182 to 192), a murine 26-10 $V_H$ intron (nucleotides 98 to 181), a nucleotide sequence that encodes a TACI moiety (nucleotides 193 to 435), and a nucleotide sequence that encodes an Fc5 moiety (nucleotides 436 to 1131). The nucleotide sequence of SEQ ID NO:68 differs from SEQ ID NO:67 due to the replacement of an optimized murine 26-10 $V_H$ 5'-UTR (nucleotides 1 to 51) for the native sequence.

TACI-immunoglobulin proteins can also be expressed in other higher eukaryotic cells, such as avian, fungal, insect, yeast, or plant cells. The baculovirus system provides an efficient means to introduce cloned genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the TACI-immunoglobulin polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed TACI-immunoglobulin polypeptide, for example, a Glu-Glu epitope tag (Grussenmeyer et al., *Proc. Nat'l Acad. Sci.* 82:7952 (1985)). Using a technique known in the art, a transfer vector containing a nucleotide sequence that encodes a TACI-immunoglobulin protein is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed, with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in such constructs.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. A vector can be designed to generate constructs utilizing the necessary elements to carry out homologous recombination in yeast (see, for example, Raymond et al., *BioTechniques* 26:134 (1999)). For example, such an expression vector can include URA3 and CEN-ARS (autonomously replicating sequence) sequences required for selection and replication in *S. cerevisiae*. Other suitable vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides from these cells are disclosed by, for example, Kawasaki, U.S. Pat. No. 4,599,311, Kawasaki et al., U.S. Pat. No. 4,931,373, Brake, U.S. Pat. No.

4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, TACI-immunoglobulin proteins can be produced in prokaryotic host cells. Suitable promoters that can be used to produce TACI-immunoglobulin polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus*, *Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilis*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilis* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a TACI-immunoglobulin protein in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163

(Wiley-Liss, Inc. 1996). Standard techniques for recovering protein produced by a bacterial system is provided by, for example, Grisshammer et al., "Purification of over-produced proteins from *E. coli* cells," in *DNA Cloning* 2: *Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

5. Assays for TACI-Immunoglobulin Fusion Proteins

The function of TACI-immunoglobulin fusion proteins can be examined using a variety of approaches to assess the ability of the fusion proteins to bind ZTNF4 or ZTNF2. As an illustration, Example 4 provides methods for measuring ZTNF4 binding affinity and binding capacity.

Alternatively, TACI-immunoglobulin fusion proteins can be characterized by the ability to inhibit the stimulation of human B cells by soluble ZTNF4, as described by Gross et al., international publication No. WO00/40716. Briefly, human B cells are isolated from peripheral blood mononuclear cells using CD19 magnetic beads and the VarioMacs magnetic separation system (Miltenyi Biotec Auburn, Calif.) according to the manufacturer's instructions. Purified B cells are mixed with soluble ZTNF4 (25 ng/ml) and recombinant human IL-4 (10 ng/ml Pharmingen), and the cells are plated onto round bottom 96 well plates at $1 \times 10^5$ cells per well.

Soluble TACI-immunoglobulin proteins can be diluted from about 5 µg/ml to about 6 ng/ml, and incubated with the B cells for five days, pulsing overnight on day four with 1 µCi $^3$H-thymidine per well. As a control, TACI-immunoglobulin protein can also be incubated with B cells and IL-4 without ZTNF4. Plates are harvested using Packard plate harvester, and counted using the Packard reader.

This general approach was used to examine three TACI-Fc fusion proteins. Although all fusion proteins inhibited B cell proliferation, constructs TACI (d1-29, d111-154)-Fc5 and TACI (d1-29, d120-154)-Fc5 were more potent than TACI (d1-29, d107-154)-Fc5.

Well-established animal models are available to test in vivo efficacy of TACI-immunoglobulin proteins in certain disease states. For example, TACI-immunoglobulin proteins can be tested in a number of animal models of autoimmune disease, such as MRL-lpr/lpr or NZBxNZW F1 congenic mouse strains, which serve as a model of SLE (systemic lupus erythematosus). Such animal models are known in the art (see, for example, Cohen and Miller (Eds.), *Autoimmune Disease Models: A Guidebook* (Academic Press, Inc. 1994).

Offspring of a cross between New Zealand Black (NZB) and New Zealand White (NZW) mice develop a spontaneous form of SLE that closely resembles SLE in humans. The offspring mice, known as NZBW begin to develop IgM autoantibodies against T-cells at one month of age, and by five to seven months of age, anti-DNA autoantibodies are the dominant immunoglobulin. Polyclonal B-cell hyperactivity leads to overproduction of autoantibodies. The deposition of these autoantibodies, particularly those directed against single stranded DNA, is associated with the development of glomerulonephritis, which manifests clinically as proteinuria, azotemia, and death from renal failure.

Kidney failure is the leading cause of death in mice affected with spontaneous SLE, and in the NZBW strain, this process is chronic and obliterative. The disease is more rapid and severe in females than males, with mean survival of only 245 days as compared to 406 days for the males. While many of the female mice will be symptomatic (proteinuria) by seven to nine months of age, some can be much younger or older when they develop symptoms. The fatal immune nephritis seen in the NZBW mice is very similar to the glomerulonephritis seen in human SLE, making this spontaneous murine model very attractive for testing of potential SLE therapeutics (Putterman and Naparstek, "Murine Models of Spontaneous Systemic Lupus Erythematosus," in *Autoimmune Disease Models: A Guidebook*, pages 217-234 (Academic Press, Inc., 1994); Mohan et al., *J. Immunol.* 154:1470 (1995); and Daikh et al., *J. Immunol.* 159:3104 (1997)).

As described by Gross et al., international publication No. WO00/40716, TACI-immunoglobulin proteins can be administered to NZBW mice to monitor its suppressive effect on B cells over the five-week period when, on average, B-cell autoantibody production is believed to be at high levels in NZBW mice. Briefly, 100 8-week old female (NZBxNZW) $F_1$ mice can be divided into six groups of 15 mice. Prior to treatment, the mice are monitored once a month for urine protein, and blood is drawn for CBC and serum banking. Serum can be screened for the presence of autoantibodies. Because proteinuria is the hallmark sign of glomerulonephritis, urine protein levels are monitored by dipstick at regular intervals over the course of the study. Treatment can begin when mice are approximately five months of age. The mice receive intraperitoneal injections of vehicle only (phosphate buffered saline) or human TACI-immunoglobulin (control protein) or TACI-immunoglobulin protein (e.g., 20 to 100 µg test protein per dose) three times a week for five weeks.

Blood is collected twice during treatment, and will be collected at least twice following treatment. Urine dipstick values for proteinuria and body weights are determined every two weeks after treatment begins. Blood, urine dipstick value and body weight are collected at the time of euthanasia. The spleen and thymus are divided for fluorescent activated cell sorting analysis and histology. Submandibular salivary glands, mesenteric lymph node chain, liver lobe with gall bladder, cecum and large intestine, stomach, small intestine, pancreas, right kidney, adrenal gland, tongue with trachea and esophagus, heart and lungs are also collected for histology.

Murine models for experimental allergic encephalomyelitis have been used as a tool to investigate both the mechanisms of immune-mediated disease, and methods of potential therapeutic intervention. The model resembles human multiple sclerosis, and produces demyelination as a result of T-cell activation to neuroproteins such as myelin basic protein, or proteolipid protein. Inoculation with antigen leads to induction of CD4+, class II MHC-restricted T-cells (Th1). Changes in the protocol for experimental allergic encephalomyelitis can produce acute, chronic-relapsing, or passive-transfer variants of the model (Weinberg et al., *J. Immunol.* 162:1818 (1999); Mijaba et al., *Cell. Immunol.* 186:94 (1999); and Glabinski, *Meth. Enzym.* 288:182 (1997)).

Gross et al., international publication No. WO00/40716, describe one approach to evaluating the efficacy of TACI-immunoglobulin proteins in the amelioration of symptoms associated with experimental allergic encephalomyelitis. Briefly, 25 female PL×SJL F1 mice (12 weeks old) are given a subcutaneous injection of 125 μg/mouse of antigen (myelin Proteolipid Protein, PLP, residues 139-151), formulated in complete Freund's Adjuvant. The mice are divided into five groups of five mice. Intraperitoneal injections of pertussis toxin (400 ng) are given on Day 0 and 2. The groups are given a 1×, 10×, or 100× dose of TACI-immunoglobulin protein, one group will receive vehicle only, and one group will receive no treatment. Prevention therapy begins on Day 0, intervention therapy begins on day 7, or at onset of clinical signs. Signs of disease, weight loss, and paralysis manifest in approximately 10 to 14 days, and last for about one week. Animals are assessed daily by collecting body weights and assigning a clinical score to correspond to the extent of their symptoms. Clinical signs of experimental allergic encephalomyelitis appear within 10 to 14 days of inoculation and persist for approximately one week. At the end of the study, all animals are euthanized by gas overdose, and necropsied. The brain and spinal column are collected for histology or frozen for mRNA analysis. Body weight and clinical score data are plotted by individual and by group.

In the collagen-induced arthritis model, mice develop chronic inflammatory arthritis, which closely resembles human rheumatoid arthritis. Since collagen-induced arthritis shares similar immunological and pathological features with rheumatoid arthritis, this makes it an ideal model for screening potential human anti-inflammatory compounds. Another advantage in using the collagen-induced arthritis model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined, and can be used to assess test compound efficacy in the models (Wooley, *Curr. Opin. Rheum.* 3:407 (1999); Williams et al., *Immunol.* 89:9784 (1992); Myers et al., *Life Sci.* 61:1861 (1997); and Wang et al., *Immunol.* 92:8955 (1995)).

Gross et al., international publication No. WO00/40716, describe a method for evaluating the efficacy of TACI-immunoglobulin proteins in the amelioration of symptoms associated with collagen-induced arthritis. In brief, eight-week old male DBA/1J mice (Jackson Labs) are divided into groups of five mice/group and are given two subcutaneous injections of 50 to 100 μl of 1 mg/ml collagen (chick or bovine origin), at three week intervals. One control does not receive collagen injections. The first injection is formulated in Complete Freund's Adjuvant, and the second injection is formulated in Incomplete Freund's Adjuvant. TACI-immunoglobulin protein is administered prophylactically at or before the second injection, or after the animal develops a clinical score of two or more that persists at least 24 hours. Animals begin to show symptoms of arthritis following the second collagen injection, usually within two to three weeks. For example, TACI-Fc, a control protein, human IgFc, or phosphate-buffered saline (vehicle) can be administered prophylactically beginning seven days before the second injection (day −7). Proteins can be administered at 100 μg, given three times a week as a 200 μl intraperitoneal injection, and continued for four weeks.

In the collagen-induced arthritis model, the extent of disease is evaluated in each paw using a caliper to measure paw thickness and assigning a clinical score to each paw. For example, a clinical score of "0" indicates a normal mouse, a score of "1" indicates that one or more toes are inflamed, a score of "2" indicates mild paw inflammation, a score of "3" indicates moderate paw inflammation, and a score of "4" indicates severe paw inflammation Animals are euthanized after the disease as been established for a set period of time, usually seven days. Paws are collected for histology or mRNA analysis, and serum is collected for immunoglobulin and cytokine assays.

Myasthenia gravis is another autoimmune disease for which murine models are available. Myasthenia gravis is a disorder of neuromuscular transmission involving the production of autoantibodies directed against the nicotinic acetylcholine receptor. This disease is acquired or inherited with clinical features including abnormal weakness and fatigue on exertion.

A murine model of myasthenia gravis has been established. (Christadoss et al., "Establishment of a Mouse Model of Myasthenia gravis Which Mimics Human Myasthenia gravid Pathogenesis for Immune Intervention," in *Immunobiology of Proteins and Peptides VIII*, Atassi and Bixler (Eds.), pages 195-199 (1995)). Experimental autoimmune myasthenia gravis is an antibody mediated disease characterized by the presence of antibodies to acetylcholine receptor. These antibodies destroy the receptor leading to defective neuromuscular electrical impulses, resulting in muscle weakness. In the experimental autoimmune myasthenia gravis model, mice are immunized with the nicotinic acetylcholine receptor. Clinical signs of myasthenia gravis become evident weeks after the second immunization. Experimental autoimmune myasthenia gravis is evaluated by several methods including measuring serum levels of acetylcholine receptor antibodies by radioimmunoassay (Christadoss and Dauphinee, *J. Immunol.* 136:2437 (1986); Lindstrom et al., *Methods Enzymol.* 74:432 (1981)), measuring muscle acetylcholine receptor, or electromyography (Coligan et al. (Eds.), *Protocols in Immunology*. Vol. 3, page 15.8.1 (John Wiley & Sons, 1997)).

The effect of TACI-immunoglobulin on experimental autoimmune myasthenia gravis can be determined by administering fusion proteins during ongoing clinical myasthenia gravis in B6 mice. For example, 100 B6 mice are immunized with 20 μg acetylcholine receptor in complete Freund's adjuvant on days 0 and 30. Approximately 40 to 60% of mice will develop moderate (grade 2) to severe (grade 3) clinical myasthenia gravis after the boost with acetylcholine receptor. Mice with grade 2 and 3 clinical disease are divided into three groups (with equal grades of weakness) and weighed (mice with weakness also lose weight, since they have difficulty in consuming food and water) and bled for serum (for pretreatment anti-acetylcholine receptor antibody and isotype level). Group A is injected I.P with phosphate buffered saline, group B is injected intraperitoneally with human IgG-Fc as a control protein (100 μg), and group C is injected with 100 μg of TACI-Fc three times a week for four weeks. Mice are screened for clinical muscle weakness twice a week, and weighed and bled for serum 15 and 30 days after the commencement of treatment. Whole blood is collected on day 15 to determine T/B cell ratio by fluorescence activated cell sorter analysis using markers B220 and CD5. Surviving mice are killed 30 to 45 days after the initiation of treatment, and their carcasses are frozen for later extraction of muscle acetylcholine receptor to determine the loss of muscle acetylcholine receptor, the primary pathology in myasthenia gravis (see, for example, Coligan et al. (Eds.), *Protocols in Immunology. Vol.* 3, page 15.8.1 (John Wiley & Sons, 1997)).

Serum antibodies to mouse muscle acetylcholine receptor can be determined by an established radioimmunoassay, and anti-acetylcholine receptor antibody isotypes (IgM, IgG1, IgG2b and IgG2c) is measured by ELISA. Such methods are known. The effects of TACI-immunoglobulin on ongoing clinical myasthenia gravis, anti-acetylcholine receptor antibody and isotype level, and muscle acetylcholine receptor loss are determined.

Approximately 100 mice can be immunized with 20 μg acetylcholine receptor in complete Freund's adjuvant on day 0 and 30. Mice with clinical myasthenia gravis are divided into four groups. Group A is injected intraperitoneally with 100 μg control Fc, group B is injected with 20 μg control Fc, group C is injected with 100 μg TACI-Fc, and group D is injected with 20 μg TACI-Fc three times a week for four weeks. Mice are weighed and bled for serum before, and 15 and 30 days after the start of the treatment. Serum is tested for anti-acetylcholine receptor antibody and isotypes as described above. Muscle acetylcholine receptor loss can also be measured.

Other suitable assays of TACI-immunoglobulin fusion proteins can be determined by those of skill in the art.

6. Production of TACI-Immunoglobulin Conjugates

The present invention includes chemically modified TACI-immunoglobulin compositions, in which a TACI-immunoglobulin polypeptide is linked with a polymer. Typically, the polymer is water-soluble so that the TACI-immunoglobulin conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-($C_1$-$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce TACI-immunoglobulin conjugates.

TACI-immunoglobulin conjugates used for therapy can comprise pharmaceutically acceptable water-soluble polymer moieties. Suitable water-soluble polymers include polyethylene glycol (PEG), monomethoxy-PEG, mono-($C_1$-$C_{10}$) alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A TACI-immunoglobulin conjugate can also comprise a mixture of such water-soluble polymers.

One example of a TACI-immunoglobulin conjugate comprises a TACI-immunoglobulin moiety and a polyalkyl oxide moiety attached to the N-terminus of the TACI-immunoglobulin. PEG is one suitable polyalkyl oxide. As an illustration, TACI-immunoglobulin can be modified with PEG, a process known as "PEGylation." PEGylation of TACI-immunoglobulin can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, TACI-immunoglobulin conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a TACI-immunoglobulin polypeptide. An example of an activated PEG ester is PEG esterified to N-hydroxysuccinimide. As used herein, the term "acylation" includes the following types of linkages between TACI-immunoglobulin and a water-soluble polymer: amide, carbamate, urethane, and the like. Methods for preparing PEGylated TACI-immunoglobulin by acylation will typically comprise the steps of (a) reacting a TACI-immunoglobulin polypeptide with PEG (such as a reactive ester of an aldehyde derivative of PEG) under conditions whereby one or more PEG groups attach to TACI-immunoglobulin, and (b) obtaining the reaction product(s). Generally, the optimal reaction conditions for acylation reactions will be determined based upon known parameters and desired results. For example, the larger the ratio of PEG:TACI-immunoglobulin, the greater the percentage of polyPEGylated TACI-immunoglobulin product.

The product of PEGylation by acylation is typically a polyPEGylated TACI-immunoglobulin product, wherein the lysine ε-amino groups are PEGylated via an acyl linking group. An example of a connecting linkage is an amide. Typically, the resulting TACI-immunoglobulin will be at least 95% mono-, di-, or tri-pegylated, although some species with higher degrees of PEGylation may be formed depending upon the reaction conditions. PEGylated species can be separated from unconjugated TACI-immunoglobulin polypeptides using standard purification methods, such as dialysis, ultrafiltration, ion exchange chromatography, affinity chromatography, and the like.

PEGylation by alkylation generally involves reacting a terminal aldehyde derivative of PEG with TACI-immunoglobulin in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of TACI-immunoglobulin monopolymer conjugates.

Reductive alkylation to produce a substantially homogenous population of monopolymer TACI-immunoglobulin conjugate molecule can comprise the steps of: (a) reacting a TACI-immunoglobulin polypeptide with a reactive PEG under reductive alkylation conditions at a pH suitable to permit selective modification of the α-amino group at the amino terminus of the TACI-immunoglobulin, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer TACI-immunoglobulin conjugates, the reductive alkylation reaction conditions are those that permit the selective attachment of the water soluble polymer moiety to the N-terminus of TACI-immunoglobulin. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:TACI-immunoglobulin need not be as large because more reactive groups are available. Typically, the pH will fall within the range of 3 to 9, or 3 to 6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to TACI-immunoglobulin will generally be in the range of 1:1 to 100:1. Typically, the molar ratio of water-soluble polymer to TACI-immunoglobulin will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

7. Isolation of TACI-Immunoglobulin Polypeptides

The polypeptides of the present invention can be purified to at least about 80% purity, to at least about 90% purity, to at least about 95% purity, or greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of synthetic TACI-immunoglobulin polypeptides, and recombinant TACI-immunoglobulin polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in TACI-immunoglobulin isolation and purification can be devised by those of skill in the art. For example, anti-TACI or anti-Fc antibodies can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography, Protein A chromatography, and ion exchange chromatography (M. Deutscher, (ed.), *Meth. Enzymol.* 182:529 (1990)).

TACI-immunoglobulin polypeptides or fragments thereof may also be prepared through chemical synthesis, as described above. TACI-immunoglobulin polypeptides may be monomers or multimers; glycosylated or non-glycosylated; PEGylated or non-PEGylated; and may or may not include an initial methionine amino acid residue. A TACI-immunoglobulin fusion protein may be non-glycosylated, glycosylated, or glycosylated only in the TACI moiety or in the immunoglobulin moiety. The immunoglobulin moiety can be obtained from a human antibody, a chimeric antibody, or a humanized antibody.

8. Therapeutic Uses of TACI-Immunoglobulin Polypeptides

TACI-immunoglobulin proteins can be used to modulate the immune system by binding ZTNF4 or ZTNF2, and thus, preventing the binding of these ligands with endogenous TACI or BCMA receptors. Accordingly, the present invention includes the use of TACI-immunoglobulin proteins to a subject, which lacks an adequate amount of TACI or BCMA receptors, or which produces an excess of ZTNF4 or ZTNF2.

These molecules can be administered to any subject in need of treatment, and the present invention contemplates both veterinary and human therapeutic uses. Illustrative subjects include mammalian subjects, such as farm animals, domestic animals, and human patients.

TACI-immunoglobulin polypeptides can be used for the treatment of autoimmune diseases, B cell cancers, immunomodulation, IBD and any antibody-mediated pathologies (e.g., ITCP, myasthenia gravis and the like), renal diseases, indirect T cell immune response, graft rejection, and graft versus host disease. The polypeptides of the present invention can be targeted to specifically regulate B cell responses during the immune response. Additionally, the polypeptides of the present invention can be used to modulate B cell development, development of other cells, antibody production, and cytokine production. Polypeptides of the present invention can also modulate T and B cell communication by neutralizing the proliferative effects of ZTNF4.

TACI-immunoglobulin polypeptides of the present invention can be useful to neutralize the effects of ZTNF4 for treating pre-B or B-cell leukemias, such as plasma cell leukemia, chronic or acute lymphocytic leukemia, myelomas such as multiple myeloma, plasma cell myeloma, endothelial myeloma and giant cell myeloma, and lymphomas such as non-Hodgkins lymphoma, for which an increase in ZTNF4 polypeptides is associated.

ZTNF4 is expressed in $CD8^+$ cells, monocytes, dendritic cells, activated monocytes, which indicates that, in certain autoimmune disorders, cytotoxic T-cells might stimulate B-cell production through excess production of ZTNF4. Immunosuppressant proteins that selectively block the action of B-lymphocytes would be of use in treating disease. Autoantibody production is common to several autoimmune diseases and contributes to tissue destruction and exacerbation of disease. Autoantibodies can also lead to the occurrence of immune complex deposition complications and lead to many symptoms of systemic lupus erythematosus, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis. As such, inhibition of ZTNF4 antibody production would be beneficial in treatment of autoimmune diseases such as myasthenia gravis, rheumatoid arthritis, polyarticular-course juvenile rheumatoid arthritis, and psoriatic arthritis Immunosuppressant therapeutics such as TACI-immunoglobulin proteins that selectively block or neutralize the action of B-lymphocytes would be useful for such purposes.

The invention provides methods employing TACI-immunoglobulin proteins for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, chronic lymphoid leukemia, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The methods of the present invention also include use of TACI-immunoglobulin proteins in the treatment of hypertensive or large vessel diseases, including renal artery stenosis or occlusion and cholesterol emboli or renal emboli.

The present invention also provides methods for treatment of renal or urological neoplasms, multiple myelomas, lymphomas, light chain neuropathy or amyloidosis.

The invention also provides methods for blocking or inhibiting activated B cells using TACI-immunoglobulin proteins for the treatment of asthma and other chronic airway diseases such as bronchitis and emphysema. The TACI-immunoglobulin proteins described herein can also be used to treat Sjögren's Syndrome.

Also provided are methods for inhibiting or neutralizing an effector T cell response using TACI-immunoglobulin proteins for use in immunosuppression, in particular for such therapeutic use as for graft-versus-host disease and graft rejection. Moreover, TACI-immunoglobulin proteins would be useful in therapeutic protocols for treatment of such autoimmune diseases as insulin dependent diabetes mellitus (IDDM) and Crohn's Disease. Methods of the present invention would have additional therapeutic value for treating chronic inflammatory diseases, in particular to lessen joint pain, swelling, anemia and other associated symptoms as well as treating septic shock.

Well established animal models are available to test in vivo efficacy of TACI-immunoglobulin proteins of the present invention in certain disease states. In particular, TACI-immunoglobulin proteins can be tested in vivo in a number of animal models of autoimmune disease, such as MRL-lpr/lpr or NZB×NZW F1 congenic mouse strains which serve as a model of SLE (systemic lupus erythematosus). Such animal models are known in the art.

Offspring of a cross between New Zealand Black (NZB) and New Zealand White (NZW) mice develop a spontaneous form of SLE that closely resembles SLE in humans. The offspring mice, known as NZBW begin to develop IgM autoantibodies against T-cells at 1 month of age, and by 5-7 months of age, Ig anti-DNA autoantibodies are the dominant immunoglobulin. Polyclonal B-cell hyperactivity leads to overproduction of autoantibodies. The deposition of these autoantibodies, particularly ones directed against single stranded DNA is associated with the development of glomerulonephritis, which manifests clinically as proteinuria, azotemia, and death from renal failure. Kidney failure is the leading cause of death in mice affected with spontaneous SLE, and in the NZBW strain, this process is chronic and obliterative. The disease is more rapid and severe in females than males, with mean survival of only 245 days as compared to 406 days for the males. While many of the female mice will be symptomatic (proteinuria) by 7-9 months of age, some can be much younger or older when they develop symptoms. The fatal immune nephritis seen in the NZBW mice is very similar to the glomerulonephritis seen in human SLE, making this spontaneous murine model useful for testing of potential SLE therapeutics.

Mouse models for experimental allergic encephalomyelitis (EAE) has been used as a tool to investigate both the mechanisms of immune-mediated disease, and methods of potential therapeutic intervention. The model resembles human multiple sclerosis, and produces demyelination as a result of T-cell activation to neuroproteins such as myelin basic protein (MBP), or proteolipid protein (PLP). Inoculation with antigen leads to induction of CD4+, class II MHC-restricted T-cells (Th1). Changes in the protocol for EAE can produce acute, chronic-relapsing, or passive-transfer variants of the model.

In the collagen-induced arthritis (CIA) model, mice develop chronic inflammatory arthritis, which closely resembles human rheumatoid arthritis (RA). Since CIA shares similar immunological and pathological features with RA, this makes it an ideal model for screening potential human anti-inflammatory compounds. Another advantage in using the CIA model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined, and can be used to assess test compound efficacy in the models.

Myasthenia gravis (MG) is another autoimmune disease for which murine models are available. MG is a disorder of neuromuscular transmission involving the production of autoantibodies directed against the nicotinic acetylcholine receptor (AChR). MG is acquired or inherited with clinical features including abnormal weakness and fatigue on exertion. A mouse model of MG has been established. Experimental autoimmune myasthenia gravis (EAMG) is an antibody mediated disease characterized by the presence of antibodies to AChR. These antibodies destroy the receptor leading to defective neuromuscular electrical impulses, resulting in muscle weakness. In the EAMG model, mice are immunized with the nicotinic acetylcholine receptor. Clinical signs of MG become evident weeks after the second immunization. EAMG is evaluated by several methods including measuring serum levels of AChR antibodies by radioimmunoassay, measuring muscle AChR, or electromyography.

Generally, the dosage of administered TACI-immunoglobulin protein will vary depending upon such factors as the subject's age, weight, height, sex, general medical condition and previous medical history. Typically, it is desirable to provide the recipient with a dosage of TACI-immunoglobulin protein, which is in the range of from about 1 pg/kg to 10 mg/kg (amount of agent/body weight of subject), although a lower or higher dosage also may be administered as circumstances dictate.

Administration of a TACI-immunoglobulin protein to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising TACI-immunoglobulin can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of transcutaneous administration (Mitragotri et al., *Science* 269: 850 (1995)). Transdermal delivery using electroporation provides another means to administer a TACI-immunoglobulin protein (Potts et al., *Pharm. Biotechnol.* 10:213 (1997)).

A pharmaceutical composition comprising a TACI-immunoglobulin protein can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, TACI-immunoglobulin proteins are administered to a patient in a therapeutically effective amount. A TACI-immunoglobulin protein and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. As another example, an agent used to inhibit the growth of tumor cells is physiologically significant if the administration of the agent results in a decrease in the number of tumor cells, decreased metastasis, a decrease in the size of a solid tumor, or increased necrosis of a tumor. Furthermore, an agent used to treat systemic lupus erythematosus is physiologically significant if the administration of the agent results in a decrease of circulating anti-double stranded DNA antibodies, or a decrease in at least one of the following symptoms: fever, joint pain, erythematosus skin lesions, or other features of systemic lupus erythematosus. One example of a general indication that a TACI-immunoglobulin protein is administered in a therapeutically effective amount is that, following administration to a subject, there is a decrease in circulating levels of ZTNF4 (BLyS).

A pharmaceutical composition comprising a TACI-immunoglobulin protein can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

TACI-immunoglobulin proteins can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified TACI-immunoglobulin proteins in which the polypeptide is linked with a polymer, as discussed above.

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

As an illustration, pharmaceutical compositions may be supplied as a kit comprising a container that comprises a TACI-immunoglobulin protein. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the TACI-immunoglobulin protein composition is contraindicated in patients with known hypersensitivity to either the TACI receptor moiety or the immunoglobulin moiety.

9. Therapeutic Uses of TACI-Immunoglobulin Nucleotide Sequences

The present invention includes the use of nucleic acid molecules that encode TACI-immunoglobulin fusion proteins to provide these fusion proteins to a subject in need of such treatment. For veterinary therapeutic use or human therapeutic use, such nucleic acid molecules can be administered to a subject having a disorder or disease, as discussed above. As one example discussed earlier, nucleic acid molecules encoding a TACI-immunoglobulin fusion protein can be used for long-term treatment of systemic lupus erythematosus.

There are numerous approaches for introducing a TACI-immunoglobulin gene to a subject, including the use of recombinant host cells that express TACI-immunoglobulin, delivery of naked nucleic acid encoding TACI-immunoglobulin, use of a cationic lipid carrier with a nucleic acid molecule that encodes TACI-immunoglobulin, and the use of viruses that express TACI-immunoglobulin, such as recombinant retroviruses, recombinant adeno-associated viruses, recombinant adenoviruses, and recombinant Herpes simplex viruses (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a TACI-immunoglobulin gene, and then transplanted into the subject.

In order to effect expression of a TACI-immunoglobulin gene, an expression vector is constructed in which a nucleotide sequence encoding a TACI-immunoglobulin gene is operably linked to a core promoter, and optionally a regulatory element, to control gene transcription. The general requirements of an expression vector are described above.

Alternatively, a TACI-immunoglobulin gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle, which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant herpes simplex virus can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a TACI-immunoglobulin gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration. For example, Aihara and Miyazaki, *Nature Biotechnology* 16:867 (1998), have demonstrated the use of in vivo electroporation for gene transfer into muscle.

In general, the dosage of a composition comprising a therapeutic vector having a TACI-immunoglobulin nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor. As an illustration, Horton et al., *Proc. Nat'l Acad. Sci. USA* 96:1553 (1999), demonstrated that intramuscular injection of plasmid DNA encoding interferon-α produces potent antitumor effects on primary and metastatic tumors in a murine model.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences*, 19th Ed. (Mack Publishing Co. 1995), and *Gilman's the Pharmacological Basis of Therapeutics*, 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. For example, an agent used to treat inflammation is physiologically significant if its presence alleviates the inflammatory response. As another example, an agent used to inhibit the growth of tumor cells is physiologically significant if the administration of the agent results in a decrease in the number of tumor cells, decreased metastasis, a decrease in the size of a solid tumor, or increased necrosis of a tumor.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

10. Production of Transgenic Mice

Transgenic mice can be engineered to over-express nucleic acid sequences encoding TACI-immunoglobulin fusion proteins in all tissues, or under the control of a tissue-specific or tissue-preferred regulatory element. These over-producers of TACI-immunoglobulin fusion proteins can be used to characterize the phenotype that results from over-expression, and the transgenic animals can serve as models for human disease caused by excess TACI receptor protein. Transgenic mice that over-express TACI-immunoglobulin fusion proteins also provide model bioreactors for production of TACI-immunoglobulin fusion proteins in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression*, Fernandez and Hoeffler (eds.), pages 367-397 (Academic Press, Inc. 1999)).

For example, a method for producing a transgenic mouse that expresses a nucleic acid sequence that encodes a TACI-immunoglobulin fusion protein can begin with adult, fertile males (studs) (B6C3f1, 2 to 8 months of age (Taconic Farms, Germantown, N.Y.)), vasectomized males (duds) (B6D2f1, 2 to 8 months, (Taconic Farms)), prepubescent fertile females (donors) (B6C3f1, 4 to 5 weeks, (Taconic Farms)) and adult fertile females (recipients) (B6D2f1, 2 to 4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a TACI-immunoglobulin fusion protein encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the TACI-immunoglobulin fusion protein encoding sequences can encode a TACI polypeptide with deletion of amino acid residues 1 to 29 and 111 to 154 of SEQ ID NO:2, and an Fc5 immunoglobulin moiety.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a nucleic acid sequence encoding a TACI-immunoglobulin fusion protein or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of TACI-immunoglobulin fusion protein mRNA is examined for each transgenic mouse using an RNA solution hybridization assay or polymerase chain reaction.

Using the general approach described above, transgenic mice have been produced that express significant levels of TACI-immunoglobulin fusion protein in milk. In this particular case, the TACI-immunoglobulin fusion protein encoding sequence encoded a TACI polypeptide with deletion of amino acid residues 1 to 29 and 111 to 154 of SEQ ID NO:2, and an Fc5 immunoglobulin moiety.

The present invention, thus generally described, will be understood more readily by reference to the following examples, which are provided by way of illustration and is not intended to be limiting of the present invention.

EXPERIMENTAL

Example 1

Construction of Nucleic Acid Molecules that Encode TACI-Fc Proteins

Nucleic acid molecules encoding human TACI were obtained during the expression cloning of the receptors for ZTNF4 as described by Gross et al., *Nature* 404:995 (2000). The coding sequences contained in the TACI-Fc expression constructs were generated by overlap PCR, using standard techniques (see, for example, Horton et al., *Gene* 77:61 (1989)). Human TACI cDNA and Fc cDNA were used as starting templates for the PCR amplifications. PCR primers were designed to yield the desired coding sequence 5' and 3' ends and to introduce restriction enzyme recognition sites to facilitate insertion of these coding sequences into the expression vectors. The TACI-Fc coding sequences were inserted into expression vectors that included a functional murine dihydrofolate reductase gene. One expression vector also contained a cytomegalovirus promoter to direct the expression of the recombinant protein transgene, an immunoglobulin intron, a tissue plasminogen activator signal sequence, an internal ribosome entry sequence, a deleted CD8 cistron for surface selection of transfected cells, and yeast expression elements for growth of the plasmid in yeast cells.

One approach that was used to produce TACI-Fc fusion proteins is illustrated by the method used to construct TACI-Fc4. Other TACI-Fc fusion proteins were produced by inserting nucleotide sequences that encode a TACI-Fc fusion protein into a mammalian expression vector, and introducing that expression vector into mammalian cells.

A. Ig γ1 Fc4 Fragment Construction

To prepare the TACI-Fc4 fusion protein, the Fc region of human IgG1 (the hinge region and the $CH_2$ and $CH_3$ domains) was modified to remove Fcγ1 receptor (FcγRI) and complement (C1q) binding functions. This modified version of human IgG1 Fc was designated "Fc4."

The Fc region was isolated from a human fetal liver library (Clontech) PCR using oligo primers 5' ATCAGCGGAA TTCAGATCTT CAGACAAAAC TCACACATGC CCAC 3' (SEQ ID NO:7) and 5' GGCAGTCTCT AGATCATTTA CCCGGAGACA GGGAG 3' (SEQ ID NO:8). Mutations within the Fc region were introduced by PCR to reduce FcγRI binding. The FcγRI binding site (Leu-Leu-Gly-Gly; amino acid residues 38 to 41 of SEQ ID NO:6, which correspond to EU index positions 234 to 237) was mutated to Ala-Glu-Gly- Ala to reduce FcγR1 binding (see, for example, Duncan et al., *Nature* 332:563 (1988); Baum et al., *EMBO J.* 13:3992 (1994)). Oligonucleotide primers 5' CCGTGCCCAG CACCTGAAGC CGAGGGGGCA CCGTCAGTCT TCCTCTTCCC C 3' (SEQ ID NO:9) and 5' GGATTCTAGA TTATTTACCC GGAGACAGGG A 3' (SEQ ID NO:10) were used to introduce the mutation. To a 50 µl final volume was added 570 ng of IgFc template, 5 µl of 10× Pfu reaction Buffer (Stratagene), 8 µl of 1.25 mM dNTPs, 31 µl of distilled water, 2 µl of 20 mM oligonucleotide primers. An equal volume of mineral oil was added and the reaction was heated to 94° C. for 1 minute. Pfu polymerase (2.5 units, Stratagene) was added followed by 25 cycles at 94° C. for 30 seconds, 55° C. for 30 seconds, 72° C. for 1 minute followed by a 7 minute extension at 72° C. The reaction products were fractioned by electrophoresis, and the band corresponding to the predicted size of about 676 base pairs was detected. This band was excised from the gel and recovered using a QIAGEN QIAquick™ Gel Extraction Kit (Qiagen) according to the manufacturer's instructions.

PCR was also used to introduce a mutation of Ala to Ser (amino acid residue 134 of SEQ ID NO:6, which corresponds to EU index position 330) and Pro to Ser (amino acid residue 135 of SEQ ID NO:6, which corresponds to EU index position 331) to reduce complement C1q binding or complement fixation (Duncan and Winter, *Nature* 332:788 (1988)). Two first round reactions were performed using the FcγRI binding side-mutated IgFc sequence as a template. To a 50 µl final volume was added 1 µl of FcγRI binding site mutated IgFc template, 5 µl of 10× Pfu Reaction Buffer (Stratagene), 8 µl of 1.25 mM dNTPs, 31 of µl distilled water, 2 µl of 20 mM 5' GGTGGCGGCT CCCAGATGGG TCCTGTCCGA GCCCAGATCT TCAGACAAAA CTCAC 3' (SEQ ID NO:11), a 5' primer beginning at nucleotide 36 of SEQ ID NO:5, and 2 µl of 20 mM 5' TGGGAGGGCT TTGTTGGA 3' (SEQ ID NO:12), a 3' primer beginning at the complement of nucleotide 405 of SEQ ID NO:5. The second reaction contained 2 µl each of 20 mM stocks of oligonucleotide primers 5' TCCAACAAAG CCCTCCCATC CTCCATCGAG AAAACCATCT CC 3' (SEQ ID NO:13), a 5' primer beginning at nucleotide 388 of SEQ ID NO:5 and 5' GGATGGATCC ATGAAGCACC TGTGGTTCTT CCTCCTGCTG GTGGCGGCTC CCAGATG 3' (SEQ ID NO:14), a 3' primer, to introduce the Ala to Ser mutation, XbaI restriction site and stop codon. An equal volume of mineral oil was added and the reactions were heated to 94° C. for 1 minute. Pfu polymerase (2.5 units, Stratagene) was added followed by 25 cycles at 94° C. for 30 seconds, 55° C. for 30 seconds, 72° C. for 2 minutes followed by a 7 minute extension at 72° C. The reaction products were fractionated by electrophoresis, and bands corresponding to the predicted sizes, about 370 and about 395 base pairs respectively, were detected. The bands were excised from the gel and extracted using a QIAGEN QIAquick™ Gel Extraction Kit (Qiagen) according to the manufacturer's instructions.

A second round reaction was performed to join the above fragments and add the 5' BamHI restriction site and a signal sequence from the human immunoglobulin JBL 2'C$_L$ heavy chain variable region (Cogne et al., *Eur. J. Immunol.* 18:1485 (1988)). To a 50 µl final volume was added 30 µl of distilled water, 8 µl of 1.25 mM dNTPs, 5 µl of 10× Pfu polymerase reaction buffer (Stratagene) and 1 µl each of the two first two PCR products. An equal volume of mineral oil was added and the reaction was heated to 94° C. for 1 minute. Pfu polymerase (2.5 units, Stratagene) was added followed by 5 cycles at 94° C. for 30 seconds, 55° C. for 30 seconds, and 72° C. for 2 minutes. The temperature was again brought to 94° C. and 2 µl each of 20 mM stocks of 5' GGATGGATCC ATGAAGCACC TGTGGTTCTT CCTCCTGCTG GTGGCGGCTC CCAGATG 3' (SEQ ID NO:14), a 5' primer beginning at nucleotide 1 of SEQ ID NO:5, and 5' GGATTCTAGA TTATTTACCC GGAGACAGGG A 3' (SEQ ID NO:10) were added followed by 25 cycles at 94° C. for 30 seconds, 55° C. for 30 seconds and 72° C. for 2 minutes, and a final 7 minute extension at 72° C. A portion of the reaction was visualized using gel electrophoresis. A 789 base pair band corresponding the predicted size was detected.

B. TACI-Fc4 Expression Vector Construction

Expression plasmids comprising a coding region for TACI-Fc4 fusion protein were constructed via homologous recombination in yeast. A fragment of TACI cDNA was isolated using PCR that included the polynucleotide sequence from nucleotide 14 to nucleotide 475 of SEQ ID NO:1. The two primers used in the production of the TACI fragment were: (1) a primer containing 40 base pairs of the 5' vector flanking sequence and 17 base pairs corresponding to the amino terminus of the TACI fragment (5' CTCAGCCAGG AAATCCATGC CGAGTTGAGA CGCTTCCGTA GAATGAGTGG CCTGGGCCG 3; SEQ ID NO:15); (2) 40 base pairs of the 3' end corresponding to the flanking Fc4 sequence and 17 base pairs corresponding to the carboxyl terminus of the TACI fragment (5' GCATGTGTGA GTTTTGTCTG AAGATCTGGG CTCCTTCAGC CCCGGGAG 3; SEQ ID NO:16). To a 100 µl final volume was added 10 ng of TACI template, 10 µl of 10× Taq polymerase Reaction Buffer (Perkin Elmer), 8 µl of 2.5 nM dNTPs, 78 µl of distilled water, 2 µl each of 20 mM stocks of the oligonucleotide primers, and Taq polymerase (2.5 units, Life Technology). An equal volume of mineral oil was added and the reaction was heated to 94° C. for 2 minutes, followed by 25 cycles at 94° C. for 30 seconds, 65° C. for 30 seconds, 65° C. for 30 seconds, 72° C. for 1 minute followed by a 5 minute extension at 72° C.

The fragment containing the cDNA encoding the Fc4 fragment was constructed in a similar manner. The two primers used in the production of the Fc4 fragment were (upstream and downstream), an oligonucleotide primer containing 40 base pairs of the 5' TACI flanking sequence and 17 base pairs corresponding to the amino terminus of the Fc4 fragment (5' GCACAGAGGC TCAGAAGCAA GTCCAGCTCT CCCGGGGCTG AAGGAGCCCA GATCTTCAGA 3; SEQ ID NO:17); and an oligonucleotide primer containing 40 base pairs of the 3' end corresponding to the flanking vector sequence and 17 base pairs corresponding to the carboxyl terminus of the Fc4 fragment (5' GGGGTGGGTA CAACCCCAGA GCTGTTTTAA TCTAGATTAT TTACCCGGAG ACAGGG 3; SEQ ID NO:18). To a 100 µl final volume was added 10 ng of Fc4 template described above, 10 µl 10× Taq polymerase Reaction Buffer (Perkin Elmer), 8 µl of 2.5 nM dNTPs, 78 µl of distilled water, 2 µl each of 20 mM stocks of the oligonucleotides, and Taq polymerase (2.5 units, Life Technology). An equal volume of mineral oil was added and the reaction was heated to 94° C. for 2 minutes, then 25 cycles at 94° C. for 30 seconds, 65° C. for 30 seconds, 72° C. for 1 minute followed by a 5 minute extension at 72° C.

Ten microliters of each of the 100 µl PCR reactions described above were run on a 0.8% LMP agarose gel (Seaplaque GTG) with 1×TBE buffer for analysis. The remaining 90 µl of each PCR reaction was precipitated with the addition of 5 µl of 1 M sodium chloride and 250 µl of absolute ethanol. The plasmid pZMP6 was cleaved with SmaI to linearize it at the polylinker. Plasmid pZMP6 was derived from the plasmid pCZR199 (American Type Culture Collection, Manassas, Va., ATCC#98668) and is a mammalian expression vector containing an expression cassette having the cytomegalovirus immediate early promoter, a consensus intron from the variable region of mouse immunoglobulin heavy chain locus, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a dihydrofolate reductase gene and the SV40 terminator. The vector pZMP6 was constructed from pCZR199 by replacement of the metallothionein promoter with the cytomegalovirus immediate early promoter, and the Kozac sequences at the 5' end of the open reading frame.

One hundred microliters of competent yeast cells (S. cerevisiae) were combined with 10 µl containing approximately 1 µg of the TACI extracellular domain and the Fc4 PCR fragments, and 100 ng of SmaI digested pZMP6 vector and transferred to a 0.2 cm electroporation cuvette. The yeast/DNA mixtures were electropulsed at 0.75 kV (5 kV/cm), ∞ ohms, 25 µF. To each cuvette was added 600 µl of 1.2 M sorbitol and the yeast were plated in two 300 µl aliquots onto to URA-D plates and incubated at 30° C.

After about 48 hours, the Ura+ yeast transformants from a single plate were resuspended in 1 ml of water and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl of ethanol, followed by centrifugation for 10 minutes at 4° C. The DNA pellet was resuspended in 100 µl of water.

Transformation of electrocompetent E. coli cells (DH10B, GibcoBRL) was performed with 0.5-2 ml yeast DNA prep and 40 µl of DH10B cells. The cells were electropulsed at 2.0 kV, 25 mF and 400 ohms Following electroporation, 1 ml of SOC (2% Bacto-Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) were plated in 250 µl aliquots on four LB AMP plates (LB broth (Lennox), 1.8% Bacto-Agar (Difco), 100 mg/L Ampicillin).

Individual clones harboring the correct expression construct for TACI-Fc4 were identified by restriction digest to verify the presence of the insert and to confirm that the various DNA sequences have been joined correctly to one another. The insert of positive clones were subjected to sequence analysis. Larger scale plasmid DNA is isolated using the Qiagen Maxi kit (Qiagen) according to manufacturer's instructions.

C. Construction of Fc5, Fc6, and Fc7

In Fc5, the Arg residue at EU index position 218 was changed back to a Lys residue. Wild-type human Ig γ1 contains a lysine at this position. Briefly, nucleic acid molecules encoding Fc5 were produced using oligonucleotide primers 5' GAGCCCAAATCTTCAGACAAAACTCACA-CATGCCCA 3' (SEQ ID NO:19) and 5' TAATTGGCGCGC-CTCTAGATTATTTACCCGGAGACA 3' (SEQ ID NO:20). The conditions of the PCR amplification were as follows. To a 50 µl final volume was added 236 ng of Fc4 template, 5 µl of 10 Pfu reaction Buffer (Stratagene), 4 µl of 2.5 mM dNTPs, 1 µl of 20 µM of each of the oligonucleotides, and 1 µl of Pfu polymerase (2.5 units, Stratagene). The amplification thermal profile consisted of 94° C. for 2 minutes, 5 cycles at 94° C. for 15 seconds, 42° C. for 20 seconds, 72° C. for 45 seconds, 20 cycles at 94° C. for 15 seconds, 72° C. for 1 minute 20 seconds, followed by a 7 minute extension at 72° C. The reaction product was fractionated by agarose gel electrophoresis, and the band corresponding to the predicted size of about 718 base pairs was detected. The band was excised from the gel and recovered using a QIAGEN QIAquick Gel Extraction Kit (Qiagen) according to the manufacturer's instructions.

Fc6 is identical to Fc5 except that the carboxyl terminal lysine codon has been eliminated. As in Fc4 and Fc5 above, the stop codon in the Fc6 sequence was changed to TAA. Fc6 was generated from template DNA that encoded Fc5 using oligonucleotide primers 5' GAGCCCAAAT CTTCAGA-CAA AACTCACACA TGCCCA 3' (SEQ ID NO:19) and 5' GGCGCGCCTC TAGATTAACC CGGAGACAGG GAGAGGC 3' (SEQ ID NO:21).

Fc7 is identical to the wild-type γ1 Fc except for an amino acid substitution at EU index position Asn 297 located in the $C_{H2}$ domain. Asn 297 was mutated to a Gln residue to prevent the attachment of N-linked carbohydrate at that residue position. As above, the stop codon in the Fc7 sequence was changed to TAA. Fc7 was generated by overlap PCR using a wild-type human IgGγ1 Fc cDNA as the template and oligonucleotide primers 5' GAGCCCAAATCTTGCGA-CAAAACTCACA 3' (SEQ ID NO:22) and 5' GTACGT-GCTTTGGTACTGCTCCTCCCGCGGCTT 3' (SEQ ID NO:23) to generate the 5' half of Fc7, and oligonucleotide primers 5' CAGTACCAAAGCACGTACCGTGTGGTCA 3' (SEQ ID NO:24) and 5' TAATTGGCGCGCCTCTAGAT-TATTTACCCGGAGACA 3' (SEQ ID NO:20) to generate the 3' half of Fc7. The two PCR products were combined and amplified using oligonucleotide primers 5' GAGC-CCAAATCTTGCGACAAAACTCACA 3' (SEQ ID NO:22) and 5' TAATTGGCGCGCCTCTAGATTATTTAC-CCGGAGACA 3' (SEQ ID NO:20).

All the resultant PCR products were gel purified, cloned, and verified by DNA sequence analysis.

D. Construction of Amino-Truncated TACI-Fc Fusion Proteins

Four amino terminal truncated versions of TACI-Fc were generated. All four had a modified human tissue plasminogen activator signal sequence (SEQ ID NO:25) fused to amino acid residue number 30 of SEQ ID NO:2. However, the four proteins differed in the location of point in which the Fc5 was fused to the TACI amino acid sequence of SEQ ID NO:2. Table 3 outlines the structures of the four fusion proteins.

TABLE 3

TACI Fusion Proteins

| Designation of TACI-Fc | TACI amino acid residues |
| --- | --- |
| TACI(d1-29)-Fc5 | 30 to 154 of SEQ ID NO: 2 |
| TACI(d1-29, d107-154)-Fc5 | 30 to 106 of SEQ ID NO: 2 |
| TACI(d1-29, d111-154)-Fc5 | 30 to 110 of SEQ ID NO: 2 |
| TACI(d1-29, d120-154)-Fc5 | 30 to 119 of SEQ ID NO: 2 |

Protein encoding expression cassettes were generated by overlap PCR using standard techniques (see, for example, Horton et al., Gene 77:61 (1989)). A nucleic acid molecule encoding TACI and a nucleic acid molecule encoding Fc5 were used as PCR templates. Oligonucleotide primers are identified in Tables 4 and 5.

TABLE 4

Oligonucleotide Primers Used to Produce TACI Fusion Proteins

| | Oligonucleotide Designations | | | |
|---|---|---|---|---|
| Designation of TACI-Fc | 5' TACI | 3' TACI | 5' Fc5 | 3' Fc5 |
| TACI(d1-29)-Fc5 | ZC24,903 | ZC24,955 | ZC24,952 | ZC24,946 |
| TACI(d1-29, d107-154)-Fc5 | ZC24,903 | ZC24,951 | ZC24,949 | ZC24,946 |
| TACI(d1-29, d111-154)-Fc5 | ZC24,903 | ZC28,978 | ZC28,979 | ZC24,946 |
| TACI(d1-29, d120-154)-Fc5 | ZC24,903 | ZC28,981 | ZC28,980 | ZC24,946 |

TABLE 5

Oligonucleotide Sequences

| Primer | Nucleotide Sequence | SEQ ID NO. |
|---|---|---|
| ZC24,903 | 5' TATTAGGCCGGCCACCATGGATGCAATGA 3' | 40 |
| ZC24,955 | 5' TGAAGATTTGGGCTCCTTGAGACCTGGGA 3' | 41 |
| ZC24,952 | 5' TCCCAGGTCTCAAGGAGCCCAAATCTTCA 3' | 42 |
| ZC24,946 | 5' TAATTGGCGCGCCTCTAGATTATTTACCCGGAGACA 3' | 20 |
| ZC24,951 | 5' TGAAGATTTGGGCTCGTTCTCACAGAAGTA 3' | 43 |
| ZC24,949 | 5' ATACTTCTGTGAGAACGAGCCCAAATCTTCA 3' | 44 |
| ZC28,978 | 5' TTTGGGCTCGCTCCTGAGCTTGTTCTCACA 3' | 45 |
| ZC28,979 | 5' CTCAGGAGCGAGCCCAAATCTTCAGACA 3' | 46 |
| ZC28,981 | 5' TTTGGGCTCCCTGAGCTCTGGTGGAA 3' | 47 |
| ZC28,980 | 5' GAGCTCAGGGAGCCCAAATCTTCAGACA 3' | 48 |

The first round of PCR amplifications consisted of two reactions for each of the four amino terminal truncated versions. The two reactions were performed separately using the 5' and 3' TACI oligonucleotides in one reaction, and the 5' and 3' Fc5 oligonucleotides in another reaction for each version. The conditions of the first round PCR amplification were as follows. To a 25 µl final volume was added approximately 200 ng template DNA, 2.5 µl 10× Pfu reaction Buffer (Stratagene), 2 µl of 2.5 mM dNTPs, 0.5 µl of 20 µM each 5' oligonucleotide and 3' oligonucleotide, and 0.5 µl Pfu polymerase (2.5 units, Stratagene). The amplification thermal profile consisted of 94° C. for 3 minutes, 35 cycles at 94° C. for 15 seconds, 50° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

The second round of PCR amplification, or overlap PCR amplification reaction, was performed using the gel purified fragments from the first round PCR as DNA template. The conditions of the second round PCR amplification were as follows. To a 25 µl final volume was added approximately 10 ng template DNA each of the TACI fragment and the Fc5 fragment, 2.5 µl 10× Pfu reaction Buffer (Stratagene), 2 µl of 2.5 mM dNTPs, 0.5 µl of 20 µM each ZC24,903 (SEQ ID NO:40) and ZC24,946 (SEQ ID NO:20) and 0.5 µl Pfu polymerase (2.5 units, Stratagene). The amplification thermal profile consisted of 94° C. for 1 minute, 35 cycles at 94° C. for 15 seconds, 55° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

Each of the four versions of the amino terminal truncated TACI-Fc PCR products were separately cloned using Invitrogen's ZEROBLUNT TOPO PCR Cloning Kit following the manufacturer's recommended protocol. Table 6 identifies the nucleotide and amino acid sequences of these TACI-Fc constructs.

TABLE 6

Sequences of TACI-Fc Variants

| | SEQ ID Nos. | |
|---|---|---|
| Designation of TACI-Fc | Nucleotide | Amino Acid |
| TACI(d1-29)-Fc5 | 49 | 50 |
| TACI(d1-29, d107-154)-Fc5 | 51 | 52 |
| TACI(d1-29, d111-154)-Fc5 | 53 | 54 |
| TACI(d1-29, d120-154)-Fc5 | 55 | 56 |

After the nucleotide sequences were verified, plasmids comprising each of the four versions of the amino terminal truncated TACI-Fc fusions were digested with FseI and AscI to release the amino acid encoding segments. The FseI-AscI fragments were ligated into a mammalian expression vector containing a CMV promoter and an SV40 poly A segment. Expression vectors were introduced into Chinese hamster ovary cells as described below.

Example 2

Production of TACI-Fc Proteins by Chinese Hamster Ovary Cells

The TACI-Fc expression constructs were used to transfect, via electroporation, suspension-adapted Chinese hamster ovary (CHO) DG44 cells grown in animal protein-free medium (Urlaub et al., *Som. Cell. Molec. Genet.* 12:555 (1986)). CHO DG44 cells lack a functional dihydrofolate reductase gene due to deletions at both dihydrofolate reductase chromosomal locations. Growth of the cells in the presence of increased concentrations of methotrexate results in the amplification of the dihydrofolate reductase gene, and the linked recombinant protein-encoded gene on the expression construct.

CHO DG44 cells were passaged in PFCHO media (JRH Biosciences, Lenexa, Kans.), 4 mM L-Glutamine (JRH Biosciences), and 1× hypothanxine-thymidine supplement (Life Technologies), and the cells were incubated at 37° C. and 5% $CO_2$ in Corning shake flasks at 120 RPM on a rotating shaker platform. The cells were transfected separately with linearized expression plasmids. To ensure sterility, a single ethanol precipitation step was performed on ice for 25 minutes by combining 200 µg of plasmid DNA in an Eppendorf tube with 20 µl of sheared salmon sperm carrier DNA (5'→3' Inc. Boulder, Colo., 10 mg/ml), 22 µl of 3M NaOAc (pH 5.2), and 484 µl of 100% ethanol (Gold Shield Chemical Co., Hayward, Calif.). After incubation, the tube was centrifuged at 14,000 RPM in a microfuge placed in a 4° C. cold room, the supernatant removed and the pellet washed twice with 0.5 ml of 70% ethanol and allowed to air dry.

The CHO DG44 cells were prepared while the DNA pellet was drying by centrifuging $10^6$ total cells (16.5 ml) in a 25 ml conical centrifuge tube at 900 RPM for 5 minutes. The CHO DG44 cells were resuspended into a total volume of 300 µl of PFCHO growth media, and placed in a Gene-Pulser Cuvette with a 0.4 cm electrode gap (Bio-Rad). The DNA, after approximately 50 minutes of drying time, was resuspended into 500 µl of PFCHO growth media and added to the cells in the cuvette so that the total volume did not exceed 800 µl and was allowed to sit at room temperature for 5 minutes to decrease bubble formation. The cuvette was placed in a Bio-Rad Gene Pulser II unit set at 0.296 kV (kilovolts) and 0.950 HC (high capacitance) and electroporated immediately.

The cells were incubated 5 minutes at room temperature before placement in 20 ml total volume of PFCHO media in a CoStar T-75 flask. The flask was placed at 37° C. and 5% $CO_2$ for 48 hours when the cells were then counted by hemocytometer utilizing trypan blue exclusion and put into PFCHO selection media without hypothanxine-thymidine supplement and containing 200 mM methotrexate (Cal Biochem).

Upon recovery of the methotrexate selection process, the conditioned media containing the secreted TACI-Fc proteins were examined by Western Blot analysis.

Example 3

Structural Analysis of TACI-Fc Proteins

In certain cases, TACI-Fc fusion proteins were partially purified before analysis. Conditioned medium from Chinese hamster ovary cultures was sterile-filtered through a 0.22 µm filter and the TACI-Fc protein was captured on a protein A column. The protein A-bound material was eluted and passed over an S-200 size exclusion column for final purification.

Western blot analysis was performed on both conditioned cell medium and purified protein to assess the structural stability of the TACI-Fc proteins. Briefly, protein or supernatant samples were transferred to nitrocellulose membranes and the TACI-Fc proteins were detected using peroxidase conjugated goat anti-mouse IgG2a (Boehringer Mannheim), or peroxidase conjugated goat anti-human IgG Fc specific antisera (Pierce).

Amino terminal amino acid sequence analyses were performed on Models 476A and 494 Protein Sequencer Systems from Perkin Elmer Applied Biosystems Division (Foster City, Calif.). Data analysis was performed with Applied Biosystems Model 610A Data Analysis System for Protein Sequencing, version 2.1a (Applied Biosystems, Inc.). Most supplies and reagents used were from Applied Biosystems, Inc.

Example 4

Functional Analysis of TACI-Fc Proteins

Two approaches were used to examine the binding characteristics of four TACI-Fc proteins with ZTNF4. One approach measured the ability of the TACI-Fc constructs to compete with TACI-coated plates for binding of $^{125}$I-labeled ZTNF4. In the second approach, increasing concentrations of $^{125}$I labeled ZTNF4 were incubated with each of the TACI-Fc constructs, and the radioactivity associated with precipitated ZTNF4-TACI-Fc complexes was determined. The TACI-Fc fusion proteins had TACI moieties that lacked the first 29 amino acid residues of the amino acid sequence of SEQ ID NO:2. One of the fusion proteins had a TACI moiety with an intact stalk region (TACI (d1-29)-Fc5), whereas three of the TACI-Fc fusion proteins had TACI moieties with various deletions in the stalk region (TACI (d1-29, d107-154)-Fc5; TACI (d1-29, d111-154)-Fc5; TACI (d1-29, d120-154)-Fc5).

A. Competitive Binding Assay

ZTNF4 was radioiodinated with Iodobeads (Pierce), following standard methods. Briefly, 50 µg of the ZTNF4 was iodinated with 4 mCi of $^{125}$I using a single Iodobead. The reaction was quenched with a 0.25% solution of bovine serum albumin, and the free $^{125}$I was removed by gel filtration using a PD-10 column (Pierce). The specific radioactivity of $^{125}$I-ZTNF4 preparations was determined by trichloroacetic acid precipitation before and after the desalting step.

An N-terminal fragment of the TACI receptor, designated as "TACI-N," was added to 96-well plates (100 µl at 0.1 µg/ml), and incubated overnight at 4° C. The plates were washed, blocked with Superblock (Pierce), and washed again. The TACI-Fc constructs, at various concentrations ranging from 0 to 11.5 ng/ml, were mixed with a fixed concentration of $^{125}$I-ZTNF4 (20 ng/ml), and incubated for 2 hours at 37° C. on the plate coated with TACI-N. Controls contained either TACI-N in solution, or lacked TACI-Fc. After incubation, the plates were washed and counted. Each determination was performed in triplicate.

The results showed that all TACI-Fc constructs inhibited $^{125}$I-ZTNF4 binding completely at concentrations of about 100 ng/ml or greater. The TACI-Fc proteins, TACI (d1-29)-Fc5, TACI (d1-29, d111-154)-Fc5, and TACI (d1-29, d120-154)-Fc5, were more effective inhibitors than the TACI-Fc construct, TACI (d1-29, d107-154)-Fc5. An Fc fragment alone did not inhibit binding. $IC_{50}$ values were calculated for each construct in three experiments. The average values for the constructs were: TACI (d1-29)-Fc5: 2.07 nM; TACI (d1-29, d107-154)-Fc5: 4.95 nM; TACI (d1-29, d111-154)-Fc5: 2.31 nM; and TACI (d1-29, d120-154)-Fc5: 2.21 nM.

B. Solution Binding Assay

At a concentration of 0.05 nM, each TACI-Fc construct was incubated with 0.4 pM to 1.5 nM $^{125}$I-ZTNF4 for 30 minutes at room temperature in a total volume of 0.25 ml/tube. A Pansorbin (Staph A) suspension was added to each tube, and after 15 minutes, the samples were centrifuged, washed twice, and the pellets counted. Nonspecific binding was determined by the addition of 130 nM unlabeled ZTNF4 to the $^{125}$I-ZTNF4/TACI-Fc mix. Specific binding was calculated by subtracting the cpm bound in the presence of unlabeled ZTNF4 from the total cpm bound at each concentration of $^{125}$I-ZTNF4. Each determination was performed in triplicate. Binding constants were calculated using GraphPad Prism software (MacIntosh v. 3.0).

Figure 4:
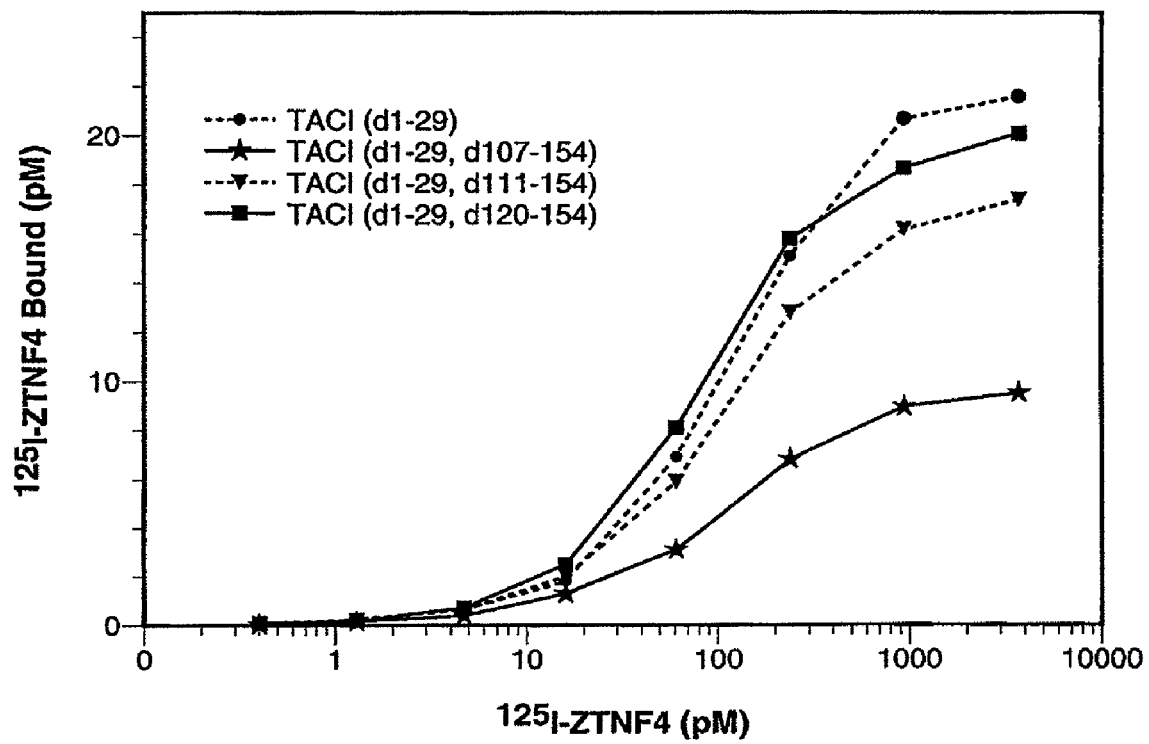
FIG. 4 shows the specific binding of $^{125}$I-ZTNF4 with various TACI-Fc constructs. The TACI-Fc fusion proteins had TACI moieties that lacked the first 29 amino acid residues of the amino acid sequence of SEQ ID NO:2. One of the fusion proteins had a TACI moiety with an intact stalk region (TACI (d1-29)-Fc5), whereas three of the TACI-Fc fusion proteins had TACI moieties with various deletions in the stalk region (TACI (d1-29, d107-154)-Fc5; TACI (d1-29, d111-154)-Fc5; TACI (d1-29, d120-154)-Fc5). Experimental details are described in Example 4.

FIG. 4 illustrates the specific binding of $^{125}$I-ZTNF4 to the various TACI-Fc constructs. Binding appeared to approach saturation with each construct, and was significantly higher for constructs TACI (d1-29)-Fc5, TACI (d1-29, d111-154)-Fc5, TACI (d1-29, d120-154)-Fc5, as compared with the binding of TACI (d1-29, d107-154)-Fc5. Bmax and Kd values were calculated, and the results are summarized in Table 7.

TABLE 7

Binding of $^{125}$I-ZTNF4 to TACI-Fc Constructs

| TACI-Fc Construct | Kd (nM) | Bmax (nM) |
|---|---|---|
| TACI (d1-29)-Fc5 | 0.134 | 0.023 |
| TACI (d1-29, d107-154)-Fc5 | 0.121 | 0.010 |
| TACI (d1-29, d111-154)-Fc5 | 0.115 | 0.018 |
| TACI (d1-29, d120-154)-Fc5 | 0.092 | 0.021 |

Example 5

Measurement of Circulating ZTNF4

Levels of ZTNF4 in individuals with a disease condition (such as SLE, rheumatoid arthritis for example) relative to normal individuals were determined using an electrochemiluminescence assay. A standard curve prepared from soluble, human ZTNF4 at 10 ng/ml, 1 ng/ml, 0.1 ng/ml, 0.01 ng/ml and 0 ng/ml was prepared in ORIGIN buffer (Igen, Gaithersburg, Md.). Serum samples were diluted in ORIGIN buffer. The standards and samples were incubated at room temperature for two hours with biotinylated rabbit anti-human ZTNF4-NF BV antibody diluted to 1 µg/ml in Origin Assay Buffer (IGEN) and ruthenylated rabbit anti-human ZTNF4-NF BV polyclonal antibody diluted to 1 µg/ml in Origin Assay Buffer (IGEN). Following the incubation the samples were vortexed and 0.4 mg/ml streptavidin Dynabeads (Dynal, Oslo, Norway) were added to each of the standards and samples at 50 µl/tube and incubated for 30 minutes at room temperature. Samples were then vortexed and samples were read on an Origin Analyzer (Igen) according to manufacturer's instructions. The Origin assay is based on electrochemiluminescence and produces a readout in ECL. In one study, an elevated level of ZTNF4 was detected in the serum samples from both NZBWF1/J, and MRL/Mpj-Fas$^{lpr}$ mice, which have progressed to advanced stages of glomerulonephritis and autoimmune disease.

The ORIGIN ASSAY was also used to measure levels of ZTNF4 in the blood of SLE patients, relative to circulating levels in normal individuals. A standard curve prepared from soluble, human ZTNF4 at 10 ng/ml, 1 ng/ml, 0.1 ng/ml, 0.01 ng/ml and 0 ng/ml was prepared in ORIGIN buffer (Igen). All patient samples were run in triplicate with a 25 µl final volume. The standards and samples were incubated at room temperature for two hours with a capture antibody, biotinylated rabbit anti-human ZTNF4-NF BV polyclonal antibody, diluted to 1 µg/ml in Origin Assay Buffer (IGEN) and a detection antibody, ruthenylated rabbit anti-human ZTNF4-NF BV polyclonal antibody, diluted to 1 µg/ml in Origin Assay Buffer (IGEN). Following the incubation the samples were vortexed, and 0.4 mg/ml streptavidin Dynabeads (Dynal) was added to each of the standards and samples at 50 µl/tube and incubated for 30 minutes at room temperature. Samples were then vortexed, and analyzed using an Origin 1.5 Analyzer (Igen) according to manufacturer's instructions.

This assay included 28 normal control samples and samples from 20 patients diagnosed with SLE. Elevated levels of ZTNF4 were observed in the serum of patients diagnosed with SLE, as compared with normal control serum donors. ZTNF4 levels were calculated as a fold increase of ZTNF4 levels in the patient or control samples as compared to an arbitrary human reference serum sample. The average of the 28 control samples was 1.36 fold over the human reference sample and the average of the 20 SLE patient samples was 4.92. Seven out of the 20 SLE patients had ZTNF4 levels that were two fold over the average of the control samples, whereas there was only one control individual that had a greater than two fold level over the control average.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for inhibiting the proliferation of B cell cancers comprising administering to the tumor cells in need thereof a composition comprising a transmembrane activator and calcium modulator and cyclophilin ligand-interactor (TACI)-immunoglobulin fusion protein, wherein the TACI-immunoglobulin fusion protein comprises:
   (a) a TACI receptor moiety that consists off
       i) amino acid residues 30-110 of SEQ ID NO:2; or,
       ii) amino acid residues 30-154 of SEQ ID NO:2;
   wherein the TACI receptor moiety binds at least one of ZTNF2 or ZTNF4, and
   (b) an immunoglobulin moiety comprising a CH2 and CH3 domain.

2. The method of claim 1, wherein the composition comprises a pharmaceutical composition that comprises the TACI-immunoglobulin fusion protein and a pharmaceutically acceptable carrier, and wherein the pharmaceutical composition is administered to a mammalian subject which has a B cell cancer.

3. The method of claim 2, wherein the administration of the pharmaceutical composition inhibits the proliferation of B lymphocytes in the mammalian subject.

4. The method of claim 1, wherein the immunoglobulin moiety is an IgG1 immunoglobulin moiety.

5. The method of claim 4, wherein the immunoglobulin moiety is an IgG1 Fc fragment that comprises a disulfide linked heavy chain hinge region, a $C_{H2}$ domain and a $C_{H3}$ domain.

6. The method of claim 1, wherein the TACI-immunoglobulin fusion protein has an amino acid sequence of SEQ ID NO:54.

7. The method of claim 1, wherein the TACI-immunoglobulin fusion protein has an amino acid sequence comprising the secreted form of the amino acid sequence of SEQ ID NO:54.

8. The method of claim 1, wherein the TACI-immunoglobulin fusion protein comprises the amino acid sequence of SEQ ID NO:54, wherein the optimized tPA (otPA) leader sequence (SEQ ID NO:25) has been removed.

9. The method of claim 1, wherein the composition is administered to cells cultured in vitro.

10. The method of claim 1, wherein the TACI-immunoglobulin fusion protein is a dimer.

11. A method for reducing circulating blood levels of ZTNF4 in a mammalian subject comprising administering to the mammalian subject a composition comprising a transmembrane activator and calcium modulator and cyclophilin ligand-interactor (TACI)-immunoglobulin fusion protein, wherein the TACI-immunoglobulin fusion protein comprises:

(a) a TACI receptor moiety that consists of
 i) amino acid residues 30-110 of SEQ ID NO:2; or,
 ii) amino acid residues 30-154 of SEQ ID NO:2;
wherein the TACI receptor moiety binds ZTNF4, and (b) an immunoglobulin moiety comprising a $C_{H2}$ and $C_{H3}$ domain.

12. The method of claim 11, wherein the immunoglobulin moiety is an IgG1 immunoglobulin moiety.

13. The method of claim 12, wherein the immunoglobulin moiety is an IgG1 Fc fragment that comprises a disulfide linked heavy chain hinge region, a $C_{H2}$ domain and a $C_{H3}$ domain.

14. The method of claim 11, wherein the TACI-immunoglobulin fusion protein has an amino acid sequence of SEQ ID NO:54.

15. The method of claim 11, wherein the TACI-immunoglobulin fusion protein has an amino acid sequence comprising the secreted form of the amino acid sequence of SEQ ID NO:54.

16. The method of claim 11, wherein the TACI-immunoglobulin fusion protein comprises the amino acid sequence of SEQ ID NO:54, wherein the optimized tPA (otPA) leader sequence (SEQ ID NO:25) has been removed.

17. The method of claim 11, wherein the composition is administered to cells cultured in vitro.

18. The method of claim 11, wherein the TACI-immunoglobulin fusion protein is a dimer.

* * * * *

UNITED STATES PATENT AND TRADEMARK OFFICE
CERTIFICATE OF CORRECTION

| | | |
|---|---|---|
| PATENT NO. | : 7,862,814 B2 | |
| APPLICATION NO. | : 12/613039 | |
| DATED | : January 4, 2011 | |
| INVENTOR(S) | : Rixon et al. | |

It is certified that error appears in the above-identified patent and that said Letters Patent is hereby corrected as shown below:

Column 4, line 1, "TACT" should be --TACI--;

Column 8, line 9, "TACT" should be --TACI--;

Column 11, line 14, "von Billow" should be --von Büllow--;

Column 11, line 29, "von Billow" should be --von Büllow--; and

Column 125, Claim 1, line 59, "consists off" should be --consists of--.

Signed and Sealed this
Twenty-third Day of August, 2011

David J. Kappos
*Director of the United States Patent and Trademark Office*